United States Patent
Brambilla

(10) Patent No.: US 9,038,635 B2
(45) Date of Patent: *May 26, 2015

(54) VENTILATION MASK WITH INTEGRATED PILOTED EXHALATION VALVE

(71) Applicant: Breathe Technologies, Inc., Irvine, CA (US)

(72) Inventor: Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 13/798,931

(22) Filed: Mar. 13, 2013

(65) Prior Publication Data

US 2013/0190643 A1 Jul. 25, 2013

Related U.S. Application Data

(63) Continuation-in-part of application No. 13/572,368, filed on Aug. 10, 2012, which is a continuation-in-part of application No. 13/411,407, filed on Mar. 2, 2012, now Pat. No. 8,839,791, which is a
(Continued)

(51) Int. Cl.
*A61M 11/00* (2006.01)
*A61M 16/08* (2006.01)
(Continued)

(52) U.S. Cl.
CPC ....... *A61M 16/0875* (2013.01); *A61M 16/0057* (2013.01); *A61M 16/0666* (2013.01);
(Continued)

(58) Field of Classification Search
CPC ................. A61M 2210/0618; A61M 16/0666; A61M 16/0816; A61M 16/0875
USPC .............. 128/207.13, 201.13, 205.24, 207.18
See application file for complete search history.

(56) References Cited

U.S. PATENT DOCUMENTS

| 8,413 | A | 10/1851 | St. John |
| 42,346 | A | 4/1864 | Ghambeblin |

(Continued)

FOREIGN PATENT DOCUMENTS

| AU | 2003217098 A1 | 12/2003 |
| CA | 1315174 C | 3/1993 |

(Continued)

OTHER PUBLICATIONS

Exhaled Tidal Volume Overestimation in Mechanically Ventilated Patients With Large Cardiogenic Oscillation. Imanaka H, Takeuchi M, Tachibana K, Nishimura M. Crit Care Med. Jul. 2004;32(7):1546-9.

(Continued)

*Primary Examiner* — Steven Douglas
(74) *Attorney, Agent, or Firm* — Stetina Brunda Garred & Brucker

(57) ABSTRACT

The disclosure is directed to various tubing arrangements and an associated Y-connector which may be used to facilitate the operative interface of the mask to a ventilator within a ventilation system. The tubing arrangement may comprise a pair of bi-lumen tubes. One end of each of the bi-lumen tubes is fluidly connected to the mask, with the opposite end being fluidly connected to the Y-connector. The Y-connector is in turn fluidly connected to one end of either a tri-lumen tube or a quad-lumen tube also included in the tubing arrangement, the opposite end of such tri-lumen tube or quad-lumen tube being fluidly connected to the ventilator. The Y-connector is uniquely configured to fluidly connect certain lumens of the tri-lumen tube or the quad-lumen tube to dedicated, corresponding ones of the lumens included in respective ones of the bi-lumen tubes, and to further allow for the selective detachment of the tri-lumen tube or the quad-lumen tube from the bi-lumen tubes.

20 Claims, 23 Drawing Sheets

Related U.S. Application Data continuation-in-part of application No. 13/411,348, filed on Mar. 2, 2012, now Pat. No. 8,844,533.

(60) Provisional application No. 61/499,950, filed on Jun. 22, 2011, provisional application No. 61/512,750, filed on Jul. 28, 2011.

(51) Int. Cl.

| | |
|---|---|
| *A61M 16/00* | (2006.01) |
| *A61M 16/06* | (2006.01) |
| *A61B 5/097* | (2006.01) |
| *A61M 16/20* | (2006.01) |
| *A61B 5/03* | (2006.01) |
| *A61B 5/087* | (2006.01) |
| *A61M 16/10* | (2006.01) |

(52) U.S. Cl.
CPC ............... *A61B5/097* (2013.01); *A61M 16/20* (2013.01); *A61M 16/0816* (2013.01); *A61B 5/03* (2013.01); *A61B 5/087* (2013.01); *A61M 16/1045* (2013.01); *A61M 16/0066* (2013.01); *A61M 16/0833* (2014.02); *A61M 16/201* (2014.02); *A61M 16/207* (2014.02)

(56) References Cited

U.S. PATENT DOCUMENTS

| | | |
|---|---|---|
| 53,694 A | 4/1866 | Smith |
| 53,695 A | 4/1866 | Somes |
| 189,153 A | 4/1877 | Towle et al. |
| 252,515 A | 1/1882 | Ebdshaw |
| 306,346 A | 10/1884 | Pabaf-Javal |
| 321,600 A | 7/1885 | Heckee |
| 416,701 A | 12/1889 | Yocom |
| 430,380 A | 6/1890 | Evarts |
| 432,325 A | 7/1890 | McIntyre |
| 474,434 A | 5/1892 | Banker |
| 516,494 A | 3/1894 | La Veck |
| 539,217 A | 5/1895 | Chapman |
| 546,673 A | 9/1895 | Meyer |
| 694,089 A | 2/1902 | Brewer |
| 3,326,214 A | 6/1967 | McCoy |
| 3,726,275 A | 4/1973 | Jackson et al. |
| 3,802,431 A | 4/1974 | Farr |
| 3,881,482 A | 5/1975 | Lindholm et al. |
| 4,062,359 A | 12/1977 | Geaghan |
| 4,121,583 A | 10/1978 | Chen |
| 4,245,633 A | 1/1981 | Erceg |
| 4,266,540 A | 5/1981 | Panzik et al. |
| 4,278,082 A | 7/1981 | Blackmer |
| 4,318,398 A | 3/1982 | Oetjen |
| 4,325,365 A | 4/1982 | Barbuto |
| 4,458,679 A | 7/1984 | Ward |
| 4,535,767 A | 8/1985 | Tiep et al. |
| 4,559,941 A | 12/1985 | Timmons et al. |
| 4,572,177 A | 2/1986 | Tiep et al. |
| 4,620,537 A | 11/1986 | Brown |
| 4,699,139 A | 10/1987 | Marshall |
| 4,739,757 A | 4/1988 | Edwards |
| 4,771,770 A | 9/1988 | Artemenko et al. |
| 4,787,105 A | 11/1988 | Phillips et al. |
| 4,793,343 A | 12/1988 | Cummins et al. |
| 4,836,200 A | 6/1989 | Clark et al. |
| 4,873,972 A | 10/1989 | Magidson et al. |
| 4,913,140 A | 4/1990 | Orec |
| 4,949,733 A | 8/1990 | Sampson et al. |
| D311,609 S | 10/1990 | Stoneburner |
| 5,018,519 A | 5/1991 | Brown |
| 5,025,805 A | 6/1991 | Nutter |
| 5,062,145 A | 10/1991 | Zwaan et al. |
| 5,065,756 A | 11/1991 | Rapoport |
| 5,072,729 A | 12/1991 | DeVries |
| 5,111,809 A | 5/1992 | Gamble et al. |
| 5,117,820 A | 6/1992 | Robitaille |
| 5,134,995 A | 8/1992 | Gruenke et al. |
| 5,193,534 A | 3/1993 | Peppler |
| 5,245,995 A | 9/1993 | Sullivan et al. |
| 5,284,160 A | 2/1994 | Dryden |
| 5,303,699 A | 4/1994 | Bonassa et al. |
| 5,331,957 A | 7/1994 | Liu |
| 5,353,788 A | 10/1994 | Miles et al. |
| 5,367,604 A | 11/1994 | Murray |
| 5,383,447 A | 1/1995 | Lang |
| 5,400,776 A | 3/1995 | Bartholomew |
| 5,433,192 A | 7/1995 | Ebeling |
| 5,435,298 A | 7/1995 | Anthony |
| 5,445,143 A | 8/1995 | Sims |
| 5,462,048 A | 10/1995 | Lambert et al. |
| 5,492,113 A | 2/1996 | Estes et al. |
| 5,503,146 A | 4/1996 | Froehlich et al. |
| 5,505,768 A | 4/1996 | Altadonna |
| 5,529,060 A | 6/1996 | Salmon et al. |
| 5,537,996 A | 7/1996 | McPhee |
| 5,537,997 A | 7/1996 | Mechlenburg et al. |
| 5,542,416 A | 8/1996 | Chalvignac |
| 5,546,930 A | 8/1996 | Wikefeldt |
| 5,551,419 A | 9/1996 | Froehlich et al. |
| 5,558,084 A | 9/1996 | Daniell et al. |
| 5,586,551 A | 12/1996 | Hilliard |
| 5,588,423 A | 12/1996 | Smith |
| 5,595,173 A | 1/1997 | Dodd |
| 5,598,837 A | 2/1997 | Sirianne et al. |
| 5,598,838 A | 2/1997 | Servidio |
| 5,617,913 A | 4/1997 | DeGregoria et al. |
| 5,640,951 A | 6/1997 | Huddart et al. |
| 5,645,049 A | 7/1997 | Foley |
| 5,647,344 A | 7/1997 | Turnbull |
| 5,655,522 A | 8/1997 | Mechlenburg et al. |
| 5,666,950 A | 9/1997 | Smith |
| 5,673,687 A | 10/1997 | Dobson et al. |
| 5,685,296 A | 11/1997 | Zdrojkowski et al. |
| 5,694,923 A | 12/1997 | Hete et al. |
| 5,701,891 A | 12/1997 | Groenke |
| 5,704,916 A | 1/1998 | Byrd |
| 5,709,204 A | 1/1998 | Lester |
| 5,730,122 A | 3/1998 | Lurie |
| 5,735,267 A | 4/1998 | Tobia |
| 5,813,399 A | 9/1998 | Isaza et al. |
| 5,836,303 A | 11/1998 | Hurst et al. |
| 5,848,590 A | 12/1998 | Smith |
| 5,853,884 A | 12/1998 | Nichols et al. |
| 5,860,418 A | 1/1999 | Lundberg |
| 5,937,855 A | 8/1999 | Zdrojkowski et al. |
| 5,957,131 A | 9/1999 | Hutchinson et al. |
| 5,964,219 A | 10/1999 | Pekka |
| 6,014,890 A | 1/2000 | Breen |
| 6,017,374 A | 1/2000 | Huxham |
| 6,026,811 A | 2/2000 | Settle |
| 6,050,260 A | 4/2000 | Daniell et al. |
| 6,078,730 A | 6/2000 | Huddart et al. |
| 6,095,135 A | 8/2000 | Clawson et al. |
| 6,116,235 A | 9/2000 | Walters et al. |
| 6,135,432 A | 10/2000 | Hebblewhite et al. |
| 5,018,519 B1 | 11/2000 | Brown |
| 6,165,105 A | 12/2000 | Boutellier et al. |
| 6,201,223 B1 | 3/2001 | Nitta |
| 6,272,933 B1 | 8/2001 | Gradon et al. |
| 6,305,372 B1 | 10/2001 | Servidio |
| 6,308,706 B1 | 10/2001 | Lammers et al. |
| 6,318,369 B1 | 11/2001 | Gregory |
| 6,332,463 B1 | 12/2001 | Farrugia et al. |
| 6,338,473 B1 | 1/2002 | Hebblewhite et al. |
| 6,349,722 B1 | 2/2002 | Gradon et al. |
| 6,363,930 B1 | 4/2002 | Clawson et al. |
| 6,367,474 B1 | 4/2002 | Berthon-Jones et al. |
| 6,394,084 B1 | 5/2002 | Nitta |
| 6,394,091 B1 | 5/2002 | Giorgini |
| 6,397,841 B1 | 6/2002 | Kenyon |
| 6,398,197 B1 | 6/2002 | Dickinson |
| 6,425,395 B1 | 7/2002 | Brewer et al. |
| 6,435,178 B1 | 8/2002 | Lin |
| 6,439,231 B1 | 8/2002 | Fukunaga et al. |

(56) References Cited

U.S. PATENT DOCUMENTS

| | | |
|---|---|---|
| 6,478,026 B1 | 11/2002 | Wood |
| 6,505,624 B1 | 1/2003 | Campbell, Sr. |
| 6,516,798 B1 | 2/2003 | Davies |
| 6,523,538 B1 | 2/2003 | Wikefeldt |
| 6,536,432 B2 | 3/2003 | Truschel |
| 6,536,436 B1 | 3/2003 | McGlothen |
| 6,543,449 B1 | 4/2003 | Woodring et al. |
| 6,550,476 B1 | 4/2003 | Ryder |
| 6,554,260 B1 | 4/2003 | Lipscombe et al. |
| 6,557,551 B2 | 5/2003 | Nitta |
| 6,561,193 B1 | 5/2003 | Noble |
| 6,571,794 B1 | 6/2003 | Hansen |
| 6,581,601 B2 | 6/2003 | Ziaee |
| 6,584,972 B2 | 7/2003 | McPhee |
| 6,584,977 B1 | 7/2003 | Serowski |
| 6,595,215 B2 | 7/2003 | Wood |
| 6,598,604 B1 | 7/2003 | Seakins |
| 6,629,531 B2 | 10/2003 | Gleason et al. |
| 6,662,802 B2 | 12/2003 | Smith |
| 6,668,828 B1 | 12/2003 | Figley et al. |
| 6,679,264 B1 | 1/2004 | Deem et al. |
| 6,679,265 B2 | 1/2004 | Strickland et al. |
| 6,694,974 B1 | 2/2004 | George-Gradon et al. |
| 6,733,556 B1 | 5/2004 | Luigi |
| 6,766,800 B2 | 7/2004 | Murdock et al. |
| 6,772,758 B2 | 8/2004 | Lambert |
| 6,772,999 B2 | 8/2004 | Lipscombe et al. |
| 6,776,158 B1 | 8/2004 | Anderson et al. |
| 6,802,314 B2 | 10/2004 | McPhee |
| 6,805,120 B1 | 10/2004 | Jeffrey et al. |
| 6,807,966 B2 | 10/2004 | Wright |
| 6,817,361 B2 | 11/2004 | Berthon-Jones |
| 6,851,425 B2 | 2/2005 | Jaffre et al. |
| 6,863,069 B2 | 3/2005 | Wood |
| 6,886,562 B2 | 5/2005 | Ishizuka |
| 6,899,102 B1 | 5/2005 | McGlothen |
| 6,918,389 B2 | 7/2005 | Seakins et al. |
| 6,921,417 B2 | 7/2005 | Persson et al. |
| 6,923,181 B2 | 8/2005 | Tuck |
| 6,935,337 B2 | 8/2005 | Virr et al. |
| 6,953,354 B2 | 10/2005 | Edirisuriya |
| 6,976,488 B2 | 12/2005 | Halperin |
| 6,986,353 B2 | 1/2006 | Wright |
| 6,990,977 B1 | 1/2006 | Calluaud |
| 6,994,089 B2 | 2/2006 | Wood |
| 6,997,177 B2 | 2/2006 | Wood |
| 7,004,162 B1 | 2/2006 | Foley et al. |
| 7,013,361 B2 | 3/2006 | Liron |
| 7,032,592 B2 | 4/2006 | Castor |
| 7,043,979 B2 | 5/2006 | Smith |
| 7,047,974 B2 | 5/2006 | Strickland et al. |
| 7,051,733 B2 | 5/2006 | Gradon et al. |
| 7,069,928 B1 | 7/2006 | Waldo, Jr. |
| 7,086,399 B2 | 8/2006 | Makinson et al. |
| 7,106,955 B2 | 9/2006 | Thudor et al. |
| 7,111,624 B2 | 9/2006 | Thudor et al. |
| 7,120,354 B2 | 10/2006 | Mackie et al. |
| 7,137,388 B2 | 11/2006 | Virr et al. |
| 7,137,389 B2 | 11/2006 | Berthon-Jones |
| 7,140,367 B2 | 11/2006 | White |
| 7,146,976 B2 | 12/2006 | McKown |
| 7,146,979 B2 | 12/2006 | Seakins et al. |
| 7,188,624 B2 | 3/2007 | Wood |
| 7,192,550 B2 | 3/2007 | Berger et al. |
| 7,225,811 B2 | 6/2007 | Ruiz et al. |
| RE39,724 E | 7/2007 | Gradon et al. |
| 7,237,770 B2 | 7/2007 | Lipscombe et al. |
| 7,263,994 B2 | 9/2007 | Gradon et al. |
| 7,270,128 B2 | 9/2007 | Berthon-Jones |
| 7,305,988 B2 | 12/2007 | Acker et al. |
| 7,306,205 B2 | 12/2007 | Huddart et al. |
| 7,396,995 B2 | 7/2008 | Laurent et al. |
| 7,406,966 B2 | 8/2008 | Wondka |
| 7,428,902 B2 | 9/2008 | Du et al. |
| 7,438,073 B2 | 10/2008 | Delache et al. |
| 7,469,698 B1 | 12/2008 | Childers |
| 7,481,222 B2 | 1/2009 | Reissmann |
| 7,487,774 B2 | 2/2009 | Acker |
| 7,493,902 B2 | 2/2009 | White et al. |
| 7,506,647 B2 | 3/2009 | Worthington |
| 7,525,663 B2 | 4/2009 | Kwok et al. |
| RE40,806 E | 6/2009 | Gradon et al. |
| 7,549,419 B2 | 6/2009 | Carlsen et al. |
| 7,568,482 B2 | 8/2009 | Jaffre et al. |
| 7,588,029 B2 | 9/2009 | Smith et al. |
| 7,594,509 B2 | 9/2009 | Burk |
| 7,614,398 B2 | 11/2009 | Virr et al. |
| 7,616,871 B2 | 11/2009 | Kramer |
| 7,624,731 B2 | 12/2009 | Walstrom |
| 7,634,998 B1 | 12/2009 | Fenley |
| 7,658,189 B2 | 2/2010 | Davidson et al. |
| 7,708,017 B2 | 5/2010 | Davidson et al. |
| 7,717,113 B2 | 5/2010 | Andrieux |
| 7,770,579 B2 | 8/2010 | O'Connor et al. |
| 7,798,148 B2 | 9/2010 | Doshi et al. |
| 7,806,120 B2 | 10/2010 | Loomas et al. |
| 7,849,852 B2 | 12/2010 | Bremner et al. |
| 7,856,979 B2 | 12/2010 | Doshi et al. |
| 7,870,857 B2 | 1/2011 | Dhuper et al. |
| 7,913,497 B2 | 3/2011 | Dickerson |
| 7,913,640 B2 | 3/2011 | MacDonald et al. |
| 7,926,485 B2 | 4/2011 | Nguyen et al. |
| 7,942,148 B2 | 5/2011 | Davidson et al. |
| 7,958,891 B2 | 6/2011 | Smith et al. |
| 7,962,018 B2 | 6/2011 | Hunt et al. |
| 7,987,847 B2 | 8/2011 | Wickham et al. |
| 7,987,852 B2 | 8/2011 | Doshi et al. |
| 7,992,564 B2 | 8/2011 | Doshi et al. |
| 7,997,270 B2 | 8/2011 | Meier |
| 8,006,691 B2 | 8/2011 | Kenyon et al. |
| 8,015,971 B2 | 9/2011 | Kwok |
| 8,020,551 B2 | 9/2011 | Virr et al. |
| RE42,843 E | 10/2011 | Strickland et al. |
| 8,028,693 B2 | 10/2011 | Trevor-Wilson et al. |
| 8,037,882 B2 | 10/2011 | Smith et al. |
| 8,042,535 B2 | 10/2011 | Kenyon et al. |
| 8,052,127 B2 | 11/2011 | Nichols et al. |
| 8,061,355 B2 | 11/2011 | Jaffre et al. |
| 8,061,357 B2 | 11/2011 | Pierce et al. |
| 8,069,854 B2 | 12/2011 | Colla et al. |
| 2002/0083947 A1 | 7/2002 | Seakins |
| 2003/0079748 A1 | 5/2003 | Seakins |
| 2003/0079751 A1 | 5/2003 | Kwok |
| 2004/0035431 A1 | 2/2004 | Wright |
| 2004/0065327 A1 | 4/2004 | Gradon et al. |
| 2004/0211421 A1 | 10/2004 | Blansfield |
| 2005/0011521 A1 | 1/2005 | Sprinkle et al. |
| 2005/0121038 A1 | 6/2005 | Christopher |
| 2005/0126573 A1 | 6/2005 | Jaffre et al. |
| 2005/0150505 A1 | 7/2005 | Burrow et al. |
| 2007/0056590 A1 | 3/2007 | Wolfson |
| 2007/0062534 A1 | 3/2007 | Fisher et al. |
| 2007/0079826 A1 | 4/2007 | Kramer et al. |
| 2007/0144518 A1 | 6/2007 | Acker et al. |
| 2007/0267023 A1 | 11/2007 | Ging et al. |
| 2007/0277825 A1 | 12/2007 | Bordewick et al. |
| 2008/0047560 A1 | 2/2008 | Veliss et al. |
| 2008/0060649 A1 | 3/2008 | Veliss et al. |
| 2008/0066745 A1 | 3/2008 | Janbakhsh et al. |
| 2008/0099013 A1 | 5/2008 | Graham |
| 2008/0105257 A1 | 5/2008 | Klasek et al. |
| 2008/0142015 A1 | 6/2008 | Groll |
| 2008/0156330 A1 | 7/2008 | Smith et al. |
| 2008/0190436 A1 | 8/2008 | Jaffe et al. |
| 2008/0223367 A1 | 9/2008 | Cox et al. |
| 2008/0257343 A1 | 10/2008 | Peterson |
| 2008/0302361 A1 | 12/2008 | Snow et al. |
| 2009/0000620 A1 | 1/2009 | Virr |
| 2009/0044808 A1 | 2/2009 | Guney et al. |
| 2009/0050153 A1 | 2/2009 | Brunner |
| 2009/0065005 A1 | 3/2009 | Ades |
| 2009/0065729 A1 | 3/2009 | Worboys et al. |
| 2009/0095295 A1 | 4/2009 | Wruck et al. |
| 2009/0114221 A1 | 5/2009 | Nagorny |

(56) References Cited

U.S. PATENT DOCUMENTS

| | | |
|---|---|---|
| 2009/0114229 A1 | 5/2009 | Frater et al. |
| 2009/0133700 A1 | 5/2009 | Martin |
| 2009/0151719 A1 | 6/2009 | Wondka et al. |
| 2009/0151728 A1 | 6/2009 | McConnell et al. |
| 2009/0174092 A1 | 7/2009 | Kwok |
| 2009/0194106 A1 | 8/2009 | Smith et al. |
| 2009/0223514 A1 | 9/2009 | Smith et al. |
| 2009/0229606 A1 | 9/2009 | Tang et al. |
| 2009/0241948 A1 | 10/2009 | Clancy et al. |
| 2009/0247967 A1 | 10/2009 | Delli Paoli, Jr. |
| 2009/0277448 A1 | 11/2009 | Ahlmen et al. |
| 2009/0277452 A1 | 11/2009 | Lubke et al. |
| 2009/0293881 A1 | 12/2009 | Graham |
| 2009/0301478 A1 | 12/2009 | Ohmura et al. |
| 2009/0320840 A1 | 12/2009 | Klasek et al. |
| 2010/0018534 A1 | 1/2010 | Veliss et al. |
| 2010/0043796 A1 | 2/2010 | Meynink et al. |
| 2010/0071693 A1 | 3/2010 | Allum et al. |
| 2010/0083965 A1 | 4/2010 | Virr et al. |
| 2010/0095966 A1 | 4/2010 | Dureus |
| 2010/0101575 A1 | 4/2010 | Fedorko et al. |
| 2010/0101584 A1 | 4/2010 | Bledstein et al. |
| 2010/0132717 A1 | 6/2010 | Davidson et al. |
| 2010/0147299 A1 | 6/2010 | Row et al. |
| 2010/0154796 A1 | 6/2010 | Smith et al. |
| 2010/0180895 A1 | 7/2010 | Kwok et al. |
| 2010/0206308 A1 | 8/2010 | Klasek et al. |
| 2010/0206312 A1 | 8/2010 | O'Leary |
| 2010/0236549 A1 | 9/2010 | Selvarajan et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0282247 A1 | 11/2010 | Kadrichu et al. |
| 2011/0017212 A1 | 1/2011 | Kenyon et al. |
| 2011/0023874 A1 | 2/2011 | Bath et al. |
| 2011/0023877 A1 | 2/2011 | Kenyon et al. |
| 2011/0030691 A1 | 2/2011 | Campbell |
| 2011/0067704 A1 | 3/2011 | Kooij et al. |
| 2011/0073111 A1 | 3/2011 | Stone et al. |
| 2011/0094518 A1 | 4/2011 | Cipollone et al. |
| 2011/0108036 A1 | 5/2011 | Thomas |
| 2011/0120462 A1 | 5/2011 | Tatkov et al. |
| 2011/0126834 A1 | 6/2011 | Winter et al. |
| 2011/0126835 A1 | 6/2011 | Winter et al. |
| 2011/0146685 A1 | 6/2011 | Allan et al. |
| 2011/0162647 A1 | 7/2011 | Huby et al. |
| 2011/0203595 A1 | 8/2011 | Hashemieh |
| 2011/0209709 A1 | 9/2011 | Davidson et al. |
| 2011/0214676 A1 | 9/2011 | Allum et al. |
| 2011/0247619 A1 | 10/2011 | Formica et al. |
| 2011/0253136 A1 | 10/2011 | Sweeney et al. |
| 2011/0265796 A1 | 11/2011 | Amarasinghe et al. |
| 2011/0283999 A2 | 11/2011 | Smith et al. |
| 2011/0297150 A1 | 12/2011 | Kwok |
| 2012/0325218 A1 | 12/2012 | Brambilla et al. |
| 2013/0000647 A1 | 1/2013 | Holley et al. |

FOREIGN PATENT DOCUMENTS

| | | |
|---|---|---|
| CA | 2193906 A1 | 6/1997 |
| CA | 2408983 A1 | 4/2003 |
| CH | 685678 A5 | 9/1995 |
| CN | 1878589 A | 12/2006 |
| CN | 2880043 Y | 3/2007 |
| CN | 101069764 A | 11/2007 |
| CN | 200995037 Y | 12/2007 |
| CN | 201123948 Y | 10/2008 |
| CN | 201161072 Y | 12/2008 |
| CN | 201239409 Y | 5/2009 |
| CN | 201249002 Y | 6/2009 |
| CN | 101474449 A | 7/2009 |
| CN | 201279335 Y | 7/2009 |
| CN | 201356075 Y | 12/2009 |
| CN | 101816466 A | 9/2010 |
| DE | 3829115 A1 | 3/1989 |
| DE | 4011873 A1 | 10/1990 |
| DE | 4434236 A1 | 3/1996 |
| DE | 69211011 T2 | 12/1996 |
| DE | 69724996 T2 | 7/2004 |
| DE | 60031249 T2 | 5/2007 |
| DE | 60215955 T2 | 6/2007 |
| DE | 60213427 T2 | 9/2007 |
| DE | 60213428 T2 | 3/2008 |
| DE | 20122844 U1 | 6/2008 |
| EP | 265163 A3 | 2/1989 |
| EP | 317417 A1 | 1/1992 |
| EP | 504977 A1 | 9/1992 |
| EP | 409402 B1 | 8/1993 |
| EP | 417026 A1 | 7/1994 |
| EP | 588214 B1 | 12/1998 |
| EP | 604399 B1 | 12/1998 |
| EP | 1005878 A2 | 6/2000 |
| EP | 686408 A2 | 8/2000 |
| EP | 1100591 B1 | 11/2004 |
| EP | 1314445 A1 | 9/2005 |
| EP | 1163923 A2 | 11/2005 |
| EP | 1629859 A1 | 3/2006 |
| EP | 1854494 A1 | 11/2007 |
| EP | 1042034 B1 | 2/2008 |
| EP | 1938856 A1 | 7/2008 |
| EP | 2039387 A8 | 11/2009 |
| EP | 2113275 A1 | 11/2009 |
| EP | 2229973 A3 | 11/2010 |
| EP | 2269681 A2 | 1/2011 |
| EP | 2272557 A2 | 1/2011 |
| EP | 2296740 A1 | 3/2011 |
| EP | 2301615 A1 | 3/2011 |
| FR | 2915106 A3 | 10/2008 |
| JP | 10248947 A | 9/1998 |
| JP | 2004215996 A | 8/2004 |
| JP | 2006289093 A | 10/2006 |
| JP | 2008113922 A | 5/2008 |
| JP | 2008136826 A | 6/2008 |
| JP | 2010264183 A | 11/2010 |
| RU | 2336907 C2 | 10/2008 |
| WO | 0195965 A1 | 12/2001 |
| WO | 2008113424 A1 | 9/2008 |
| WO | 2009118718 A1 | 10/2009 |
| WO | 2009127049 A1 | 10/2009 |
| WO | 2009149284 A1 | 12/2009 |
| WO | 2009149289 A1 | 12/2009 |
| WO | 2009149290 A1 | 12/2009 |
| WO | 2010044034 A1 | 4/2010 |
| WO | 2010044035 A1 | 4/2010 |
| WO | 2010044039 A2 | 4/2010 |
| WO | 2010096467 A1 | 8/2010 |
| WO | 2011029074 A1 | 3/2011 |

OTHER PUBLICATIONS

Long-Term Effects of Different Humidification Systems on Endotracheal Tube Patency: Evaluation by the Acoustic Reflection Method. Jaber S, Pigeot J, Fodil R, Maggiore S, Harf A, Isabey D, Brochard L, Louis B.

Multicenter Study Assessing Effects of Heat and Moisture Exchanger Use on Respiratory Symptoms and Voice Quality in Laryngectomized Individuals. Ackerstaff AH, Fuller D, Irvin M, Maccracken E, Gaziano J, Stachowiak L.

[Phoning Study About Postoperative Practice and Application of Non-Invasive Ventilation]. Chanques G, Jaber S, Delay JM, Perrigault PF, Lefrant JY, Eledjam JJ. Ann FF Anesth Reanim. Dec. 2003;22(10):879-85.

Sudden Complete Obstruction of Breathing Circuit During Postural Change Upon Completion of Thoracic Spinal Surgery in a Pediatric Patient. Wang YM, Chen CS, Chung NC, Ye XD, Liu K. Acta Anaesthesiol Sin. Sep. 2003;41(3):145-8.

Influence of the Humidification Device During Acute Respiratory Distress Syndrome. Prat G, Renault A, Tonnelier JM, Goetghebeur D, Oger E, Boles JM, L'Her E. Intensive Care Med. Dec. 2003;29(12):2211-5. Epub Aug. 6, 2003.

(56) References Cited

OTHER PUBLICATIONS

Mechanical Effects of Airway Humidification Devices in Difficult to Wean Patients. Girault C, Breton L, Richard JC, Tamion F, Vandelet P, Aboab J, Leroy J, Bonmarchand G. Crit Care Med. May 2003;31(5):1306-11.

A New Heat and Moisture Exchanger, Trach-Vent Plus, for Patients With Spontaneous Respiration]. Nishiyama T, Hanaoka K. Masui. Apr. 2003;52(4):417-9.

The Effect of Heat and Moisture Exchanger on Humidity and Body Temperature in a Low-Flow Anaesthesia System. Johansson A, Lundberg D, Luttropp HH. Acta Anaesthesiol Scand. May 2003;47(5):564-8.

A Study of the Effect of a Resistive Heat Moisture Exchanger (Trachinaze) on Pulmonary Function and Blood Gas Tensions in Patients Who Have Undergone a Laryngectomy: A Randomized Control Trial of 50 Patients Studied Over a 6-Month Period. Jones AS, Young PE, Hanafi ZB, Makura ZG, Fenton JE, Hughes JP.

The Effect of Heat and Moisture Exchanger and Gas Flow on Humidity and Temperature in a Circle Anaesthetic System. Poopalalingam R, Goh MH, Chan YW. Singapore Med J. Nov. 2002;43(11):563-5.

Long-Term Mechanical Ventilation With Hygroscopic Heat and Moisture Exchangers Used for 48 Hours: A Prospective Clinical, Hygrometric, and Bacteriologic Study. Boyer A, Thiéry G, Lasry S, Pigné E, Salah A, de Lassence A, Dreyfuss D, Ricard JD.

Heat and Moisture Exchangers in Mechanically Ventilated Intensive Care Unit Patients: A Plea for an Independent Assessment of Their Performance Thiéry G, Boyer A, Pigné E, Salah A, De Lassence A, Dreyfuss D, Ricard JD.

Development and Clinical Assessment of a Heat and Moisture Exchanger With a Multi-Magnet Automatic Tracheostoma Valve (Provox Freehands Hme) for Vocal and Pulmonary Rehabilitation After Total Laryngectomy. Hilgers FJ, Ackerstaff AH, Van As CJ, Balm AJ, Van den Brekel MW.

Ability and Safety of a Heated Humidifier to Control Hypercapnic Acidosis in Severe Ards. Prin S, Chergui K, Augarde R, Page B, Jardin F, Vieillard-Baron A. Intensive Care Med. Dec. 2002;28(12):1756-60. Epub Oct. 8, 2002.

Comparison of the Effects of Heat and Moisture Exchangers and Heated Humidifiers on Ventilation and Gas Exchange During Non-Invasive Ventilation. Jaber S, Chanques G, Matecki S, Ramonatxo M, Souche B, Perrigault PF, Eledjam JJ.

The Combination of a Heat and Moisture Exchanger and a Booster: A Clinical and Bacteriological Evaluation Over 96 H. Thomachot L, Viviand X, Boyadjiev I, Vialet R, Martin C. Intensive Care Med. Feb. 2002;28(2):147-53. Epub Jan. 12, 2002.

Efficiency and Safety of Mechanical Ventilation With a Heat and Moisture Exchanger Changed Once a Week. Paluch B. Am J Respir Crit Care Med. Nov. 15, 2001;164(10 Pt 1):1999-2000. 66 A Breathing Circuit Disconnection Detected by Anesthetic Agent Monitoring. Kennedy RR, French RA Can J Anaesth. Oct. 2001;48(9):847-9.

A Randomized Clinical Trial to Compare the Effects of a Heat and Moisture Exchanger With a Heated Humidifying System on the Occurrence Rate of Ventilator-Associated Pneumonia. Memish ZA, Oni GA, Djazmati W, Cunningham G, Mah MW. Am J Infect Control. Oct. 2001;29(5):301-5.

[Measurement of Water Vapour Pressure in the Airways of Mechanically Ventilated Patient Using Different Types of Humidifiers]. Rathgeber J, Betker T, Züchner K. Anasthesiol Intensivmed Notfallmed Schmerzther. Sep. 2001;36(9):560-5.

[Experience With the Hme-Provox Stomafilter in Laryngectomized Patients]. Herranz González-Botas J, Suárez T, García Carreira B, Martinez Morán A. Acta Otorrinolaringol Esp. Apr. 2001;52(3):221-5.

Air Flow Resistance of Three Heat and Moisture Exchanging Filter Designs Under Wet Conditions: Implications for Patient Safety. Morgan-Hughes NJ, Mills GH, Northwood D. Br J Anaesth. Aug. 2001;87(2):289-91.

A New Device to Reduce the Consumption of a Halogenated Anaesthetic Agent. Enlund M, Wiklund L, Lambert H. Anaesthesia. May 2001;56(5):429-32. Intensive Care Med. Jan. 2001;27(1):296-300.

Changing Patterns of Airway Accidents in Intubated Icu Patients. Kapadia FN, Bajan KB, Singh S, Mathew B, Nath A, Wadkar S. Intensive Care Med. Jan. 2001;27(1):296-300.

Retention of Airborne Latex Particles by a Bacterial and Viral Filter Used in Anaesthesia Apparatus. Barbara J, Chabane MH, Leynadier F, Girard F. Anaesthesia. Mar. 2001; 56(3):231-4.

Measurement of Tracheal Temperature Is Not a Reliable Index of Total Respiratory Heat Loss in Mechanically Ventilated Patients. Thomachot L, Viviand X, Lagier P, Dejode JM, Albanèse J, Martin C. Crit Care. 2001;5(1):24-30. Epub Dec. 8, 2000.

A Randomized, Controlled, Clinical Trial of a Chemically-Reactive Heated Humidifier. Broach SD, Durbin CG Jr. Respir Care. Jan. 2001;46(1):37-42.

Mechanical Effects of Heat-Moisture Exchangers in Ventilated Patients. Iotti GA, Olivei MC, Braschi A. Crit Care. 1999;3(5):R77-82. Epub Sep. 23, 1999.

A New Device for 100 Per Cent Humidification of Inspired Air. Larsson A, Gustafsson A, Svanborg L. Crit Care. 2000;4(1):54-60. Epub Jan. 24, 2000.

Technical Requirements for Buying a Heat and Humidity Exchanger for Ventilation During Anesthesia. French Society of Anesthesia and Intensive Care Hajjar J, Loctin H, Goullet D. Ann Fr Anesth Reanim. Aug. 2000;19(7):556-60.

The Effect of a Heat and Moisture Exchanger on Gas Flow in a Mapleson F Breathing System During Inhalational Induction. Da Fonseca JM, Wheeler DW, Pook JA. Anaesthesia. Jun. 2000;55(6):571-3.

Prolonged Use of Heat and Moisture Exchangers Does Not Affect Device Efficiency or Frequency Rate of Nosocomial Pneumonia. Davis K Jr, Evans SL, Campbell RS, Johannigman JA, Luchette FA, Porembka DT, Branson RD.

The Effects of Passive Humidifier Dead Space on Respiratory Variables in Paralyzed and Spontaneously Breathing Patients Campbell RS, Davis K Jr, Johannigman JA, Branson RD. Respir Care. Mar. 2000;45(3):306-12.

Effects of a Heat and Moisture Exchanger and a Heated Humidifier on Respiratory Mucus in Patients Undergoing Mechanical Ventilation. Nakagawa NK, Macchione M, Petrolino HM, Guimarães ET, King M, Saldiva PH, Lorenzi-Filho G.

Hypercapnia Due to a Heat and Moisture Exchanger. Briassoulis G, Paraschou D, Hatzis T. Intensive Care Med. Jan. 2000;26(1):147.

Changing a Hydrophobic Heat and Moisture Exchanger After 48 Hours Rather Than 24 Hours: A Clinical and Microbiological Evaluation. Boisson C, Viviand X, Arnaud S, Thomachot L, Miliani Y, Martin C. Intensive Care Med. Nov. 1999;25(11):1237-43.

Humidification Method That Decreases Condensate Contamination in Ventilator Tubing. Austan F, Suzukawa M. Heart Lung. Jan.-Feb. 2000;29(1):56-9.

Efficiency and Safety of Mechanical Ventilation With a Heat and Moisture Exchanger Changed Only Once a Week. Ricard JD, Le Mière E, Markowicz P, Lasry S, Saumon G, Djedaïni K, Coste F, Dreyfuss D.

Supplementary Oxygen and the Laryngeal Mask Airway—Evaluation of a Heat-and-Moisture Exchanger. Orme RM, Williams M. Anaesth Intensive Care. Oct. 1999;27(5):509-11.

Determination of Airway Humidification in High-Frequency Oscillatory Ventilation Using an Artificial Neonatal Lung Model. Comparison of a Heated Humidifier and a Heat and Moisture Exchanger. Schiffmann H, Singer S, Singer D, von Richthofen E, Rathgeber J, Züchner K.

Do the Components of Heat and Moisture Exchanger Filters Affect Their Humidifying Efficacy and the Incidence of Nosocomial Thomachot L, Vialet R, Arnaud S, Barberon B, Michel-Nguyen A, Martin C.

Changing Heat and Moisture Exchangers Every 48 Hours Does Not Increase the Incidence of Nosocomial Pneumonia. Daumal F, Colpart E, Manoury B, Mariani M, Daumal M. Infect Control Hosp Epidemiol. May 1999;20(5):347-9.

(56) References Cited

OTHER PUBLICATIONS

Critical Incident Involving a Heat and Moisture Exchanger With Attached Flexible Connector. Mansor M, Chan L. Anaesth Intensive Care. Feb. 1999;27(1):114-5.
[Prevention of Contamination With a Heat-and-Moisture-Exchanger (Hme) and Bacterial Filter During Clinical Anesthesia]. Shibata M, Asano M. Masui. Dec. 1998;47(12):1464-70.
The Influence of Stoma Occlusion on Aspects of Tracheoesophageal Voice. van As CJ, Hilgers FJ, Koopmansvan Beinum FJ, Ackerstaff AH. Acta Otolaryngol. Sep. 1998;118(5):732-8.
Preservation of Humidity and Heat of Respiratory Gases in Spontaneously Breathing, Tracheostomized Patients. Thomachot L, Viviand X, Arnaud S, Vialet R, Albanese J, Martin C. Acta Anaesthesiol Scand. Aug. 1998;42(7):841-4.
Humidification Practices in the Adult Intensive Care Unit, Prince of Wales Hospital. Lawrence JC. Respir Care Clin N Am. Jun. 1998;4(2):301-4.
Charcoal as an Airway Isoflurane Reflection Filter. Dahm SL, Steptoe P, Luttropp HH, Reinstrup P. Eur J Anaesthesiol. Mar. 1998;15(2):230-3.
Efficacy of Heat and Moisture Exchangers After Changing Every 48 Hours Rather Than 24 Hours Thomachot L, Vialet R, Viguier JM, Sidier B, Roulier P, Martin C. Crit Care Med. Mar. 1998;26(3):477-81.
Long-Term Compliance of Laryngectomized Patients With a Specialized Pulmonary Rehabilitation Device: Provox Stomafilter. Ackerstaff AH, Hilgers FJ, Balm AJ, Tan IB. Laryngoscope. Feb. 1998;108(2):257-60.
Airway Humidification in Mechanically Ventilated Neonates and Infants: A Comparative Study of a Heat and Moisture Exchanger Vs. a Heated Humidifier Using a New Fast-Response Capacitive Humidity Sensor Schiffmann H, Rathgeber J, Singer D, Harms K, Bolli A, ZUchner K.
Clinical Utility of Hygroscopic Heat and Moisture Exchangers in Intensive Care Patients. Boots RJ, Howe S, George N, Harris FM, Faoagali J. Crit Care Med. Oct. 1997;25(10):1707-12.
Correlation Between Simple Clinical Parameters and the In Vitro Humidification Characteristics of Filter Heat and Moisture Exchangers. Groupe De Travail Sur Les Respirateurs. Beydon L, Tong D, Jackson N, Dreyfuss D. Chest. Sep. 1997;112(3):739-44.
Prevention of Patient Bacterial Contamination of Anaesthesia-Circle-Systems: A Clinical Study of the Contamination Risk and Performance of Different Heat and Moisture Exchangers With Electret Filter (Hmef). Rathgeber J, Kietzmann D, Mergeryan H, Hub R, Züchner K.
Unfavorable Mechanical Effects of Heat and Moisture Exchangers in Ventilated Patients. Iotti GA, Olivei MC, Palo A, Galbusera C, Veronesi R, Comelli A, Brunner JX, Braschi A. Intensive Care Med. Apr. 1997;23(4):399-405.
Acute Intraoperative Endotracheal Tube Obstruction Associated With a Heat and Moisture Exchanger in an Infant. Casta A, Houck CS. Anesth Analg. Apr. 1997;84(4):939-40.
Safety of Combined Heat and Moisture Exchanger Filters in Long-Term Mechanical Ventilation. Hurni JM, Feihl F, Lazor R, Leuenberger P, Perret C. Chest. Mar. 1997;111(3):686-91.
Patient Ventilator Interfaces: Practical Aspects in the Chronic Situation. Clini E. Monaldi Arch Chest Dis. Feb. 1997;52(1):76-9.
The Effect of a Heat and Moisture Exchanger on Humidity in a Low-Flow Anaesthesia System. Henriksson BA, Sundling J, Hellman.
Anaesthesia. Feb. 1997;52(2):144-9 108 [Artificial Humidification of Inspired Gas—Status of Knowledge and Technique]. Henze D, Menzel M, Radke J. Anaesthesiol Reanim. 1997;22(6):153-8. 109 The Benefit of Using a Heat and Moisture Exchanger During Short Operations in Young Children. Monrigal JP, Granry JC. Paediatr Anaesth. 1997;7(4):295-300.
Remarks on the Work of J. Rathgeber Et Al. Respiratory Gas Acclimatization With an Efficient Hme (Heat and Moisture Exchanger)—An Effective and Cost Saving Alternative to Active Humidifying of the Ventilated Patient. Anaesthesist (1996) 45: 518-525 Thäle H, Hares W. Anaesthesist. Dec. 1996;45(12):1270-2.
Gradual Reduction of Endotracheal Tube Diameter During Mechanical Ventilation via Different Humidification Devices. Villafane MC, Cinnella G, Lofaso F, Isabey D, Hart A, Lemaire F, Brochard L.
The Effect of Convection Warming During Abdominal Surgery on the Early Postoperative Heat Balance]. Kaudasch G, Schempp P, Skierski P, Turner E. Anaesthesist. Nov. 1996;45(11):1075-81.
A New Heat and Moisture Exchanger With Speech Valve (Provox Stomafilter). Hilgers FJ, Ackerstaff AH, Balm AJ, Gregor RT. Clin Otolaryngol Allied Sci. Oct. 1996;21(5):414-8.
[The Effect of a Heat and Moisture Exchanger (Hme) on Bronchial Mucus Transport in a Closed Inhalation Anesthesia System]. Konrad F, Mezödy M, Goertz A, Marx T, Georgieff M. Anaesthesist. Sep. 1996;45(9):802-6.
Failure of Ventilation in an Infant Due to Increased Resistance of a Disposable Heat and Moisture Exchanger. Barnes SD, Normoyle DA. Anesth Analg. Jul. 1996;83(1):193.
[Air Conditioning With a High-Performance Hme (Heat and Moisture Exchanger)—An Effective and Economical Alternative to Active Humidifiers in Ventilated Patients. A Prospective and Randomized Clinical Study]. Rathgeber J, Henze D, Züchner K. Anaesthesist. Jun. 1996;45(6):518-25.
Monitoring Body-Core Temperature From the Trachea: Comparison Between Pulmonary Artery, Tympanic, Esophageal, and Rectal Temperatures. Hayes JK, Collette DJ, Peters JL, Smith KW. J Clin Monit. May 1996;12(3):261-9.
Control of Body Temperature During Abdominal Aortic Surgery. Gregorini P, Cangini D. Acta Anaesthesiol Scand. Feb. 1996;40(2):187-90.
[Microbiological Studies of a Nasal Positive Pressure Respirator With and Without a Humidifier System]. Hetzel J, Herb S, Hetzel M, Rusteberg T, Kleiser G, Weber J, Kochs M, Hombach V. Wien Med Wochenschr. 1996;146(13-14):354-6.
Heat and Moisture Exchangers as a Treatment Option in the Post-Operative Rehabilitation of Laryngectomized Patients. Ackerstaff AH, Hilgers FJ, Aaronson NK, De Boer MF, Meeuwis CA, Knegt PP, Spoelstra HA, Van.
Shivering and Rewarming After Cardiac Surgery: Comparison of Ventilator Circuits With Humidifier and Heated Wires to Heat and Moisture Exhangers. McEvoy MT, Carey TJ. Am J Crit Care. Jul. 1995;4(4):293-9.
A Hazardous Modification of a Heat and Moisture Exchanger Ferguson AJ, Orr DA. Anaesthesia. May 1995;50(5):479.
Inhalation Rewarming From Hypothermia: An Evaluation in -20 Degrees C Simulated Field Conditions Mekjavi_IB, Eiken O. Aviat Space Environ Med. May 1995;66(5):424-9.
Mechanical Ventilation With Heated Humidifiers or Heat and Moisture Exchangers: Effects on Patient Colonization and Incidence of Nosocomial Pneumonia. Dreyfuss D, Djedaïni K, Gros I, Mier L, Le Bourdellés G, Cohen Y, Estagnasié P, Coste F, Boussougant.
Preservation of Humidity and Heat of Respiratory Gases in Patients With a Minute Ventilation Greater Than 10 L/Min Martin C, Papazian L, Perrin G, Saux P, Gouin F. Crit Care Med. Nov. 1994;22(11):1871-6.
Bair Hugger Forced-Air Warming Maintains Normothermia More Effectively Than Thermo-Lite Insulation. Borms SF, Engelen SL, Himpe DG, Suy MR, Theunissen WJ. J Clin Anesth. Jul.-Aug. 1994;6(4):303-7.
Improvements in Respiratory and Psychosocial Functioning Following Total Laryngectomy by the Use of a Heat and Moisture Exchanger Ackerstaff AH, Hilgers FJ, Aaronson NK, Balm AJ, van Zandwijk N. Ann Otol Rhinol Laryngol. Nov. 1993;102(11):878-83.
Oesophageal Thermal Tube for Intraoperative Hypothermia in Liver Transplantation. Steib A, Beller JP, von Bandel M, Beck F, Chabrol JL, Otteni JC. Acta Anaesthesiol Scand. Feb. 1993;37(2):199-202.
Performance of a Hydrophobic Heat and Moisture Exchanger at Different Ambient Temperatures. Croci M, Elena A, Solca M. Intensive Care Med. 1993;19(6):351-2.
An Active Heat and Moisture Exchanger. Kapadia F, Shelly MP, Anthony JM, Park GR. Br J Anaesth. Dec. 1992;69(6):640-2.

(56) References Cited

OTHER PUBLICATIONS

Effects of Surgical Site and Inspired Gas Warming Devices on Body Temperature During Lower Abdominal and Thoracic Surgery. Harioka T, Sone T, Nomura K, Kakuyama M. J Anesth. Oct. 1992;6(4):467-73.
Heat and Moisture Exchangers With Bacterial Filters: A Laboratory Evaluation. Mebius C. Acta Anaesthesiol Scand. Aug. 1992;36(6):572-6.
[Are Humidity Filters Necessary in the Inspired Air in the Breathing Circuit? A New In Vivo Method of Measuring Humidity in the Air Breathed] Kohler P, Rimek A, Albrecht M, Frankenberger H, Merlins W, van Ackern K.
[Is the Lithium Chloride-Coated Heat and Moisture Exchanger a Danger for Patients?]. Rathgeber J, Zielmann S, Kietzmann D, Züchner K, Warnecke G. Anaesthesist. Apr. 1992;41(4):204-7.
Disablement of a Ventilator Disconnect Alarm by a Heat and Moisture Exchanger. Milligan KA. Anaesthesia. Mar. 1992;47(3):279.
Comparison of Hydrophobic Heat and Moisture Exchangers With Heated Humidifier During Prolonged Mechanical Ventilation. Roustan JP, Kienlen J, Aubas P, Aubas S, du Cailar J. Intensive Care Med. 1992;18(2):97-100.
Do Heated Humidifiers and Heat and Moisture Exchangers Prevent Temperature Drop During Lower Abdominal Surgery? Goldberg ME, Epstein R, Rosenblum F, Larijani GE, Marr A, Lessin J, Torjman M, Seltzer J.
Effect of a Passive Heat and Moisture Exchanger on Esophageal Temperature in Tumor-Bearing Dogs During Whole-Body Hyperthermia Meyer RE, Page RL, Thrall DE. Am J Vet Res. Oct. 1991;52(10):1688-91.
Heat and Moisture Exchanger Vs Heated Humidifier During Long-Term Mechanical Ventilation. A Prospective Randomized Study. Misset B, Escudier B, Rivara D, Leclercq B, Nitenberg G. Chest. Jul. 1991;100(1):160-3.
[Treatment of Primary and Secondary Therapy Failure in Patients With Sleep Apnea Treated With Nasal Cpap]. Becker H, Fett I, Nees E, Peter JH, von Wichert P. Pneumologie. May 1991;45 Suppl 1:301-5.
Mucociliary Transport With and Without the Use of a Heat and Moisture Exchanger. An Animal Study. The importance to mucociliary transport (MCT) and the condition of the mucus of using a heat and Acta Anaesthesiol Scand. May 1991;35(4):297-301.
The Influence of a Heat and Moisture Exchanger (Hme) on the Respiratory Symptoms After Total Laryngectomy. Hilgers FJ, Aaronson NK, Ackerstaff AH, Schouwenburg PF, van Zandwikj N.
[The Use of an Artificial Nose (Hme: Heat-Moisture Exchanger) in Controlled Ventilation]. Sottiaux T. Rev Med Liege. Apr. 1991;46(4):204-12.
Assessment of a Hygroscopic Heat and Moisture Exchanger for Paediatric Use. Wilkinson KA, Cranston A, Hatch DJ, Fletcher ME. Assessment of a hygroscopic heat and moisture exch . . . [Anaesthesia. 1991]—PubMed result.
[Changes in Ventilation During Use of Heat and Humidity Exchangers]. Croci M, Corrado F, Sibilla E, Tiby A, Vercesi G, Proietti D, Vannucci A. Minerva Anestesiol. Jan.-Feb. 1999;57(1-2):13-6.
Physical and Psychosocial Sequelae of Total Larynx Extirpation and the Use of a Heat and Moisture Exchanger]. Ackerstaff AH, Hilgers FJ, Aaronson NK, Schouwenburg PF, van Zandwijk N.
Inhalation Rewarming From Hypothermia: An Evaluation in -20 Degrees C Simulated Field Conditions. Mekjavi_IB, Eiken O. Aviat Space Environ Med. May 1995;66(5):424-9.
Mechanical Ventilation With Heated Humidifiers or Heat and Moisture Exchangers: Effects on Patient Colonization and Incidence of Nosocomial Pneumonia. Dreyfuss D, Djedïni K, Gros I, Mier L, Le Bourdellés G, Cohen Y, Estagnasié P, Coste F, Boussougant.
Preservation of Humidity and Heat of Respiratory Gases in Patients With a Minute Ventilation Greater Than 10 L/Min. Martin C, Papazian L, Perrin G, Saux P, Gouin F. Crit Care Med. Nov. 1994;22(11):1871-6.

Oesophageal Thermal Tube for Intraoperative Hypothermia in Liver Transplantation Steib A, Beller JP, von Bandel M, Beck F, Chabrol JL, Otteni JC. Acta Anaesthesiol Scand. Feb. 1993;37(2):199-202.
Effects of Surgical Site and Inspired Gas Warming Devices on Body Temperature During Lower Abdominal and Thoracic Surgery. Harioka T, Stone T, Nomura K, Kakuyama M. J Anesth. Oct. 1992;6(4):467-73.
Use of a Heat and Moisture Exchanger During Long-Term Mechanical Ventilation. Sottiaux T. Chest. Sep. 1992;102(3):979-80.
The Use of an Artificial Nose (Hme: Heat-Moisture Exchanger) in Controlled Ventilation]. Sottiaux T. Rev Med Liege. Apr. 1991;46(4):204-12.
[Changes in Ventilation During Use of Heat and Humidity Exchangers]. Croci M, Corrado F, Sibilla E, Tiby A, Vercesi G, Proietti D, Vannucci A. Minerva Anestesiol. Jan.-Feb. 1991;57(1-2):13-6.
[Physical and Psychosocial Sequelae of Total Larynx Extirpation and the Use of a Heat and Moisture Exchanger]. Ackerstaff AH, Hilgers FJ, Aaronson NK, Schouwenburg PF, van Zandwijk N.
[Experimental Evaluation of a Prototype of Absolute Antibacterial Filter as a Moisture and Heat Exchanger]. Elena A, Solca M, Croci M, Noto A. Minerva Anestesiol. Oct. 1990;56(10):1253-4.
[Anesthetic Management of a Patient With Sjögren'S Syndrome and Pulmonary Fibrosis]. Takahashi S, Ogasawara H, Tsubo T, Ishihara H, Matsuki A. Masui. Oct. 1990;39(10):1393-6.
Heat and Moisture Exchangers and the Body Temperature: A Peroperative Study Eckerbom B, Lindholm CE. Acta Anaesthesiol Scand. Oct. 1990;34(7):538-42.
Maintenance of Body Temperature in Elderly Patients Who Have Joint Replacement Surgery. A Comparison Between the Heat and Moisture Exchanger and Heated Humidifier Yam PC, Carli F. Anaesthesia. Jul. 1990;45(7):563-5.
Complications Related to the Use of a Heat and Moisture Exchanger. Prasad KK, Chen L. Anesthesiology. May 1990;72(5):958.
153 Passive Warming of Airway Gases (Artificial Nose) Improves Accuracy of Esophageal Temperature Monitoring. Siegel MN, Gravenstein N. J Clin Monit. Apr. 1990;6(2):89-92.
Heat and Moisture Exchangers and Vaporizing Humidifiers in the Intensive Care Unit. Martin C, Perrin G, Gevaudan MJ, Saux P, Gouin F. Chest. Jan. 1990;97(1):144-9.
Bacterial Contamination and Frequency of Changing Ventilator Circuitry. Cadwallader HL, Bradley CR, Ayliffe GA J Hosp Infect Jan. 1990;15(1):65-72.
Passive or Active Inspired Gas Humidification Increases Thermal Steady-State Temperatures in Anesthetized Infants. Bissonnette B, Sessler DI. Anesth Analg. Dec. 1989;69(6):783-7.
A Dangerous Defect in a Heat and Moisture Exchanger. Prados W. Anesthesiology. Nov. 1989;71(5):804.
Tracheal Tube Biofilm as a Source of Bacterial Colonization of the Lung. Inglis TJ, Millar MR, Jones JG, Robinson DA. J Clin Microbiol. Sep. 1989;27(9):2014-8.
Passive and Active Inspired Gas Humidification in Infants and Children. Bissonnette B, Sessler DI, LaFlamme P Anesthesiology. Sep. 1989;71(3):350-4.
Failure of a Heat and Moisture Exchanger as a Cause of Disconnection During Anaesthesia. Bengtsson M, Johnson A. Acta Anaesthesiol Scand. Aug. 1989;33(6):522-3.
Intraoperative Temperature Monitoring Sites in Infants and Children and the Effect of Inspired Gas Warming on Esophageal Temperature Bissonnette B, Sessler DI, LaFlamme P. Anesth Analg. Aug. 1989;69(2):192-6.
Physiological Effects of a Mouth-Borne Heat Exchanger During Heavy Exercise in a Cold Environment. Eiken O, Kaiser P, Holmér I, Baer R. Ergonomics. Jun. 1989;32(6):645-53.
Study of Humidification Potential of a Heat and Moisture Exchanger in Tracheotomized Dogs. Myer CM 3rd, McDonald JS, Hubbell RN, Stith J. Ann Otol Rhinol Laryngol. May-Jun. 1988;97(3 Pt 1):322-5.
Endotracheal Tube Occlusion Associated With the Use of Heat and Moisture Exchangers in the Intensive Care Unit. Cohen IL, Weinberg PF, Fein IA, Rowinski GS. Crit Care Med. Mar. 1988;16(3):277-9.
The Heat and Moisture Exchanger Does Not Preserve Body Temperature or Reduce Recovery Time in Outpatients Undergoing Surgery and Anesthesia. Goldberg ME, Jan R, Gregg CE, Berko R, Marr AT, Larijani GE. Anesthesiology. Jan. 1988;68(1):122-3.

(56) References Cited

OTHER PUBLICATIONS

Effectiveness of a Heat and Moisture Exchanger in Preventing Hyperpnoea Induced Bronchoconstriction in Subjects With Asthma. Gravelyn TR, Capper M, Eschenbacher WL. Thorax. Nov. 1987;42(11):877-80.

An Evaluation of Six Disposable Heat and Moisture Exchangers. Turtle MJ, Ilsley AH, Rutten AJ, Runciman WB. Anaesth Intensive Care. Aug. 1987;15(3):317-22.

Contamination Control in Long-Term Ventilation. A Clinical Study Using a Heat- and Moisture-Exchanging Filter. Gallagher J, Strangeways JE, Allt-Graham J. Anaesthesia. May 1987;42(5):476-81.

Effects of a Heat and Moisture Exchanger on Carbon Dioxide Equilibrium During Mechanical Ventilation With the Bain Circuit. Romano E, Gullo A, Vacri A, Bonifacio R, Caristi D. Eur J Anaesthesiol. May 1987;4(3):183-6.

The Heat and Moisture Exchanger in Post-Tracheotomy Care. Myer CM 3rd. Otolaryngol Head Neck Surg. Feb. 1987;96(2):209-10.

Moistening of Inspired Air During Respirator Treatment. Comparison Between the Water-Bath Evaporator and Hygroscopic Moisture Heat Exchanger]. Kirkegaard L, Andersen BN, Jensen S. Ugeskr Laeger. Jan. 12, 1987;149(3):152-5.

Portable Lung Ventilators: The Potential Risk From Bacterial Colonisation. Shelly MP, Park GR, Warren RE, Whetstone RJ. Intensive Care Med. 1986;12(4):328-31.

Heated Humidification in Major Abdominal Surgery. Linko K, Honkavaara P, Nieminen MT. Eur J Anaesthesiol. Sep. 1984;1(3):285-91.

The Pall Ultipor Breathing Circuit Filter—An Efficient Heat and Moisture Exchanger. Chalon J, Markham JP, Ali MM, Ramanathan S, Turndorf H Anesth Analg. Jun. 1984;63(6):566-70.

The Hygroscopic Condenser Humidifier. A New Device for General Use in Anaesthesia and Intensive Care. Gedeon A, Mebius C. Anaesthesia. Nov.-Dec. 1979;34(10):1043-7.

The Foam Nose—A New Disposable Heat and Moisture Exchanger. A Comparison With Other Similar Devices. Revenäs B, Lindholm CE. Acta Anaesthesiol Scand. Feb. 1979;23(1):34-9.

A Disposable Condenser Humidifier for Use During Anaesthesia. Steward DJ. Can Anaesth Soc J. Mar. 1976;23(2):191-5.

Effects of Dry Air and Subsequent Humidification on Tracheal Mucous Velocity in Dogs. Hirsch JA, Tokayer JL, Robinson MJ, Sackner MA. J Appl Physiol. Aug. 1975;39(2):242-6.

A Reappraisal of the Multiple Gauze Heat and Moisture Exchanger. Shanks CA, Sara CA. Anaesth Intensive Care. Aug. 1973;1(5):428-32.

The Resistance to Airflow Caused by Heat and Moisture Exchanger and by Artificial Airways. Heinonen J, Poppius H. Ann Chir Gynaecol Fenn. 1969;58(1):32-5.

Heat and Moisture Exchanger as a Potential Cause of Undue Resistance to Breathing. Heinonen J, Ertama P, Poppius H. Ann Chir Gynaecol Fenn. 1969;58(2):176-9.

A Heat-and-Moisture Exchanger for Posttracheotomy Care. An Experimental Study. Toremalm NG. Acta Otolaryngol. Nov.-Dec. 1960;52:461-72.

Ecogeographic Variation in Human Nasal Passages. Yokley TR. Am J Phys Anthropol. Jan. 2009;138(1):11-22.

Performance of Breathing Filters Under Wet Conditions: A Laboratory Evaluation. Turnbull D, Fisher PC, Mills GH, Morgan-Hughes NJ. Br J Anaesth. May 2005;94(5):675-82. Epub Feb. 25, 2005.

Comparison of the Effects of Heat and Moisture Exchangers and Heated Humidifiers on Ventilation and Gas Exchange During Weaning Trials From Mechanical Ventilation Le Bourdellès G, Mier L, Fiquet B, Djedaïni K, Saumon G, Coste F, Dreyfuss D.

Heat and Moisture Exchangers. Structure and Function. Wilkes AR. Respir Care Clin N Am. Jun. 1998;4(2):261-79.

[Effect of a Heat and Humidity Exchanger (Humid-Vent-Mini) on the Carbon Dioxide Washout Effect of a Neonatal Ventilation Model]. Nikischin W. Monatsschr Kinderheilkd. Sep. 1990;138(9):593-5.

[Humidification of the Respiratory Tract in Anaesthesia]. d'Athis F, de la Coussaye JE. Ann Fr Anesth Reanim. 1988;7(5):393-400.

Effect of Heat and Moisture Exchanger (Hme) Positioning on Inspiratory Gas Humidification Daisuke Inui , Jun Oto and Masaji Nishimura BMC Pulmonary Medicine 2006, 6:19.

Total Laryngectomee Rehabilitation and Hmes na http://www.webwhispers.org/library/HMEHeatMoistureExchange.asp.

Equipment Review: Mechanical Effects of Heat-Moisture Exchangers in Ventilated Patients Giorgio A lotti,1 Maddalena C Olivei,2 and Antonio Braschi Crit Care. 1999; 3(5): R77-R82.

Heat Moisture Exchanger NA http://www.nextag.com/heat-moisture-exchanger/products-html.

Heat and Moisture Exchangers (Hme) NA http://www.gehealthcare.com/euen/anesthesia/products/airway-managementaccesories-supplies/heat-moisture-exchangers/index.html.

Heat and Moisture Exchange Devices: Are They Doing What They Are Supposed to Do? Harry J. M. Lemmens, MD PhD and John G. Brock-Utne, Md PhD http://www.anesthesia-analgesia.org/content/98/2/382.full.

Heat Moisture Exchanger (Hme)—Adult NA http://www.gvs.it/flex/cm/pages/ServeBLOB.php/L/UK/IDPagina/211.

Kimberly-Clark Ballard Heat and Moisture Exchangers and Filters NA http://vap.kchealthcare.com/media/62902/product%20literature_hme%20and%20moisture%20exchangers%20and%20filters_pdf.

Intersurgical Heat and Moisture Exchangers Na http://www.intersurgical.com/products/heat-and-moisture-exchangers.

Smiths Medical Filtered Heat Moisture Exchanger 1 Ea NA http://namireto.info/smiths-medical-filtered-heat-moisture-exchanger-1-ea.asp.

Ningbo Tianhou Import and Export Co., Ltd NA http://www.tenhoomed.com/products/Heat-Moisture-Exchanger-284977.html.

Thermotrach Heat & Moisture Exchanger NA http://www.flexicare.com/en/products/breathing-filters/thermotrach-heat--moistureexchanger.aspx.

A-M System NA http://www.a-msystems.com/p-21-heat-and-moisture-exchange-hme-filter.aspx.

Smiths Medical NA http://www.smiths-medical.com/catalog/humidification-systems/passive-humidificationsystems/thermovent-heat-moisture-exchangers1/quot-thermovent-t-quot.html.

Filter Heat Moisture Exchanger Hme, Flexlife 15F/15M, 1 Ea NA http://www.imed.com/p/Filter-Heat-Moisture-Exchanger-HME-Flexlife-15f-15m-1-ea/165277.html?utm_source=sas&utm_medium=aff&utm_campaign=product&zmam=1000941&zmas=21&zmac=180&zmap=165277.

Ballard Medical Products Ballard Flex Heat Moisture Exchange With Filter Blue 1 Ea NA http://halfusab.info/ballard-medical-products-ballard-flex-heat-moisture-exchange-withfilter-blue-1-ea.aspx.

Pharma Systems NA http://www.pharmasystems-ps.com/en/products/heat-and-moisturesexchangers/pharma-neo This is no Longer an Active Link.

Medicomp NA http://medicompmedical.com/filters.html This is no Longer an Active Link.

Heat and Moisture Exchange Devices: Are They Doing What They Are Supposed to Do? Lemmens HJ, Brock-Utne JG. Anesth Analg. Feb. 2004;98(2):382-5, table of contents.

The Effects of the Heat and Moisture Exchanger on Humidity, Airway Temperature, and Core Body Temperature Mary A. Delventhal; http://www.stormingmedia.us/21/2121/A212124.html.

Grea Medical Supplies NA http://www.greatmedicalsupplies.com/supply~Smiths+Medical+-+Portex+(SF)~thermovent-tportex-heatmoisture-exchange-50ca-570016.htm Unable to Retrieve This Page.

PCT Search Report and Written Opinion for PCT/US2012/43006, issued Oct. 23, 2012.

PCT Search Report and Written Opinion for PCT/US2012/43011, issued Sep. 25, 2012.

Position of Exhalation Port and Mask Design Affect Co2 Rebreathing During Noninvasive Positive Pressure Ventilation Schettino GP, Chatmongkolchart S, Hess DR, Kacmarek RM. Crit Care Med. Aug. 2003;31(8):2178-82.

Mechanical Ventilation of the Surgical Patient Thomas W Shields General Thoracic Surgery, Chapter 42, p. 585.

(56) References Cited

OTHER PUBLICATIONS

A Randomized Study of Out-of-Hospital Continuous Positive Airway Pressure for Acute Cardiogenic Pulmonary Oedema: Physiological and Clinical Effects Plaisance P, Pirracchio R, Berton C, Vicaut E, Payen D. Eur Heart J. Dec. 2007;28(23):2895-901. Epub Oct. 29, 2007.
ComfortFusion.
Active Exhalation Valve Control: Evaluation of Its Performance in Expiratory Resistance and Pressure Release John Newhart CRT; Chi-Yuan Chuang.
Evita 2 Intensive Care Ventilator.
The Effects of Two Kinds of Mask (With or Without Exhaust Valve) on Clothing Microclimates Inside the Mask in Participants Wearing Protective Clothing for Spraying Pesticides Hayashi C, Tokura H. Int Arch Occup Environ Health. Jan. 2004;77(1):73-8. Epub Aug. 30, 2003.
Evaluation on Masks With Exhaust Valves and With Exhaust Holes From Physiological and Subjective Responses Guo YP, Yi L, Tokura H, Wong TK, Chung JW, Gohel MD, Leung PH, Newton E. J Physiol Anthropol. Mar. 2008;27(2):93-102.
Effect of a Nonrebreathing Exhalation Valve on Long-Term Nasal Ventilation Using a Bilevel Device Hill NS, Carlisle C, Kramer NR. Chest. Jul. 2002;122(1):84-91.
Facial or Nasal Mask Pressure Support Ventilation in Managing Acute Exacerbation of Chronic Respiratory Failure in Chronic Obstructive Pulmonary Diseases Chen RC. Zhonghua Jie He He Hu Xi Za Zhi. Oct. 1992;15(5):285-7, 319.
Sleep and Neuromuscular Disease: Bilevel Positive Airway Pressure by Nasal Mask as a Treatment for Sleep Disordered Breathing in Patients With Neuromuscular Disease Guilleminault C, Philip P, Robinson A. J Neurol Neurosurg Psychiatry. Aug. 1998;65(2):225-32.
Nocturnal Assisted Ventilation Using Bilevel Positive Airway Pressure: The Effect of Expiratory Positive Airway Pressure Elliott MW, Simonds AK. Eur Respir J. Mar. 1995;8(3):436-40.
Effect of Nasal Valve Dilation on Effective Cpap Level in Obstructive Sleep Apnea Schönhofer B, Kerl J, Suchi S, Kohler D, Franklin KA. Respir Med. Sep. 2003;97(9):1001-5.
Continuous Positive Airway Pressure: New Generations Roux FJ, Hilbert J. Clin Chest Med. Jun. 2003;24(2):315-42.
A Sleep Laboratory Evaluation of an Automatic Positive Airway Pressure System for Treatment of Obstructive Sleep Apnea Behbehani K, Yen FC, Lucas EA, Burk JR. Sleep. Aug. 1, 1998;21(5):485-91.
CPAP via Nasal Mask: A Treatment for Occlusive Sleep Apnea Sanders MH, Moore SE, Eveslage J. Chest Jan. 1983;83(1):144-5.
CPAP Therapy Via Oronasal Mask for Obstructive Sleep Apnea Sanders MH, Kern NB, Stiller RA, Strollo PJ Jr, Martin TJ, Atwood CW Jr. Chest. Sep. 1994;106(3):774-9.
Nasal Continuous Positive Airway Pressure and Noninvasive Positive Ventilation in the Treatment of Sleep Apnea/Hypopnea Syndrome Ohi M, Tachibana N, Taniguchi M. Nippon Rinsho. Aug. 2000;58(8):1675-9.
The Nasal Valve: A Rhinomanometric Evaluation of Maximum Nasal Inspiratory Flow and Pressure Curves Santiago-Diez de Bonilla J, McCaffrey TV, Kern EB. Ann Otol Rhinol Laryngol. May-Jun. 1986;95(3 Pt 1):229-32.
The Four Components of the Nasal Valve Cole P Am J Rhinol. Mar.-Apr. 2003;17(2):107-10.
Oral Continuous Positive Airway Pressure for Sleep Apnea: Effectiveness, Patient Preference, and Adherence Beecroft J, Zanon S, Lukic D, Hanly P. Chest. Dec. 2003;124(6):2200-8.
Oral Appliance Therapy for Obstructive Sleep Apnea Ng A, Gotsopoulos H, Darendeliler AM, Cistulli PA. Treat Respir Med. 2005;4(6):409-22.
Potential Rebreathing After Continuous Positive Airway Pressure Failure During Sleep Farré R, Montserrat JM, Ballester E, Navajas D. Chest. Jan. 2002;121(1):196-200.
Continuous Positive Airway Pressure Therapy Improves Cardiovascular Autonomic Function for Persons With Sleep-Disordered Breathing Maser RE, Lenhard MJ, Rizzo AA, Vasile AA. Chest. Jan. 2008;133(1):86-91. Epub Oct. 20, 2007.
Analysis of Expiratory Pressure Reduction (C-Flex method) During CPAP Therapy Rühle KH, Domanski U, Happel A, Nilius G. Pneumologie. Feb. 2007;61(2):86-9.
Efficacy and Patient Satisfaction With Autoadjusting CPAP With Variable Expiratory Pressure Vs Standard CPAP: A Two-Night Randomized Crossover Trial Mulgrew AT, Cheema R, Fleetham J, Ryan CF, Ayas NT. Sleep Breath. Mar. 2007;11(1):31-7.
Nasal CPAP Therapy of Obstructive Sleep Apnea Syndrome With Expiratory Pressure Reduction: A Prospective Randomized Study of Acceptance of Treatment During Therapy Initiation Ficker JH, Müller D, Wiest G, Lehnert G, Dertinger SH, Katalinic A, Hahn EG. Pneumologie. Jun. 1997;51(6):586-91.
Dynamics of Pressure and Flow Curves of Various Expiratory Pressure Valves Raschke F, Fischer J. Med Klin (Munich). Apr. 28, 1997;92 Suppl 1:82-4.
Continuous Positive Airway Pressure (CPAP)—Does the Equipment Live Up to Its Name? Christensen EF, Nørregaard OF, Anker-Møller E, Spangsberg NL, Petersen KD, Schønemann NK. Ugeskr Laeger. May 25, 1992;154(22):1568-71.
Jet Flow-Regulated Expiratory Resistance to Maintain Constant CPAP During the Entire Respiratory Phase Nishimura M, Takezawa J, Imanaka H, Taenaka N, Yoshiya I. Chest. Apr. 1989;95(4):876-80.
Effects of Expiratory Flow Resistance on Inspiratory Work of Breathing Banner MJ, Downs JB, Kirby RR, Smith RA, Boysen PG, Lampotang S. Chest. Apr. 1988;93(4):795-9.
Augmented Spontaneous Breathing Hachenberg T. Anaesthesist. Sep. 1996;45(9):839-55.
Quantitative Comparison of Ventilator-Induced Work During Simulated CPAP in Eight Demand-Flow Valve Ventilators Nishimura M, Imanaka H, Taenaka N, Yoshiya I, Takezawa J. Masui. Aug. 1989;38(8):1017-29.
N95 Respirator Surgical Mask with Exhalation Valve.
Exhalation Pressure Relief Defined.
MV2000 Ventilator.
Swivel CPAP Exhalation Valve.
ComfortSelect.
Sleep Apnea Pillow CPAP Nasal Pillow & Mask Device Pillow.
A Proximal System for Positive End-Expiratory Pressure (PEEP) and Continuous Positive Airway Pressure (CPAP) Dupuis YG, Vergilio GC, Spoerel WE. Can Anaesth Soc J. Jul. 1979;26(4):331-4.
Flexicare.
Critical Care Transport NA Critical Care Transport by University of Maryland, American Academy of Orthopaedic Surgeons, Chapter 6, p. 174.
Comfort Classic.
Respironics ComfortSelect Cpap Mask Small/Wide.
Porto2Vent.
Infant Ventilator.
The Biomedical Engineering Handbook NA the Biomedical Engineering Handbook, Mechanical Ventilation, p. 82-5.
Positive End-Expiratory Pressure Devices.
FullLife.
TBird Legacy.
Ventilator.
Muski.
Martindale.
Mestel.
Circadiance.
PCT Search Report and Written Opinion for PCT/US2014/023540, issued Jul. 9, 2014, 9 Pages.
Notification of Transmittal of the International Search Report and the Written Opinion of the International Searching Authority dated Nov. 25, 2013; 7 Pages.
Heat and Moisture Exchangers in Artificial Ventilation: An Experimental Study of the Effect of Gas Leakage S. E. Tilling and B. Hayes Br. J. Anaesth. (1987) 59(9): 1181-1188.
Randomised, Multi-Centre Study of the Usefulness of the Heat and Moisture Exchanger (Provox Hme(®)) in Laryngectomised Patients. Dassonville O, Mérol JC, Bozec A, Swierkosz F, Santini J, Chaïs A, Marcy PY, Giacchero P, Chamorey.

(56) References Cited

OTHER PUBLICATIONS

The Effect of a Newly Developed Heat and Moisture Exchanger for Pulmonary Rehabilitation of Laryngectomized Patients on the Endotracheal Temperature and Humidity. Scheenstra R, Muller S, Vincent A, Ackerstaff A, Jacobi I, Hilgers F. Respir Care. Jan. 27, 2011.
Endotracheal Temperature and Humidity in Laryngectomized Patients in a Warm and Dry Environment and the Effect of a Heat and Moisture Exchanger. Scheenstra RJ, Muller SH, Hilgers FJ. Head Neck. Oct. 27, 2007.
In Vitro Evaluation of an Active Heat-and-Moisture Exchanger: The Hygrovent Gold. Pelosi P, Severgnini P, Selmo G, Corradini M, Chiaranda M, Novario R, Park GR. Respir Care. Apr. 2010;55(4):460-6.
Short-Term Endotracheal Climate Changes and Clinical Effects of a Heat and Moisture Exchanger With an Integrated Electrostatic Virus and Bacterial Filter Developed for Laryngectomized Individuals. Scheenstra RJ, Muller SH, Vincent A, Ackerstaff AH, Jacobi I, Hilgers FJ.
Humidification and Secretion Volume in Mechanically Ventilated Patients. Solomita M, Palmer LB, Daroowalla F, Liu J, Miller D, LeBlanc DS, Smaldone GC. Respir Care. Oct. 2009;54(10):1329-35.
The Clinical and Microbiological Comparison of the Use of Heated Humidifiers and Heat and Moisture Exchanger Filters With Booster in Mechanically Ventilated Patients]. Nadir Ozi__T, Ozcan Kanat D, O__uzülgen IK, Aydo__du M, Hizel K, Gürsel G.
Pulmonary Rehabilitation After Total Laryngectomy Using a Heat and Moisture Exchanger (Hme)]. Lorenz KJ, Maier H. Laryngorhinootologie. Aug. 2009;88(8):513-22. Epub Jul. 30, 2009.
Evaluating Humidity Recovery Efficiency of Currently Available Heat and Moisture Exchangers: A Respiratory System Model Study. Lucato JJ, Adams AB, Souza R, Torquato JA, Carvalho CR, Marini JJ.
The Effect of a Heat and Moisture Exchanger (Provox Hme) on Pulmonary Protection After Total Laryngectomy: A Randomized Controlled Study Bie__S, Okla S, van As-Brooks CJ, Ackerstaff AH. Eur Arch Otorhinolaryngol. Mar. 2010;267(3):429-35.
The Influence of a Heat and Moisture Exchanger on Tracheal Climate in a Cold Environment. Zuur JK, Muller SH, Vincent A, Sinaasappel M, de Jongh FH, Hilgers FJ. Med Eng Phys. Sep. 2009;31(7):852-7. Epub May 28, 2009.
Water Content of Delivered Gases During Non-Invasive Ventilation in Healthy Subjects. Lellouche F, Maggiore SM, Lyazidi A, Deye N, Taillé S, Brochard L. Intensive Care Med. Jun. 2009;35(6):987-95. Epub Mar. 18, 2009.
Prospective Controlled Study of Microbial Colonization of the Trachea in Tracheotomized and Laryngectomized Patients With Hme (Heat and Moisture Exchanger) Kramp B, Donat M, Dommerich S, Pau HW, Podbielski A. Acta Otolaryngol. Oct. 2009;129(10):1136-44.
Heat and Moisture Exchanger: Importance of Humidification in Anaesthesia and Ventilatory Breathing System. Parmar V. J Indian Med Assoc. Aug. 2008;106(8):533-5, 537.
Tracheostoma Humidifier: Influence on Secretion and Voice of Patients With Total Laryngectomy. Masson AC, Fouquet ML, Gonçalves AJ. Pro Fono. Jul.-Sep. 2008;20(3):183-9.
Comparison of Two Humidification Systems for Long-Term Noninvasive Mechanical Ventilation. Nava S, Cirio S, Fanfulla F, Carlucci A, Navarra A, Negri A, Ceriana P. Eur Respir J. Aug. 2008;32(2):460-4.
Assessment of Tracheal Temperature and Humidity in Laryngectomized Individuals and the Influence of a Heat and Moisture Exchanger on Tracheal Climate Zuur JK, Muller SH, Vincent A, Sinaasappel M, de Jongh FH, Hilgers FJ.
Ventilator-Associated Pneumonia in Adults in Developing Countries: A Systematic Review. Arabi Y, Al-Shirawi N, Memish Z, Anzueto A. Int J Infect Dis. Sep. 2008;12(5):505-12.
The Effect of Heat-Moisture Exchanger and Closed-Circuit Technique on Airway Climate During Desflurane Anesthesia. Lu CC, Ho ST, Liaw WJ, Chen RM, Chen TL, Lin CY. J Anesth. 2008;22(1):7-12. Epub Feb. 27, 2008.
[Humidification Assessment of Four Heat and Moisture Exchanger Filters According to Iso 9360: 2000 Standard]. Lannoy D, Décaudin B, Resibois JP, Barrier F, Wierre L, Horrent S, Batt C, Moulront S, Odou P.
Montreal'S Experience With Cyranose Heat and Moisture Exchanger Use in 15 Laryngectomized Patients. Dupuis P, Guertin L, Rainville MS, Prud'homme DL, Lavigne F. J Otolaryngol. Aug. 2007;36(4):208-12.
Secretion Management in the Mechanically Ventilated Patient. Branson RD. Respir Care. Oct. 2007;52(10):1328-42; discussion 1342-7.
Influence of Heat and Moisture Exchanger Respiratory Load on Transcutaneous Oxygenation in Laryngectomized Individuals: A Randomized Crossover Study. Zuur JK, Muller SH, Sinaasappel M, Hart GA, van Zandwijk N, Hilgers FJ.
Moisturizing and Mechanical Characteristics of a New Counter-Flow Type Heated Humidifier. Schumann S, Stahl CA, Möller K, Priebe HJ, Guttmann J. Br J Anaesth. Apr. 2007;98(4):531-8. Epub Feb. 27, 2007.
Efficacy of a Heat and Moisture Exchanger in Inhalation Anesthesia at Two Different Flow Rates. Yamashita K, Yokoyama T, Abe H, Nishiyama T, Manabe M. J Anesth. 2007;21(1):55-8. Epub Jan. 30, 2007.
Airway Humidification With a Heat and Moisture Exchanger in Mechanically Ventilated Neonates : A Preliminary Evaluation. Fassassi M, Michel F, Thomachot L, Nicaise C, Vialet R, Jammes Y, Lagier P, Martin C.
The Effects of Apparatus Dead Space on P(Aco2) in Patients Receiving Lung-Protective Ventilation. Hinkson CR, Benson MS, Stephens LM, Deem S. Respir Care. Oct. 2006;51(10):1140-4.
Effect of Humidifying Devices on the Measurement of Tidal Volume by Mechanical Ventilators. Fujita Y, Imanaka H, Fujino Y, Takeuchi M, Tomita T, Mashimo T, Nishimura M. J Anesth. 2006;20(3):166-72.
Effect of Heat and Moisture Exchanger (Hme) Positioning on Inspiratory Gas Humidification. Inui D, Oto J, Nishimura M. BMC Pulm Med. Aug. 8, 2006;6:19.
Ventilator-Associated Pneumonia Using a Heated Humidifier or a Heat and Moisture Exchanger: A Randomized Controlled Trial [Isrctn88724583]. Lorente L, Lecuona M, Jiménez A, Mora ML, Sierra A. Crit Care. 2006;10(4):R116.
Under-Humidification and Over-Humidification During Moderate Induced Hypothermia With Usual Devices. Lellouche F, Qader S, Taille S, Lyazidi A, Brochard L. Intensive Care Med. Jul. 2006;32(7):1014-21.
[Intensive Care Medicine—Update 2005]. Flohé S, Lendemans S, Schmitz D, Waydhas C. Zentralbl Chir. Jun. 2006;131(3):175-87.
Effect of Ventilation Equipment on Imposed Work of Breathing. French CJ, Bellomo R, Buckmaster J. Crit Care Resusc. Sep. 2001;3(3):148-52.
Double-Heater-Wire Circuits and Heat-and-Moisture Exchangers and the Risk of Ventilator-Associated Pneumonia. Boots RJ, George N, Faoagali JL, Druery J, Dean K, Heller RF. Crit Care Med. Mar. 2006;34(3):687-93.
Influence of Passive Humidification on Respiratory Heat Loss in Tracheotomized Patients. Rozsasi A, Leiacker R, Fischer Y, Keck T. Head Neck. Jul. 2006;28(7):609-13.
Partial Liquid Ventilation: Effects of Closed Breathing Systems, Heat-and-Moisture-Exchangers and Sodalime Absorbers on Perfluorocarbon Evaporation. Wilms CT, Schober P, Kalb R, Loer SA. Eur J Anaesthesiol. Jan. 2006;23(1):31-5.
Bench-to-Bedside Review: Adjuncts to Mechanical Ventilation in Patients With Acute Lung Injury. Rouby JJ, Lu Q. Crit Care. Oct. 5, 2005;9(5):465-71. Epub Jun. 28, 2005.
Prolonged Sedation in the Pediatric Intensive Care Unit May Be Difficult Because of Tolerance, Drug Dependence and Withdrawal, Drug Interactions and Unwanted Drug Effects. We Present Three

(56) References Cited

OTHER PUBLICATIONS

Patients Sedated With Isoflurane via the Anesthetic Conserving Dev Sackey PV, Martling CR, Radell Pj. Paediatr Anaesth. Oct. 2005;15(10):879-85.

Comparison of the Bain System and Uniflow Universal Anaesthetic Breathing Systems in Spontaneously Breathing Young Pigs. Almubarak A, Clarke K, Jackson TL. Vet Anaesth Analg. Sep. 2005;32(5):314-21.

Impact of Humidification Systems on Ventilator-Associated Pneumonia: A Randomized Multicenter Trial. Lacherade JC, Auburtin M, Cerf C, Van de Louw A, Soufir L, Rebufat Y, Rezaiguia S, Ricard JD, Lellouche Am J Respir Crit Care Med. Nov. 15, 2005;172(10):1276-82. Epub 2005.

Compliance, Quality of Life and Quantitative Voice Quality Aspects of Hands-Free Speech. Op de Coul BM, Ackerstaff AH, van As-Brooks CJ, van den Hoogen FJ, Meeuwis CA, Manni JJ, Hilgers FJ. Acta Otolaryngol. Jun. 2005;125(6):629-37.

Volume-Guaranteed Pressure-Support Ventilation Facing Acute Changes in Ventilatory Demand. Jaber S, Delay JM, Matecki S, Sebbane M, Eledjam JJ, Brochard.

Inhalational Anaesthetics in the Icu: Theory and Practice of Inhalational Sedation in the Icu, Economics, Risk-Benefit. Meiser A, Laubenthal H. Best Pract Res Olin Anaesthesiol. Sep. 2005;19(3):523-38.

Tracheal Climate in Laryngectomees After Use of a Heat and Moisture Exchanger. Keck T, Dürr J, Leiacker R, Rettinger G, Rozsasi A. Laryngoscope. Mar. 2005;115(3):534-7.

Automatic Speaking Valve in Speech Rehabilitation for Laryngectomized Patients. Tervonen H, Bäck L, Juvas A, Räsänen P, Mäkitie AA, Sintonen H, Roine RP, Vilkman E, Aaltonen LM. Eur Arch Otorhinolaryngol. Oct. 2005;262(10):816-20. Epub Mar. 2005.

Periodically Changing Ventilator Circuits Is Not Necessary to Prevent Ventilator-Associated Pneumonia When a Heat and Moisture Exchanger Is Used Lorente L, Lecuona M, Galván R, Ramos MJ, Mora ML, Sierra A. Infect Control Hosp Epidemiol. Dec. 2004;25(12):1077-82.

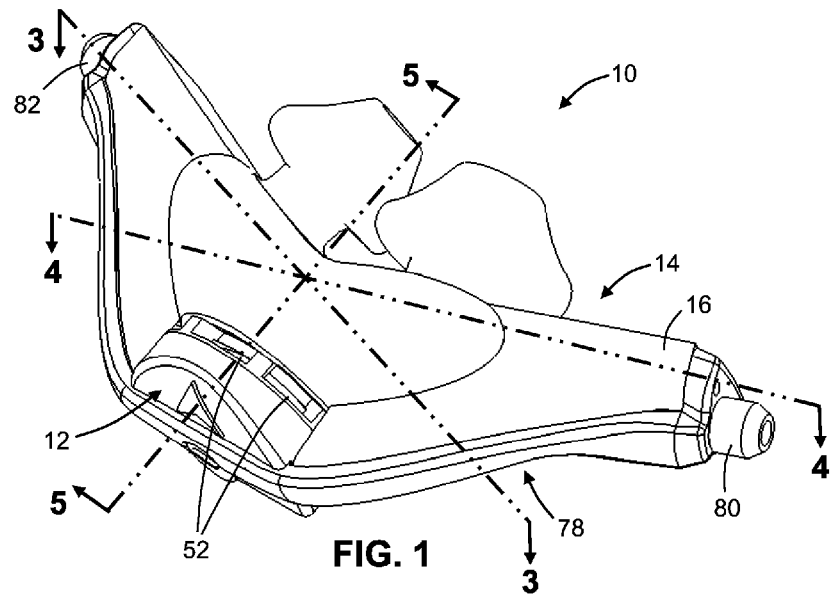

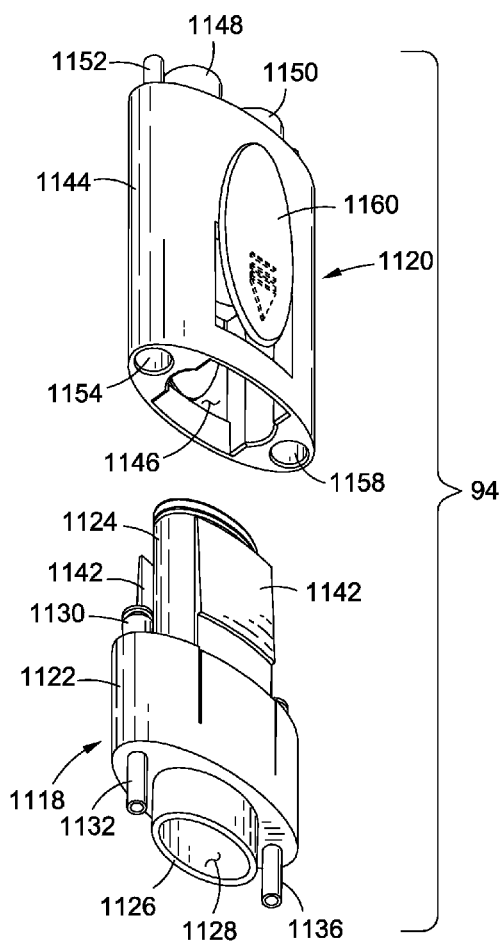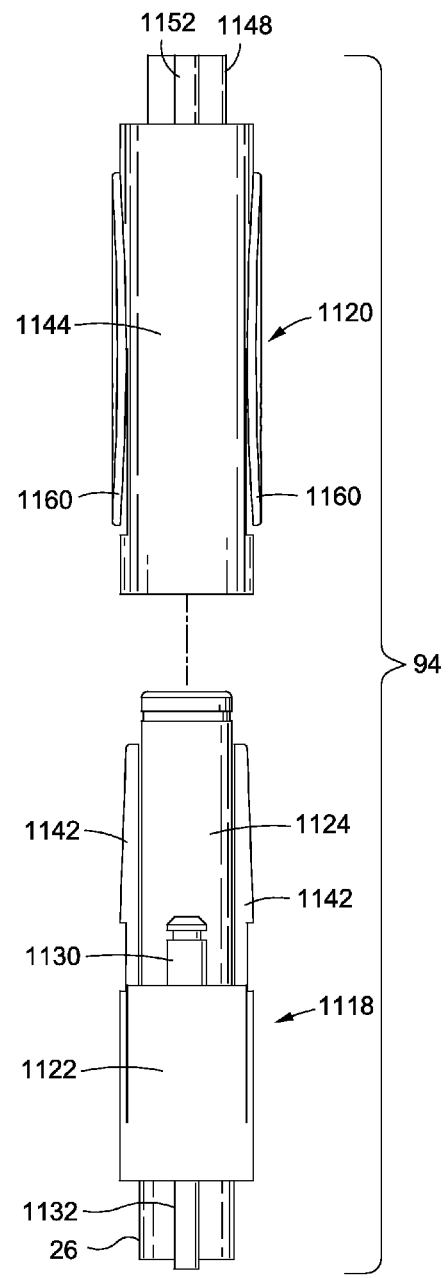
FIG. 31
FIG. 32

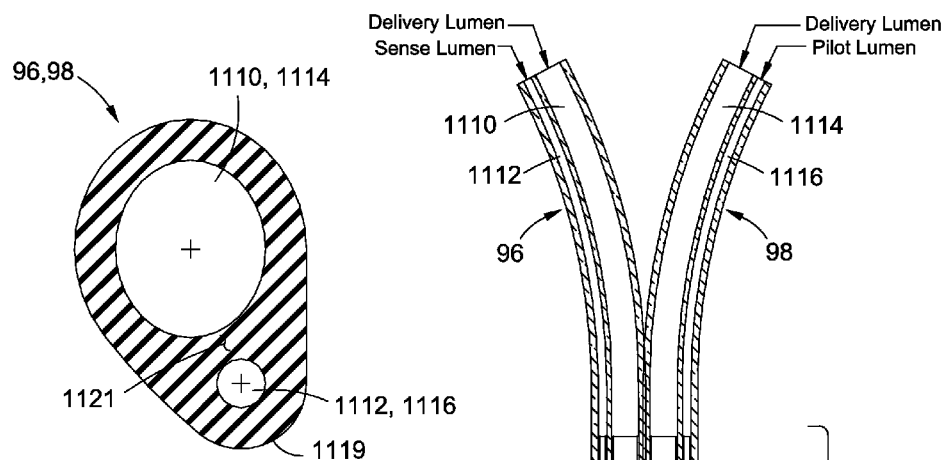
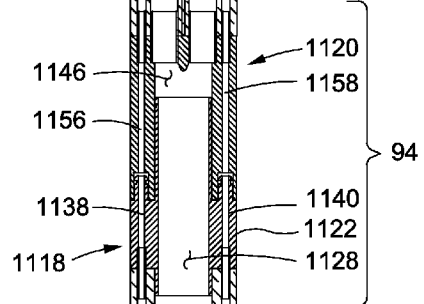
FIG. 33
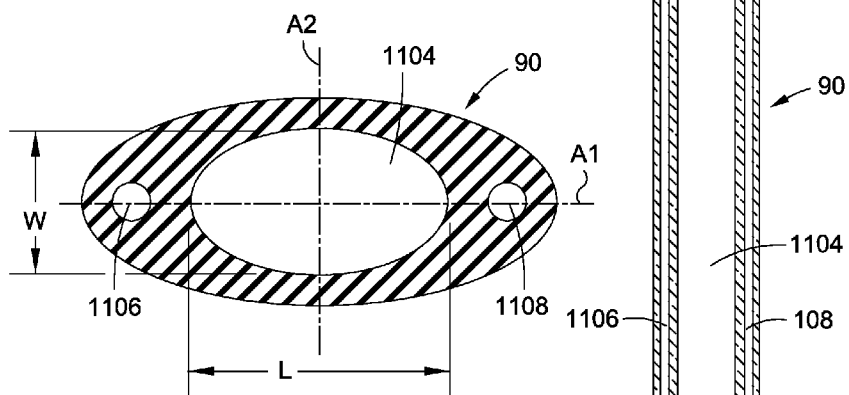
FIG. 34
FIG. 35

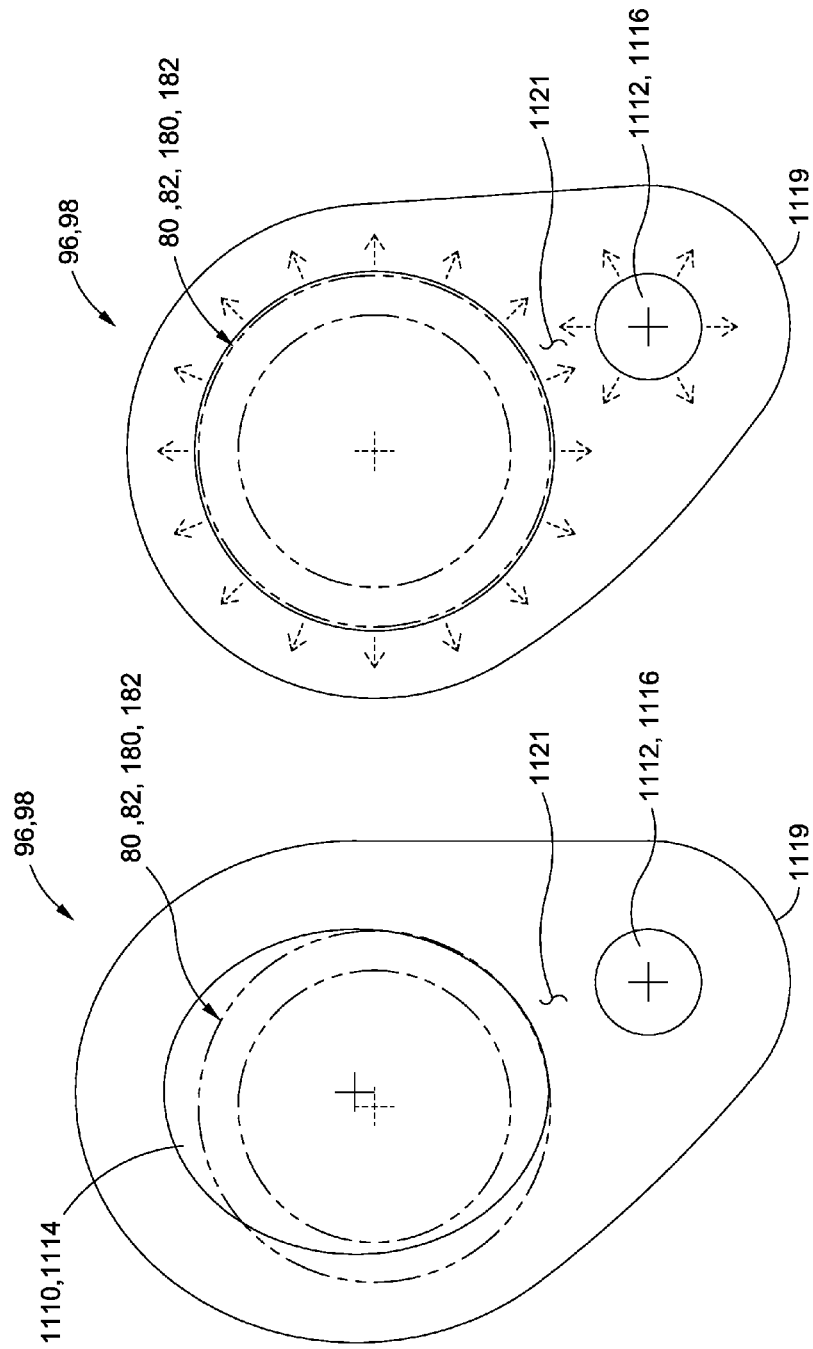

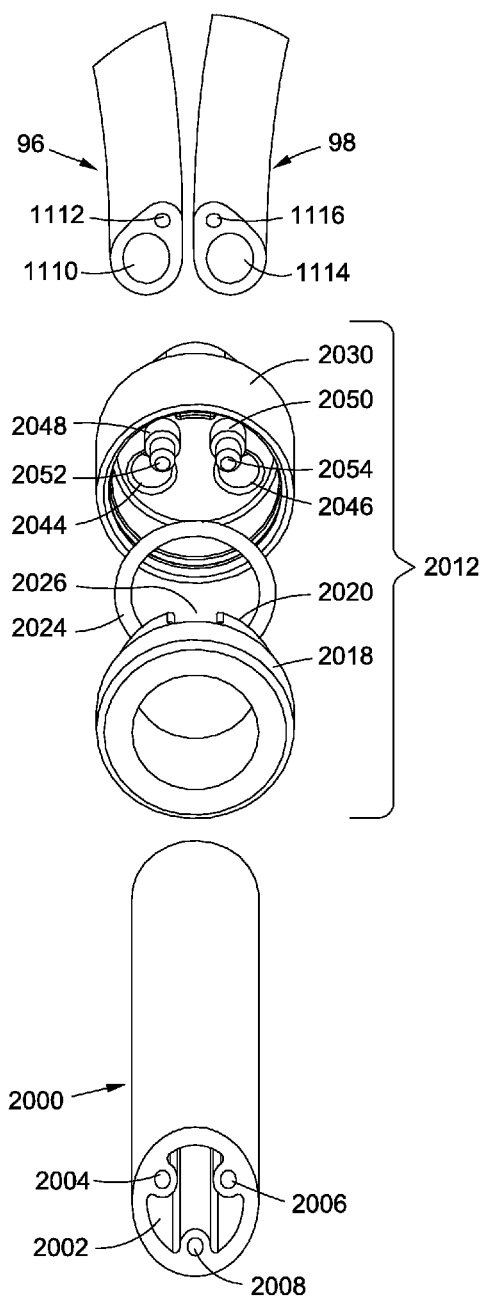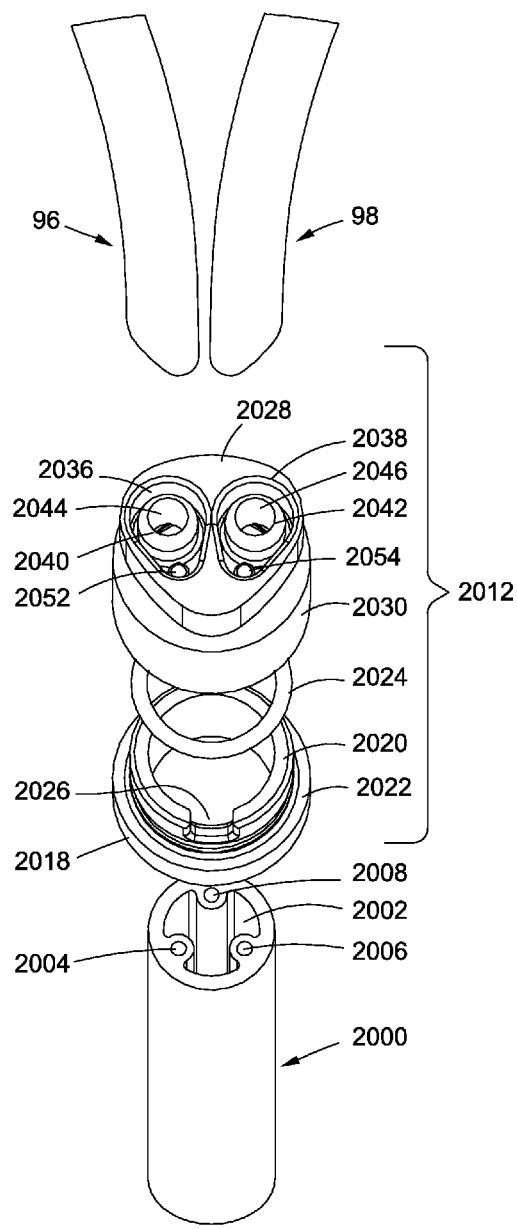
FIG. 45
FIG. 46

VENTILATION MASK WITH INTEGRATED PILOTED EXHALATION VALVE

CROSS-REFERENCE TO RELATED APPLICATIONS

The present application is a continuation-in-part of U.S. patent application Ser. No. 13/572,368 entitled VENTILATION MASK WITH INTEGRATED PILOTED EXHALATION VALVE filed Aug. 10, 2012, which is a continuation-in-part of U.S. patent application Ser. No. 13/411,407 entitled VENTILATION MASK WITH INTEGRATED PILOTED EXHALATION VALVE filed Mar. 2, 2012, which is a continuation of U.S. patent application Ser. No. 13/411,348 entitled VENTILATION MASK WITH INTEGRATED PILOTED EXHALATION VALVE filed Mar. 2, 2012, which claims priority to U.S. Provisional Patent Application Ser. No. 61/499,950 entitled VENTILATION MASK WITH INTEGRATED PILOTED EXHALATION VALVE filed Jun. 22, 2011 and U.S. Provisional Patent Application Ser. No. 61/512,750 entitled VENTILATION MASK WITH INTEGRATED PILOTED EXHALATION VALVE AND METHOD OF VENTILATING A PATIENT USING THE SAME filed Jul. 28, 2011, the disclosures of which are incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to a ventilation mask such as a full face mask, nasal mask, nasal prongs mask or nasal pillows mask for use in critical care ventilation, respiratory insufficiency or OSA (obstructive sleep apnea) with CPAP (Continuous Positive Airway Pressure) therapy and incorporating a piloted exhalation valve inside the mask.

2. Description of the Related Art

As is known in the medical arts, mechanical ventilators comprise medical devices that either perform or supplement breathing for patients. Early ventilators, such as the "iron lung", created negative pressure around the patient's chest to cause a flow of ambient air through the patient's nose and/or mouth into their lungs. However, the vast majority of contemporary ventilators instead use positive pressure to deliver gas to the patient's lungs via a patient circuit between the ventilator and the patient. The patient circuit typically consists of one or two large bore tubes (e.g., from 22 mm ID for adults to 8 mm ID for pediatric) that interface to the ventilator on one end, and a patient mask on the other end. Most often, the patient mask is not provided as part of the ventilator system, and a wide variety of patient masks can be used with any ventilator. The interfaces between the ventilator, patient circuit and patient masks are standardized as generic conical connectors, the size and shape of which are specified by regulatory bodies (e.g., ISO 5356-1 or similar standards).

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

Vented patient circuits are used only to carry gas flow from the ventilator to the patient and patient mask, and require a patient mask with vent openings. When utilizing vented circuits, the patient inspires fresh gas from the patient circuit, and expires $CO_2$-enriched gas, which is purged from the system through the vent openings in the mask. This constant purging of flow through vent openings in the mask when using single-limb circuits provides several disadvantages: 1) it requires the ventilator to provide significantly more flow than the patient requires, adding cost/complexity to the ventilator and requiring larger tubing; 2) the constant flow through the vent openings creates and conducts noise, which has proven to be a significant detriment to patients with sleep apnea that are trying to sleep while wearing the mask; 3) the additional flow coming into proximity of the patient's nose and then exiting the system often causes dryness in the patient, which often drives the need for adding humidification to the system; and 4) patient-expired $CO_2$ flows partially out of the vent holes in the mask and partially into the patient circuit tubing, requiring a minimum flow through the tubing at all times in order to flush the $CO_2$ and minimize the re-breathing of exhaled $CO_2$. To address the problem of undesirable flow of patient-expired $CO_2$ back into the patient circuit tubing, currently known CPAP systems typically have a minimum-required pressure of 4 $cmH_2O$ whenever the patient is wearing the mask, which often produces significant discomfort, claustrophobia and/or feeling of suffocation to early CPAP users and leads to a high (approximately 50%) non-compliance rate with CPAP therapy.

When utilizing non-vented dual limb circuits, the patient inspires fresh gas from one limb (the "inspiratory limb") of the patient circuit and expires $CO_2$-enriched gas from the second limb (the "expiratory limb") of the patient circuit. Both limbs of the dual limb patient circuit are connected together in a "Y" proximal to the patient to allow a single conical connection to the patient mask. When utilizing non-vented single limb circuits, an expiratory valve is placed along the circuit, usually proximal to the patient. During the inhalation phase, the exhalation valve is closed to the ambient and the patient inspires fresh gas from the single limb of the patient circuit. During the exhalation phase, the patient expires $CO_2$-enriched gas from the exhalation valve that is open to ambient. The single limb and exhalation valve are usually connected to each other and to the patient mask with conical connections.

In the patient circuits described above, the ventilator pressurizes the gas to be delivered to the patient inside the ventilator to the intended patient pressure, and then delivers that pressure to the patient through the patient circuit. Very small pressure drops develop through the patient circuit, typically around 1 $cmH_2O$, due to gas flow though the small amount of resistance created by the tubing. Some ventilators compensate for this small pressure drop either by mathematical algorithms, or by sensing the tubing pressure more proximal to the patient.

Ventilators that utilize a dual limb patient circuit typically include an exhalation valve at the end of the expiratory limb proximal to the ventilator, while ventilators that utilize a single limb, non-vented patient circuit typically include an exhalation valve at the end of the single limb proximal to the patient as indicated above. Exhalation valves can have fixed or adjustable PEEP (positive expiratory end pressure), typically in single limb configurations, or can be controlled by the ventilator. The ventilator controls the exhalation valve, closes it during inspiration, and opens it during exhalation. Less sophisticated ventilators have binary control of the exhalation valve, in that they can control it to be either open or closed. More sophisticated ventilators are able to control the exhalation valve in an analog fashion, allowing them to control the pressure within the patient circuit by incrementally opening or closing the valve. Valves that support this incremental control are referred to as active exhalation valves. In existing ventilation systems, active exhalation valves are most typically implemented physically within the ventilator, and the remaining few ventilation systems with active exhalation valves locate the active exhalation valve within the patient circuit proximal to the patient. Active exhalation valves inside ventilators are typically actuated via an electromagnetic coil in the valve, whereas active exhalation valves in the patient circuit are typically pneumatically piloted from the ventilator through a separate pressure source such a secondary blower, or through a proportional valve modulating the pressure delivered by the main pressure source.

BRIEF SUMMARY OF THE INVENTION

In accordance with the present invention, there is provided a mask (e.g., a nasal pillows mask) for achieving positive pressure mechanical ventilation (inclusive of CPAP, ventilatory support, critical care ventilation, emergency applications), and a method for a operating a ventilation system including such mask. The mask preferably includes a pressure sensing modality proximal to the patient connection. Such pressure sensing modality may be a pneumatic port with tubing that allows transmission of the patient pressure back to the ventilator for measurement, or may include a transducer within the mask. The pressure sensing port is used in the system to allow pressure sensing for achieving and/or monitoring the therapeutic pressures. Alternately or additionally, the mask may include a flow sensing modality located therewithin for achieving and/or monitoring the therapeutic flows.

The mask of the present invention also includes a piloted exhalation valve that is used to achieve the target pressures/flows to the patient. In the preferred embodiment, the pilot for the valve is pneumatic and driven from the gas supply tubing from the ventilator. The pilot can also be a preset pressure derived in the mask, a separate pneumatic line from the ventilator, or an electro-mechanical control. In accordance with the present invention, the valve is preferably implemented with a diaphragm.

One of the primary benefits attendant to including the valve inside the mask is that it provides a path for patient-expired CO2 to exit the system without the need for a dual-limb patient circuit, and without the disadvantages associated with a single-limb patient circuit, such as high functional dead space. For instance, in applications treating patients with sleep apnea, having the valve inside the mask allows patients to wear the mask while the treatment pressure is turned off without risk of re-breathing excessive CO2.

Another benefit for having the valve inside the mask is that it allows for a significant reduction in the required flow generated by the ventilator for ventilating the patient since a continuous vented flow for CO2 washout is not required. Lower flow in turn allows for the tubing size to be significantly smaller (e.g., 2-9 mm ID) compared to conventional ventilators (22 mm ID for adults; 8 mm ID for pediatric). However, this configuration requires higher pressures than the patient's therapeutic pressure to be delivered by the ventilator. In this regard, pressure from the ventilator is significantly higher than the patient's therapeutic pressure, though the total pneumatic power delivered is still smaller than that delivered by a low pressure, high flow ventilator used in conjunction with a vented patient circuit and interface. One obvious benefit of smaller tubing is that it provides less bulk for patient and/or caregivers to manage. For today's smallest ventilators, the bulk of the tubing is as significant as the bulk of the ventilator. Another benefit of the smaller tubing is that is allows for more convenient ways of affixing the mask to the patient. For instance, the tubing can go around the patient's ears to hold the mask to the face, instead of requiring straps (typically called "headgear") to affix the mask to the face. Along these lines, the discomfort, complication, and non-discrete look of the headgear is another significant factor leading to the high non-compliance rate for CPAP therapy. Another benefit to the smaller tubing is that the mask can become smaller because it does not need to interface with the large tubing. Indeed, large masks are another significant factor leading to the high non-compliance rate for CPAP therapy since, in addition to being non-discrete, they often cause claustrophobia. Yet another benefit is that smaller tubing more conveniently routed substantially reduces what is typically referred to as "tube drag" which is the force that the tube applies to the mask, displacing it from the patient's face. This force has to be counterbalanced by headgear tension, and the mask movements must be mitigated with cushion designs that have great compliance. The reduction in tube drag in accordance with the present invention allows for minimal headgear design (virtually none), reduced headgear tension for better patient comfort, and reduced cushion compliance that results in a smaller, more discrete cushion.

The mask of the present invention may further include a heat and moisture exchanger (HME) which is integrated therein. The HME can fully or at least partially replace a humidifier (cold or heated pass-over; active or passive) which may otherwise be included in the ventilation system employing the use of the mask. The HME is positioned within the mask so as to be able to intercept the flow delivered from a flow generator to the patient in order to humidify it, and further to intercept the exhaled flow of the patient in order to capture humidity and heat for the next breath. The HME can also be used as a structural member of the mask, adding a cushioning effect and simplifying the design of the cushion thereof.

Further in accordance with the present invention, there is provided various tubing arrangements and an associated Y-connector which may be used to facilitate the operative interface of the mask to a ventilator within a ventilation system. The tubing arrangement may comprise a pair of bi-lumen tubes. One end of each of the bi-lumen tubes is fluidly connected to the mask, with the opposite end being fluidly connected to the Y-connector. The Y-connector is in turn fluidly connected to one end of either a tri-lumen tube or a quad-lumen tube also included in the tubing arrangement, the opposite end of such tri-lumen tube or quad-lumen tube being fluidly connected to the ventilator. The Y-connector is uniquely configured to fluidly connect certain lumens of the tri-lumen tube or the quad-lumen tube to dedicated, corresponding ones of the lumens included in respective ones of the bi-lumen tubes, and to further allow for the selective detachment of the tri-lumen tube or the quad-lumen tube from the bi-lumen tubes.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein:

FIG. 1 is top perspective view of a nasal pillows mask constructed in accordance with one embodiment of the present invention and including an integrated diaphragm-based piloted exhalation valve;

FIG. 2 is an exploded view of the nasal pillows mask shown in FIG. 1;

FIG. 31 is a perspective view of the Y-connector shown in FIGS. 29-30 in its disconnected state;

FIG. 32 is a side-elevational view of the Y-connector shown in FIGS. 29-31 in its disconnected state;

FIG. 33 is a cross-sectional view of one of the identically configured bi-lumen tubes taken along line 33-33 of FIG. 30;

FIG. 34 is a cross-sectional view of the tri-lumen tube taken along line 34-34 of FIG. 30;

FIG. 35 is a cross-sectional view of the tri-lumen tube, Y-connector and bi-lumen tubes shown in FIG. 29 as operatively connected to each other;

FIG. 36 is a cross-sectional view of one of the identically configured bi-lumen tubes shown in FIGS. 29 and 30, but further illustrating in more detail the generally elliptical profile of the gas delivery lumen thereof relative to the generally circular profile of a corresponding connector of the nasal pillows mask which is advanced therein;

FIG. 37 is a cross-sectional view of one of the identically configured bi-lumen tubes which is similar to FIG. 36, but further illustrates the manner in which the receipt of a corresponding, generally circular connector of the nasal pillows mask or Y-connector into the generally elliptical gas delivery lumen facilitates the compression of a portion of the bi-lumen tube as effectively maintains the frictional and airtight engagement thereof with the nasal pillows mask;

FIG. 45 is an exploded view of the Y-connector shown in FIGS. 41 and 42 taken from the perspective shown in FIG. 43; and FIG. 46 is an exploded view of the Y-connector shown in FIGS. 41 and 42 taken from the perspective shown in FIG. 44.

Common reference numerals are used throughout the drawings and detailed description to indicate like elements.

DETAILED DESCRIPTION OF THE INVENTION

Figure 3:
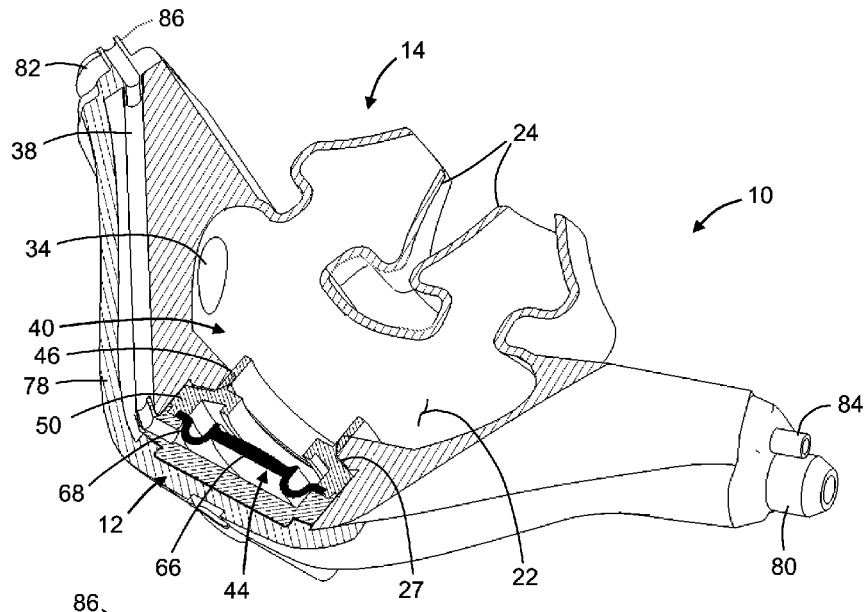
FIG. 3 is a partial cross-sectional view of the nasal pillows mask shown in FIG. 1 taken along lines 3-3 thereof, and depicting the valve pilot lumen extending through the cushion of the mask.

Referring now to the drawings wherein the showings are for purposes of illustrating various embodiments of the present invention only, and not for purposes of limiting the same, FIGS. 1-4 depict a ventilation mask 10 (e.g., a nasal pillows mask) constructed in accordance with the present invention. Though the mask 10 is depicted as a nasal pillows mask, those skilled in the art will recognize that other ventilation masks are contemplated herein, such as nasal prongs masks, nasal masks, fill face masks and oronasal masks. As such, for purposes of this application, the term mask and/or ventilation mask is intended to encompass all such mask structures. The mask 10 includes an integrated, diaphragm-implemented, piloted exhalation valve 12, the structural and functional attributes of which will be described in more detail below.

Figure 4:
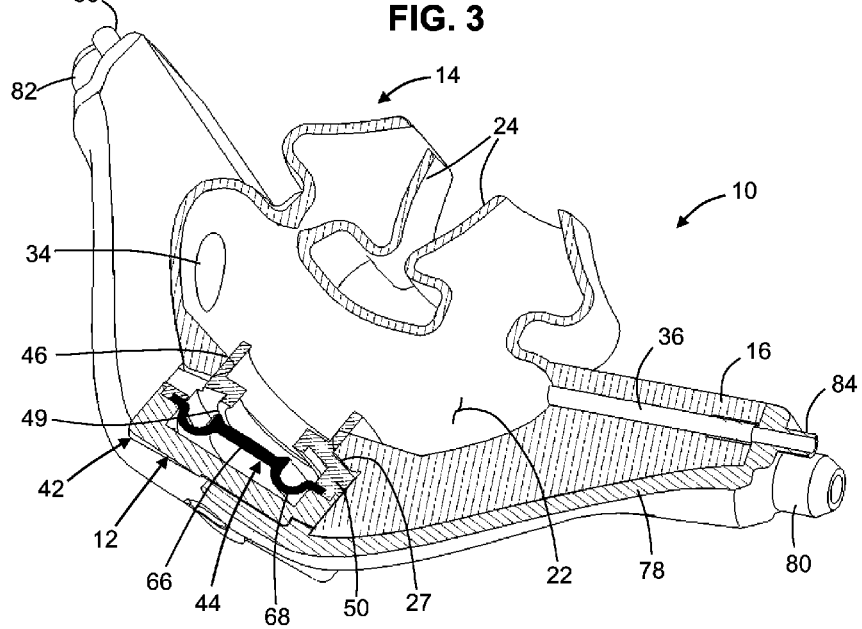
FIG. 4 is a partial cross-sectional view of the nasal pillows mask shown in FIG. 1 taken along lines 4-4 thereof, and depicting the pressure sensing lumen extending through the cushion of the mask.

As shown in FIGS. 1-5, the mask 10 comprises a housing or cushion 14. The cushion 14, which is preferably fabricated from a silicone elastomer having a Shore A hardness in the range of from about 20 to 60 and preferably about 40, is formed as a single, unitary component, and is shown individually in FIG. 6. The cushion 14 includes a main body portion 16 which defines a first outer end surface 18 and an opposed second outer end surface 20. The main body portion 16 further defines an interior fluid chamber 22 which is of a prescribed volume. In addition to the main body portion 16, the cushion 14 includes an identically configured pair of hollow pillow portions 24 which protrude from the main body portion 16 in a common direction and in a prescribed spatial relationship relative to each other. More particularly, in the cushion 14, the spacing between the pillow portions 24 is selected to facilitate the general alignment thereof with the nostrils of an adult patient when the mask 10 is worn by such patient. As seen in FIGS. 3 and 4, each of the pillow portions 24 fluidly communicates with the fluid chamber 22.

As shown in FIG. 2, the main body portion 16 of the cushion 14 includes an enlarged, circularly configured valve opening 26 which is in direct fluid communication with the fluid chamber 22. The valve opening 26 is positioned in generally opposed relation to the pillow portions 24 of the cushion 14, and is circumscribed by an annular valve seat 27 also defined by the main body portion 16. As also shown in FIG. 2, the main body portion 16 further defines opposed first and second inner end surfaces 28, 30 which protrude outwardly from the periphery of the valve opening 26, and are diametrically opposed relative thereto so as to be spaced by an interval of approximately 180°. The valve opening 26, valve seat 27, and first and second inner end surfaces 28, 30 are adapted to accommodate the exhalation valve 12 of the mask 10 in a manner which will be described in more detail below.

Figure 5:
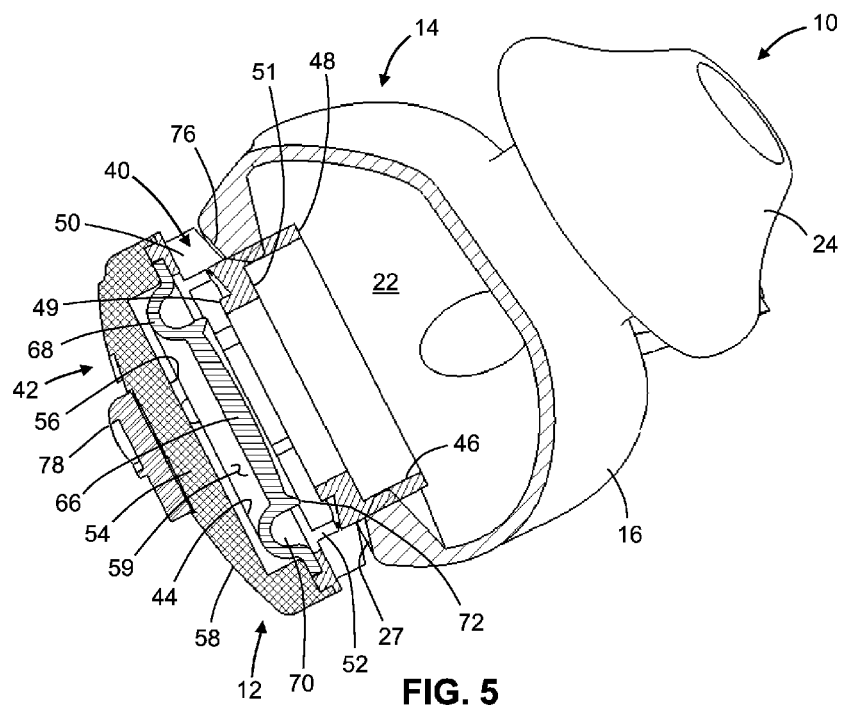
FIG. 5 is a cross-sectional view of the nasal pillows mask shown in FIG. 1 taken along lines 5-5 thereof.
Figure 6:
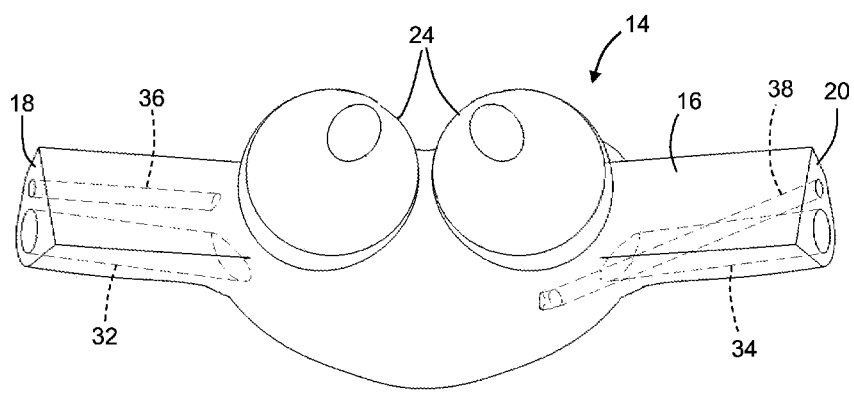
FIG. 6 is a top perspective view of cushion of the nasal pillows mask shown in FIG. 1.

As shown FIGS. 3-6, the main body portion 16 of the cushion 14 further defines first and second gas delivery lumens 32, 34 which extend from respective ones of the first and second outer end surfaces 18, 20 into fluid communication with the fluid chamber 22. Additionally, a pressure sensing lumen 36 defined by the main body portion extends from the first outer end surface 18 into fluid communication with the fluid chamber 22. The main body portion 16 further defines a valve pilot lumen 38 which extends between the second outer end surface 20 and the second inner end surface 30. The use of the first and second gas delivery lumens 32, 34, the pressure sensing lumen 36, and the valve pilot lumen 38 will also be discussed in more detail below. Those of ordinary skill in the art will recognize that the gas delivery lumens 32, 34, may be substituted with a single gas delivery lumen and/or positioned within the cushion 14 in orientations other than those depicted in FIG. 6. For example, the gas delivery lumen(s) of the cushion 14 may be positioned frontally, pointing upwardly, pointing downwardly, etc. rather than extending laterally as shown in FIG. 6.

Referring now to FIGS. 2-5 and 7-9, the exhalation valve 12 of the mask 10 is made of three (3) parts or components, and more particularly a seat member 40, a cap member 42, and a diaphragm 44 which is operatively captured between the seat and cap members 40, 42. The seat and cap members 40, 42 are each preferably fabricated from a plastic material, with the diaphragm 44 preferably being fabricated from an elastomer having a Shore A hardness in the range of from about 20-40.

Figure 7:
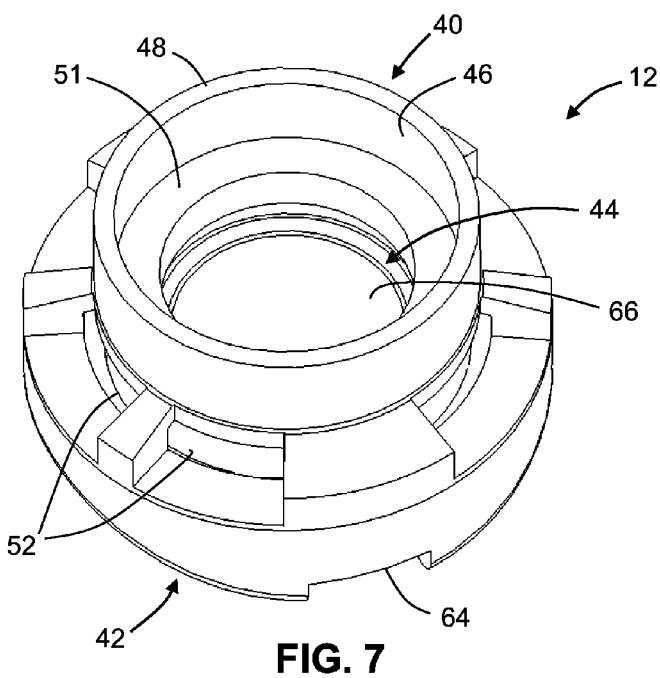
FIG. 7 is a top perspective view of exhalation valve of the nasal pillows mask shown in FIG. 1.
Figure 9:
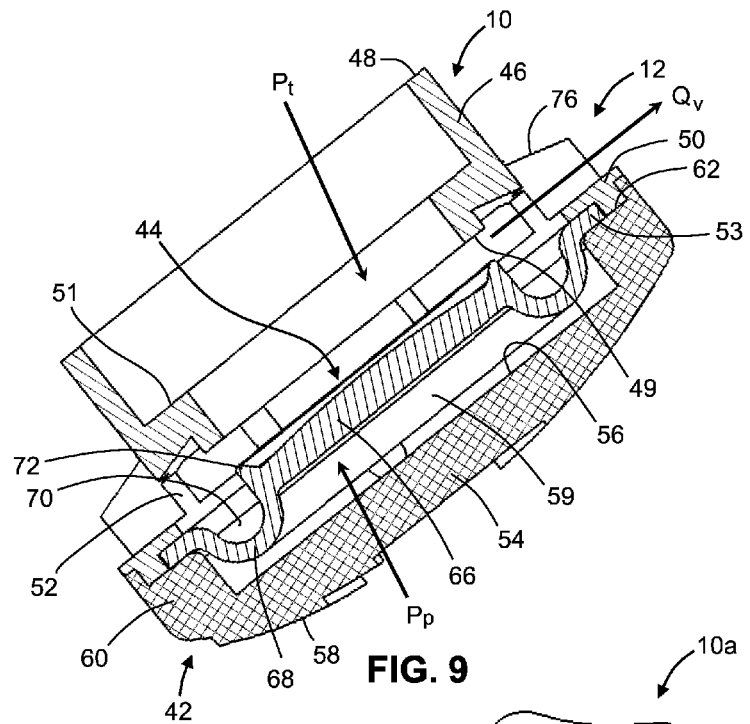
FIG. 9 is a cross-sectional view of exhalation valve shown in FIGS. 7 and 8.

As is most easily seen in FIGS. 2, 7 and 9, the seat member 40 includes a tubular, generally cylindrical wall portion 46 which defines a distal, annular outer rim 48 and an opposed annular inner seating surface 49. As shown in FIG. 9, the diameter of the outer rim 48 exceeds that of the seating surface 49. Along these lines, the inner surface of the wall portion 46 is not of a uniform inner diameter, but rather is segregated into first and second inner surface sections which are of differing inner diameters, and separated by an annular shoulder 51. In addition to the wall portion 46, the seat member 40 includes an annular flange portion 50 which protrudes radially from that end of the wall portion 46 opposite the outer rim 48. As shown in FIGS. 2 and 7, the flange portion 50 includes a plurality of exhaust vents 52 which are located about the periphery thereof in a prescribed arrangement and spacing relative to each other. Additionally, as is apparent from FIG. 9, the seat member 40 is formed such that each of the exhaust vents 52 normally fluidly communicates with the bore or fluid conduit defined by the wall portion 46.

Figure 8:
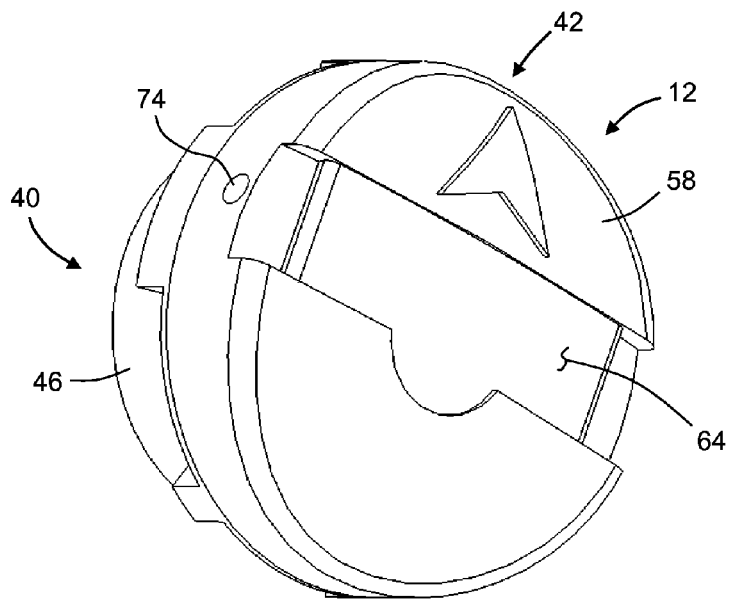
FIG. 8 is a bottom perspective view of exhalation valve shown in FIG. 7.

The cap member 42 of the exhaust valve 12 comprises a circularly configured base portion 54 which defines an inner surface 56 and an opposed outer surface 58. In addition to the base portion 54, the cap member 42 includes an annular flange portion 60 which circumvents and protrudes generally perpendicularly relative to the inner surface 56 of the base portion 60. The flange portion 60 defines a distal annular shoulder 62. As shown in FIG. 9, the shoulder 62 and inner surface 56 extend along respective ones of a spaced, generally parallel pair of planes. Further, as shown in FIG. 8, formed in the outer surface 58 of the base portion 54 is an elongate groove 64 which extends diametrically across the outer surface 58. The use of the groove 64 will be described in more detail below. The seat and cap members 40, 42, when attached to each other in the fully assembled exhalation valve 12, collectively define an interior valve chamber 59 of the exhalation valve 12. More particularly, such valve chamber 59 is generally located between the inner surface 56 defined by the base portion 54 of the cap member 42 and the seating surface 49 defined by the wall portion 46 of the seat member 40.

The diaphragm 44 of the exhalation valve 12, which resides within the valve chamber 59, has a circularly configured, central body portion 66, and a peripheral flange portion 68 which is integrally connected to and circumvents the body portion 66. The body portion 66 includes an annular lip 72 which circumvents and protrudes upwardly from one side or face thereof. The flange portion 68 includes an arcuately contoured primary region and a distal region which protrudes radially from the primary region. As such, the primary region of the flange portion 68 extends between the distal region thereof and the body portion 66, and defines a continuous, generally concave channel 70.

In the exhalation valve 12, the flange portion 68 of the diaphragm 44 is operatively captured between the flange portions 50, 60 of the seat and cap members 40, 42. More particularly, the annular distal region of the flange portion 68 is compressed (and thus captured) between the shoulder 62 defined by the flange portion 60 of the cap member 42, and a complimentary annular shoulder 53 which is defined by the flange portion 50 of the seat member 40 proximate the exhaust vents 52. The orientation of the diaphragm 44 within the valve chamber 59 when captured between the seat and cap members 40, 42 is such that the channel 70 defined by the arcuately contoured primary region of the flange portion 68 is directed toward or faces the seating surface 49 defined by the wall portion 46 of the seat member 40.

The diaphragm 44 (and hence the exhalation valve 12) is selectively moveable between an open position (shown in FIGS. 3-5 and 9) and a closed position. When in its normal, open position, the diaphragm 44 is in a relaxed, unbiased state. Importantly, in either of its open or closed positions, the diaphragm 44 is not normally seated directly against the inner surface 56 defined by the base portion 54 of the cap member 42. Rather, a gap is normally maintained between the body portion 66 of the diaphragm 44 and the inner surface 56 of the base portion 54. The width of such gap when the diaphragm 44 is in its open position is generally equal to the fixed distance separating the inner surface 56 of the base portion 54 from the shoulder 62 of the flange portion 60. Further, when the diaphragm 44 is in its open position, the body portion 66, and in particular the lip 72 protruding therefrom, is itself disposed in spaced relation to the seating surface 49 defined by the wall portion 46 of the seat member 40. As such, when the diaphragm 44 is in its open position, fluid is able to freely pass through the fluid conduit defined by the wall portion 46, between the seating surface 49 and diaphragm 44, and through the exhaust vents 52 to ambient air. As shown in FIGS. 3, 8 and 9, the flange portion 60 of the cap member 42 is further provided with a pilot port 74 which extends therethrough and, in the fully assembled exhalation valve 12, fluidly communicates with that portion of the valve chamber 59 disposed between the body portion 66 of the diaphragm 44 and the inner surface 56 of the base portion 54. The use of the pilot port 74 will also be described in more detail below.

As will be discussed in more detail below, in the exhalation valve 12, the diaphragm 44 is resiliently deformable from its open position (to which it may be normally biased) to its closed position. An important feature of the present invention is that the diaphragm 44 is normally biased to its open position which provides a failsafe to allow a patient to inhale ambient air through the exhalation valve 12 and exhale ambient air therethrough (via the exhaust vents 52) during any ventilator malfunction or when the mask 10 is worn without the therapy being delivered by the ventilator. When the diaphragm 44 is moved or actuated to its closed position, the lip 72 of the body portion 66 is firmly seated against the seating surface 49 defined by the wall portion 46 of the seat member 40. The seating of the lip 72 against the seating surface 49 effectively blocks fluid communication between the fluid conduit defined by the wall portion 46 and the valve chamber 59 (and hence the exhaust vents 52 which fluidly communicate with the valve chamber 59).

In the mask 10, the cooperative engagement between the exhalation valve 12 and the cushion 14 is facilitated by the advancement of the wall portion 46 of the seat member 40 into the valve opening 26 defined by the cushion 14. As best seen in FIG. 5, such advancement is limited by the ultimate abutment or engagement of a beveled seating surface 76 defined by the flange portion 50 of the seat member 40 against the complimentary valve seat 27 of the cushion 14 circumventing the valve opening 26. Upon the engagement of the seating surface 76 to the valve seat 27, the fluid chamber 22 of the cushion 14 fluidly communicates with the fluid conduit defined by the wall portion 46 of the seat member 40. As will be recognized, if the diaphragm 44 resides in its normal, open position, the fluid chamber 22 is further placed into fluid communication with the valve chamber 59 via the fluid conduit defined by the wall portion 46, neither end of which is blocked or obstructed by virtue of the gap defined between the lip 72 of the diaphragm 44 and the seating surface 49 of the wall portion 46.

When the exhalation valve 12 is operatively coupled to the cushion 14, in addition to the valve seat 27 being seated against the seating surface 76, the first and second inner end surfaces 28, 30 of the cushion 14 are seated against respective, diametrically opposed sections of the flange portion 68 defined by the cap member 42. As best seen in FIGS. 3 and 4, the orientation of the exhalation valve 12 relative to the cushion 14 is such that the end of the valve pilot lumen 38 extending to the second inner end surface 30 is aligned and fluidly communicates with the pilot port 74 within the flange portion 60. As such, in the mask 10, the valve pilot lumen 38 is in continuous, fluid communication with that portion of the valve chamber 59 defined between the inner surface 56 of the base portion 54 and the body portion 66 of the diaphragm 44.

To assist in maintaining the cooperative engagement between the exhalation valve 12 and the cushion 14, the mask 10 is further preferably provided with an elongate frame member 78. The frame member 78 has a generally V-shaped configuration, with a central portion thereof being accommodated by and secured within the complimentary groove 64 formed in the outer surface 58 defined by the base portion 54 of the cap member 42. As shown in FIGS. 3 and 4, the opposed end portions of the frame members 78 are cooperatively engaged to respective ones of the first and second outer end surfaces 18, 20 of the cushion 14. More particularly, as shown in FIG. 2, the frame member 78 includes an identically configured pair of first and second connectors 80, 82 which extend from respective ones of the opposed end portions thereof. An inner portion of the first connector 80 is advanced into and frictionally retained within the first gas delivery lumen 32 of the cushion 14. Similarly, an inner portion of the second connector 82 is advanced into and frictionally retained within the second gas delivery lumen 34 of the cushion 14. In addition to the inner portions advanced into respective ones of the first and second gas delivery lumens 32, 34, the first and second connectors 80, 82 of the frame member 78 each further include an outer portion which, as will be described in more detail below, is adapted to be advanced into and frictionally retained within a corresponding lumen of a respective one of a pair of bi-lumen tubes fluidly coupled to the mask 10.

As shown in FIGS. 3 and 4, the frame member 78 further includes a tubular, cylindrically configured pressure port 84 which is disposed adjacent the first connector 80. The pressure port 84 is aligned and fluidly communicates with the pressure sensing lumen 36 of the cushion 14. Similarly, the frame member 78 is also provided with a tubular, cylindrically configured pilot port 86 which is disposed adjacent the second connector 82. The pilot port 86 is aligned and fluidly communicates with the valve pilot lumen 38 of the cushion 14. As will also be discussed in more detail below, the pressure and pilot ports 84, 86 of the frame member 78 are adapted to be advanced into and frictionally maintained within corresponding lumens of respective ones of the aforementioned pair of bi-lumen tubes which are fluidly connected to the mask 10 within a ventilation system incorporating the same. The receipt of the frame member 78 within the groove 64 of the cap member 42 ensures that the cushion 14, the exhalation valve 12 and the frame member 78 are properly aligned, and prevents relative movement therebetween. Though not shown, it is contemplated that in one potential variation of the mask 10, the cushion 14 may be formed so as not to include the valve pilot lumen 38. Rather, a suitable valve pilot lumen would be formed directly within the frame member 78 so as to extend therein between the pilot port 86 thereof and the pilot port 74 of the exhalation valve 12.

In the mask 10, the exhalation valve 12 is piloted, with the movement of the diaphragm 44 to the closed position described above being facilitated by the introduction of positive fluid pressure into the valve chamber 59. More particularly, it is contemplated that during the inspiratory phase of the breathing cycle of a patient wearing the mask 10, the valve pilot lumen 38 will be pressurized by a pilot line fluidly coupled to the pilot port 86, with pilot pressure being introduced into that portion of the valve chamber 59 normally defined between the body portion 66 of the diaphragm 44 and the inner surface 56 defined by the base portion 54 of the cap member 42 via the pilot port 74 extending through the flange portion 60 of the cap member 42. The fluid pressure level introduced into the aforementioned region of the valve chamber 59 via the pilot port 74 will be sufficient to facilitate the movement of the diaphragm 44 to its closed position described above.

Conversely, during the expiratory phase of the breathing cycle of the patient wearing the mask 10, it is contemplated that the discontinuation or modulation of the fluid pressure through the valve pilot lumen 38 and hence into the aforementioned region of the valve chamber 59 via the pilot port 74, coupled with the resiliency of the diaphragm 44 and/or positive pressure applied to the body portion 66 thereof, will facilitate the movement of the diaphragm 44 back to the open position or to a partially open position. In this regard, positive pressure as may be used to facilitate the movement of the diaphragm 44 to its open position may be provided by air which is exhaled from the patient during the expiratory phase of the breathing circuit and is applied to the body portion 66 via the pillows portions 24 of the cushion 14, the fluid chamber 22, and the fluid conduit defined by the wall portion of the seat member 40. As will be recognized, the movement of the diaphragm 44 to the open position allows the air exhaled from the patient to be vented to ambient air after entering the valve chamber 59 via the exhaust vents 52 within the flange portion 50 of the seat member 40 which, as indicated above, fluidly communicate with the valve chamber 59.

As will be recognized, based on the application of pilot pressure thereto, the diaphragm 44 travels from a fully open position through a partially open position to a fully closed position. In this regard, the diaphragm 44 will be partially open or partially closed during exhalation to maintain desired ventilation therapy. Further, when pilot pressure is discontinued to the diaphragm 44, it moves to an open position wherein the patient can inhale and exhale through the mask 10 with minimal restriction and with minimal carbon dioxide retention therein. This is an important feature of the present invention which allows a patient to wear the mask 10 without ventilation therapy being applied to the mask 10, the aforementioned structural and functional features of the mask 10 making it more comfortable to wear, and further allowing it to be worn without carbon dioxide buildup. This feature is highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 10, during patient inhalation, the valve pilot lumen 38 is pressurized, which causes the diaphragm 44 to close against the seating surface 49, thus effectively isolating the fluid chamber 22 of the mask 10 from the outside ambient air. The entire flow delivered from a flow generator fluidly coupled to the mask 10 is inhaled by the patient, assuming that unintentional leaks at the interface between the cushion 14 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 38 is controlled so that the exhaled flow from the patient can be exhausted to ambient air through the exhalation valve 12 in the aforementioned manner. In this regard, the pilot pressure is "servoed" so that the position of the diaphragm 44 relative to the seating surface 49 is modulated, hence modulating the resistance of the exhalation valve 12 to the exhaled flow and effectively ensuring that the pressure in the fluid chamber 22 of the mask 10 is maintained at a prescribed therapeutic level throughout the entire length of the exhalation phase. When the valve pilot lumen 38 is not pressurized, the exhalation valve 12 is in a normally open state, with the diaphragm 44 being spaced from the seating surface 49 in the aforementioned manner, thus allowing the patient to spontaneously breathe in and out with minimal pressure drop (also referred to as back-pressure) in the order of less than about 2 cm H2O at 60 l/min. As a result, the patient can comfortably breathe while wearing the mask 10 and while therapy is not being administered to the patient.

Figure 11A:
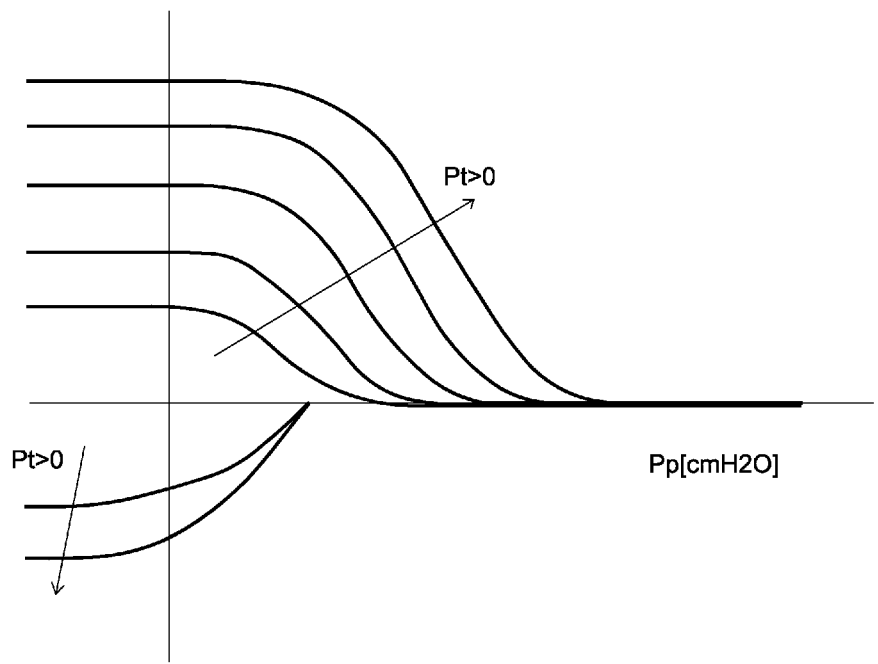
FIGS. 11A, 11B and 11C are a series of graphs which provide visual representations corresponding to exemplary performance characteristics of the exhalation valve subassembly of any nasal pillows mask constructed in accordance with the present invention.
Figure 11B:
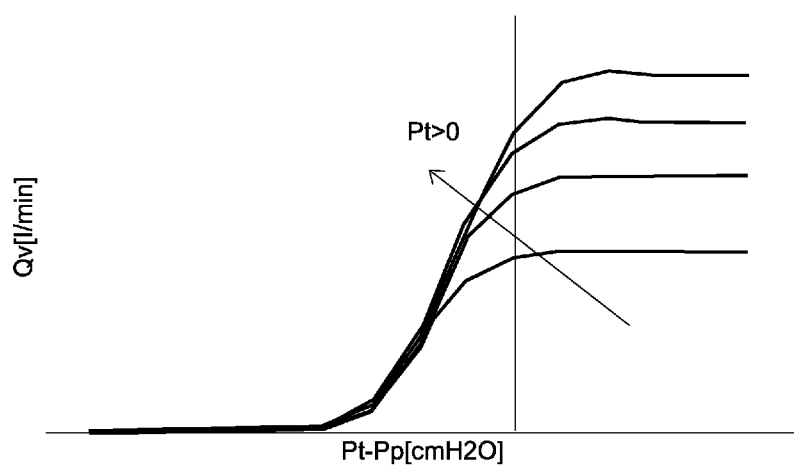
Figure 11C:
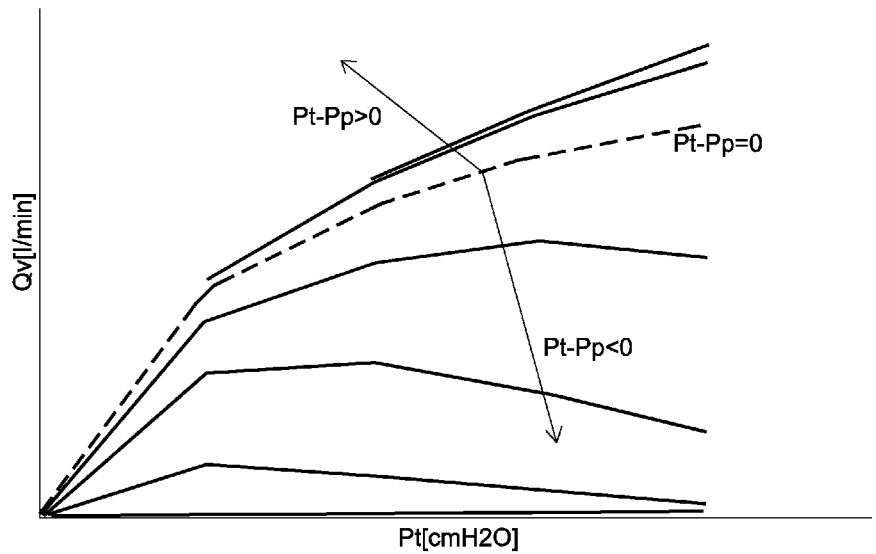

Referring now to FIGS. 11A, 11B and 11C, during use of the mask 10 by a patient, the functionality of the exhalation valve 12 can be characterized with three parameters. These are Pt which is the treatment pressure (i.e., the pressure in the mask 10 used to treat the patient; Pp which is the pilot pressure (i.e., the pressure used to pilot the diaphragm 44 in the exhalation valve 12); and Qv which is vented flow (i.e., flow that is exhausted from inside the exhalation valve 12 to ambient. These three particular parameters are labeled as Pt, Pp and Qv in FIG. 9. When the patient is ventilated, Pt is greater than zero, with the functionality of the exhalation valve 12 being described by the family of curves in the first and second quadrants of FIG. 11A. In this regard, as apparent from FIG. 11A, for any given Pt, it is evident that by increasing the pilot pressure Pp, the exhalation valve 12 will close and the vented flow will decrease. A decrease in the pilot pressure Pp will facilitate the opening of the valve 12, thereby increasing vented flow. The vented flow will increase until the diaphragm 44 touches or contacts the inner surface 56 of the base portion 54 of the cap member 42, and is thus not able to open further. Conversely, when the patient is not ventilated, the inspiratory phase can be described by the third and fourth quadrants. More particularly, Qv is negative and air enters the mask 10 through the valve 12, with the pressure Pt in the mask 10 being less than or equal to zero. Pilot pressure Pp less than zero is not a configuration normally used during ventilation of the patient, but is depicted for a complete description of the functionality of the valve 12. The family of curves shown in FIG. 11A can be described by a parametric equation. Further, the slope and asymptotes of the curves shown in FIG. 11A can be modified by, for example and not by way of limitation, changing the material used to fabricate the diaphragm 44, changing the thickness of the diaphragm 44, changing the area ratio between the pilot side and patient side of the diaphragm 44, changing the clearance between the diaphragm 44 and the seating surface 49, and/or changing the geometry of the exhaust vents 52.

An alternative representation of the functional characteristics of the valve 12 can be described by graphs in which $\Delta P = Pt - Pp$ is shown. For example, the graph of FIG. 11B shows that for any given Pt, the vented flow can be modulated by changing $\Delta P$. In this regard, $\Delta P$ can be interpreted as the physical position of the diaphragm 44. Since the diaphragm 44 acts like a spring, the equation describing the relative position d of the diaphragm 44 from the seating surface 49 of the seat member 40 is $k \cdot d + Pt \cdot At = Pp \cdot Ap$, where At is the area of the diaphragm 44 exposed to treatment pressure Pt and Ap is the area of the diaphragm 44 exposed to the pilot pressure Pp. A similar, alternative representation is provided in the graph of FIG. 11C which shows Pt on the x-axis and $\Delta P$ as the parameter. In this regard, for any given $\Delta P$, the position d of the diaphragm 44 is determined, with the valve 12 thus being considered as a fixed opening valve. In this scenario Pt can be considered the driving pressure pushing air out of the valve 12, with FIG. 11C further illustrating the highly non-linear behavior of the valve 12.

Figure 12:
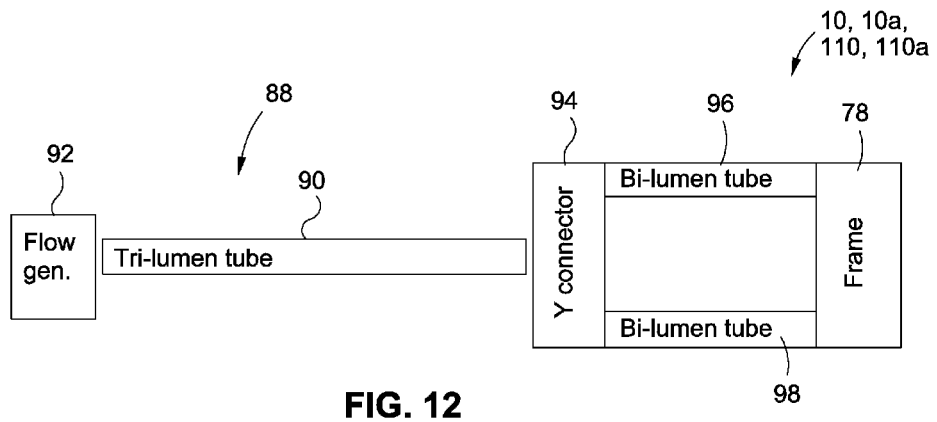
FIG. 12 is a schematic representation of an exemplary ventilation system wherein a tri-lumen tube is used to facilitate the operative interface between any nasal pillows mask constructed in accordance with the present invention a flow generating device.

FIG. 12 provides a schematic representation of an exemplary ventilation system 88 wherein a tri-lumen tube 90 is used to facilitate the fluid communication between the mask 10 and a blower or flow generator 92 of the system 88. As represented in FIG. 12, one end of the tri-lumen tube 90 is fluidly connected to the flow generator 92, with the opposite end thereof being fluidly connected to a Y-connector 94. The three lumens defined by the tri-lumen tube 90 include a gas delivery lumen, a pressure sensing lumen, and a valve pilot lumen. The gas delivery lumen is provided with an inner diameter or ID in the range of from about 2 mm to 15 mm, and preferably about 4 mm to 10 mm. The pressure sensing and valve pilot lumens of the tri-lumen tube 90 are each preferably provided with an ID in the range of from about 0.5 mm to 2 mm. The outer diameter or OD of the tri-lumen tube 90 is preferably less than 17 mm, with the length thereof in the system 88 being about 2 m. The Y-connector 94 effectively bifurcates the tri-lumen tube 90 into the first and second bi-lumen tubes 96, 98, each of which has a length of about 6 inches. The first bi-lumen tube 96 includes a gas delivery lumen having an ID in the same ranges described above in relation to the gas delivery lumen of the tri-lumen tube 90. The gas delivery lumen of the first bi-lumen tube 96 is fluidly coupled to the outer portion of the first connector 80 of the frame member 78. The remaining lumen of the first bi-lumen tube 96 is a pressure sensing lumen which has an ID in the same range described above in relation to the pressure sensing lumen of the tri-lumen tube 90, and is fluidly coupled to the pressure port 84 of the frame member 78. Similarly, the second bi-lumen tube 98 includes a gas delivery lumen having an ID in the same ranges described above in relation to the gas delivery lumen of the tri-lumen tube 90. The gas delivery lumen of the second bi-lumen tube 98 is fluidly coupled to the outer portion of the second connector 82 of the frame member 78. The remaining lumen of the second bi-lumen tube 98 is a valve pilot lumen which has an ID in the same range described above in relation to the valve pilot lumen of the tri-lumen tube 90, and is fluidly coupled to the pilot port 86 of the frame member 78.

In the system 88 shown in FIG. 12, the pilot pressure is generated at the flow generator 92. In the prior art, a secondary blower or proportional valve that modulates the pressure from a main blower is used to generate a pressure to drive an expiratory valve. However, in the system 88 shown in FIG. 12, the outlet pressure of the flow generator 92 is used, with the flow generator 92 further being controlled during patient exhalation in order to have the correct pilot pressure for the exhalation valve 12. This allows the system 88 to be inexpensive, not needing additional expensive components such as proportional valves or secondary blowers.

Figure 13:
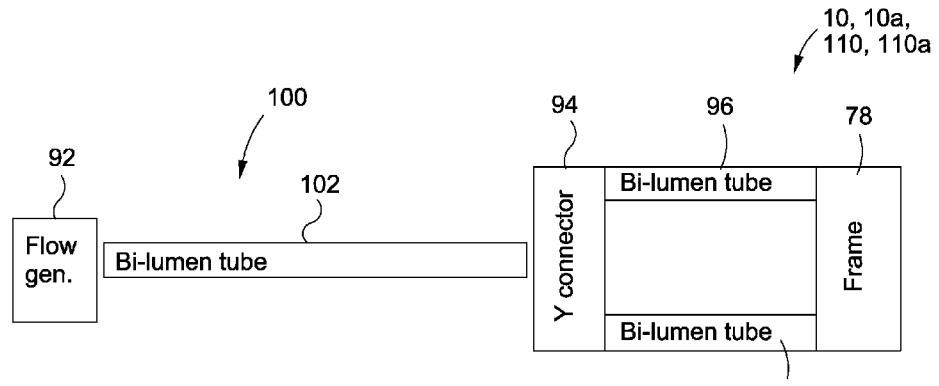
FIG. 13 is a schematic representation of an exemplary ventilation system wherein a bi-lumen tube is used to facilitate the operative interface between any nasal pillows mask constructed in accordance with the present invention and a flow generating device.

FIG. 13 provides a schematic representation of another exemplary ventilation system 100 wherein a bi-lumen tube 102 is used to facilitate the fluid communication between the mask 10 and the blower or flow generator 92 of the system 100. As represented in FIG. 13, one end of the bi-lumen tube 102 is fluidly connected to the flow generator 92, with the opposite end thereof being fluidly connected to the Y-connector 94. The two lumens defined by the bi-lumen tube 102 include a gas delivery lumen and a pressure sensing lumen. The gas delivery lumen is provided with an inner diameter or ID in the range of from about 2 mm to 10 mm, and preferably about 4 mm to 7 mm. The pressure sensing lumen of the bi-lumen tube 102 is preferably provided with an ID in the range of from about 0.5 mm to 2 mm. The outer diameter or OD of the bi-lumen tube 102 is preferably less than 11 mm, with the length thereof being about 2 m. The Y-connector 94 effectively bifurcates the bi-lumen tube 102 into the first and second bi-lumen tubes 96, 98, each of which has a length of about 6 inches. The first bi-lumen tube 96 includes a gas delivery lumen having an ID in the same ranges described above in relation to the gas delivery lumen of the bi-lumen tube 102. The gas delivery lumen of the first bi-lumen tube 96 is fluidly coupled to the outer portion of the first connector 80 of the frame member 78. The remaining lumen of the first bi-lumen tube 96 is a pressure sensing lumen which has an ID in the same range described above in relation to the pressure sensing lumen of the bi-lumen tube 102, and is fluidly coupled to the pressure port 84 of the frame member 78. Similarly, the second bi-lumen tube 98 includes a gas delivery lumen having an ID in the same ranges described above in relation to the gas delivery lumen of the bi-lumen tube 102. The gas delivery lumen of the second bi-lumen tube 98 is fluidly coupled to the outer portion of the second connector 82 of the frame member 78. The remaining lumen of the second bi-lumen tube 98 is a valve pilot lumen which has an ID in the same range described above in relation to the pressure sensing lumen of the bi-lumen tube 102, and is fluidly coupled to the pilot port 86 of the frame member 78.

In the system 100 shown in FIG. 13, the valve pilot lumen 38 is connected to the gas delivery air path at the Y-connector 94. More particularly, the gas delivery lumen of the bi-lumen tube 102 is transitioned at the Y-connector 94 to the valve pilot lumen of the second bi-lumen tube 98. As such, the pilot pressure will be proportional to the outlet pressure of the flow generator 92 minus the pressure drop along the bi-lumen tube 102, which is proportional to delivered flow. This solution is useful when small diameter tubes are used in the system 100, since such small diameter tubes require higher outlet pressure from the flow generator 92 for the same flow. In this regard, since the pressure at the outlet of the flow generator 92 would be excessive for piloting the exhalation valve 12, a lower pressure along the circuit within the system 100 is used. In the system 100, though it is easier to tap in at the Y-connector 94, anywhere along the tube network is acceptable, depending on the pressure level of the flow generator 92 which is the pressure required by the patient circuit in order to deliver the therapeutic pressure and flow at the patient.

In each of the systems 88, 100, it is contemplated that the control of the flow generator 92, and hence the control of therapeutic pressure delivered to the patient wearing the mask 10, may be governed by the data gathered from dual pressure sensors which take measurements at the mask 10 and the output of the flow generator 92. As will be recognized, pressure sensing at the mask 10 is facilitated by the pressure sensing lumen 36 which, as indicated above, is formed within the cushion 14 and fluidly communicates with the fluid chamber 22 thereof. As also previously explained, one of the lumens of the first bi-lumen tube 96 in each of the systems 88, 100 is coupled to the pressure port 84 (and hence the pressure sensing lumen 36). As a result, the first bi-lumen tube 96, Y-connector 94 and one of the tri-lumen or bi-lumen tubes 90, 102 collectively define a continuous pressure sensing fluid path between the mask 10 and a suitable pressure sensing modality located remotely therefrom. A more detailed discussion regarding the use of the dual pressure sensors to govern the delivery of therapeutic pressure to the patient is found in Applicant's co-pending U.S. application Ser. No. 13/411,257 entitled Dual Pressure Sensor Continuous Positive Airway Pressure (CPAP) Therapy filed Mar. 2, 2012, the entire disclosure of which is incorporated herein by reference.

Figure 10:
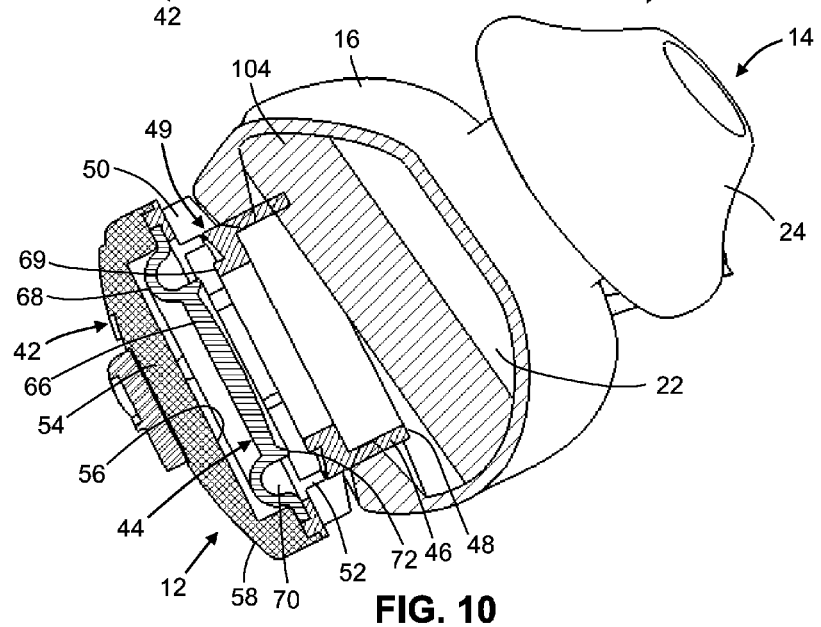
FIG. 10 is a cross-sectional view similar to FIG. 5, but depicting a variant of the nasal pillows mask shown in FIG. 1 wherein an HME is integrated into the cushion thereof.

Referring now to FIG. 10, there is shown a mask 10a which comprises a variant of the mask 10. The sole distinction between the masks 10, 10a lies in the mask 10a including a heat and moisture exchanger or HME 104 which is positioned within the fluid chamber 22 of the cushion 14. The HME 104 is operative to partially or completely replace a humidifier (cold or heated pass-over; active or passive) which would otherwise be fluidly coupled to the mask 10a. This is possible because the average flow through the system envisioned to be used in conjunction with the mask 10a is about half of a prior art CPAP mask, due to the absence of any intentional leak in such system.

The HME 104 as a result of its positioning within the fluid chamber 22, is able to intercept the flow delivered from the flow generator to the patient in order to humidify it, and is further able to capture humidity and heat from exhaled flow for the next breath. The pressure drop created by the HME 104 during exhalation (back-pressure) must be limited, in the order of less than 5 cmH2O at 60 l/min, and preferably lower than 2 cmH2O at 60 l/min. These parameters allow for a low back-pressure when the patient is wearing the mask 10a and no therapy is delivered to the patient.

It is contemplated that the HME 104 can be permanently assembled to the cushion 14, or may alternatively be removable therefrom and thus washable and/or disposable. In this regard, the HME 104, if removable from within the cushion 14, could be replaced on a prescribed replacement cycle. Additionally, it is contemplated that the HME 104 can be used as an elastic member that adds elasticity to the cushion 14. In this regard, part of the elasticity of the cushion 14 may be attributable to its silicone construction, and further be partly attributable to the compression and deflection of the HME 104 inside the cushion 14.

Referring now to FIGS. 15-19, there is shown a ventilation mask 110 (e.g., a nasal pillows mask) constructed in accordance with another embodiment of the present invention. Like the mask 10 described above, the mask 110 includes an integrated, diaphragm-implemented, piloted exhalation valve 112, the structural and functional attributes of which will be described in more detail below.

As shown in FIGS. 15-19, the mask 110 comprises a housing or cushion 114. The cushion 114, which is preferably fabricated from a silicone elastomer having a Shore A hardness in the range of from about 20 to 60 and preferably about 40, is formed as a single, unitary component, and is shown individually in FIG. 20. The cushion 114 includes a main body portion 116 which defines a first outer end surface 118 and an opposed second outer end surface 120. The main body portion 116 further defines an interior fluid chamber 122 which is of a prescribed volume. In addition to the main body portion 116, the cushion 14 includes an identically configured pair of hollow pillow portions 124 which protrude from the main body portion 116 in a common direction and in a prescribed spatial relationship relative to each other. More particularly, in the cushion 114, the spacing between the pillow portions 124 is selected to facilitate the general alignment thereof with the nostrils of an adult patient when the mask 110 is worn by such patient. Each of the pillow portions 124 fluidly communicates with the fluid chamber 122.

Figure 16:
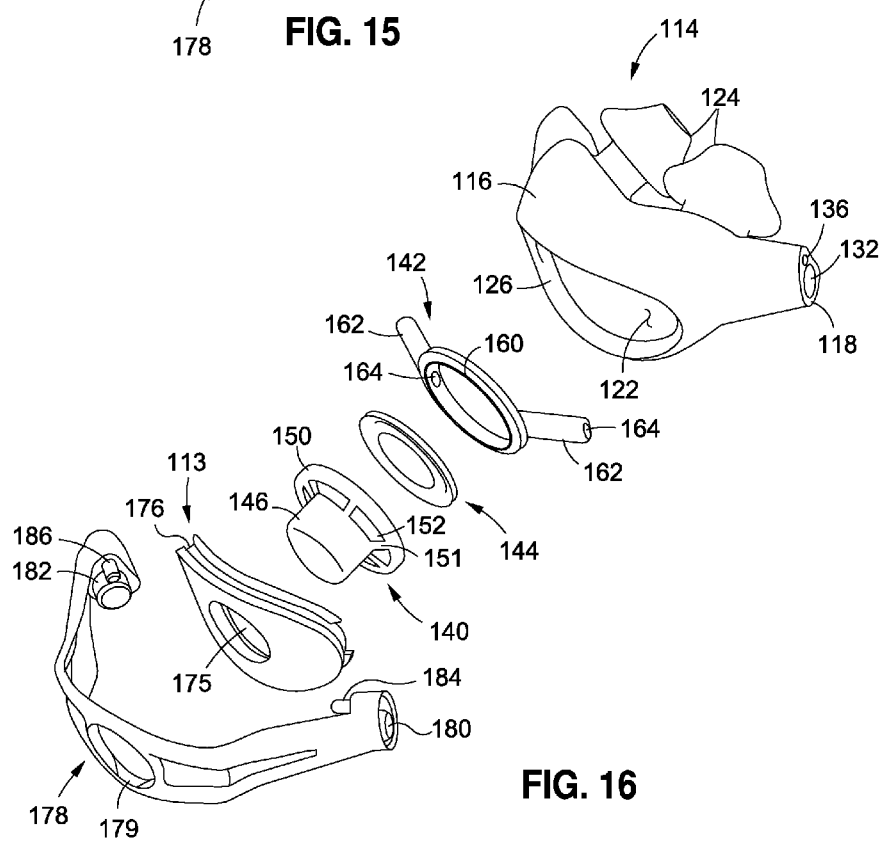
FIG. 16 is an exploded view of the nasal pillows mask shown in FIG. 15.

As shown in FIG. 16, the main body portion 116 of the cushion 114 includes an enlarged, circularly configured valve opening 126 which is in direct fluid communication with the fluid chamber 122. The valve opening 126 is positioned in generally opposed relation to the pillow portions 124 of the cushion 114. The valve opening 126 is adapted to accommodate an exhalation valve subassembly 111 of the mask 110 in a manner which will be described in more detail below.

Figure 18:
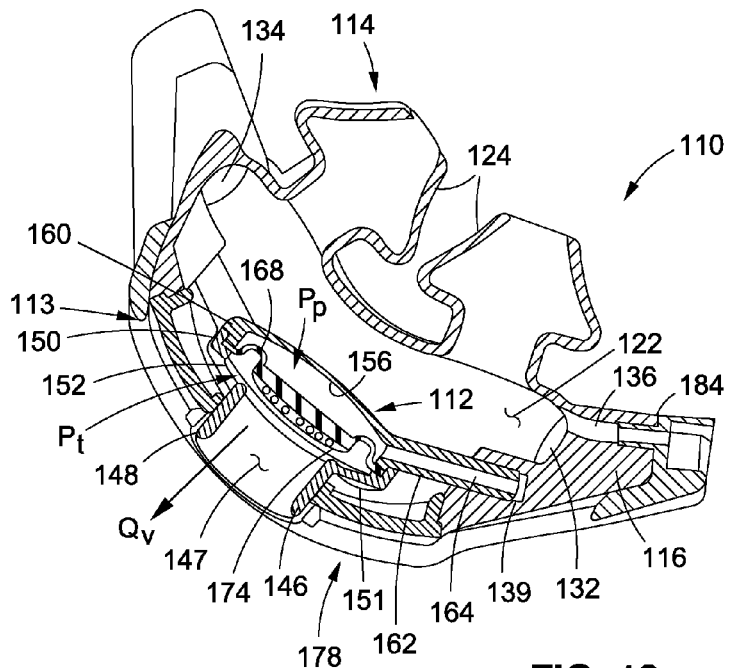
FIG. 18 is a partial cross-sectional view of the nasal pillows mask shown in FIG. 15 taken along lines 18-18 thereof, and depicting the pressure sensing lumen extending through the cushion of the mask.
Figure 19:
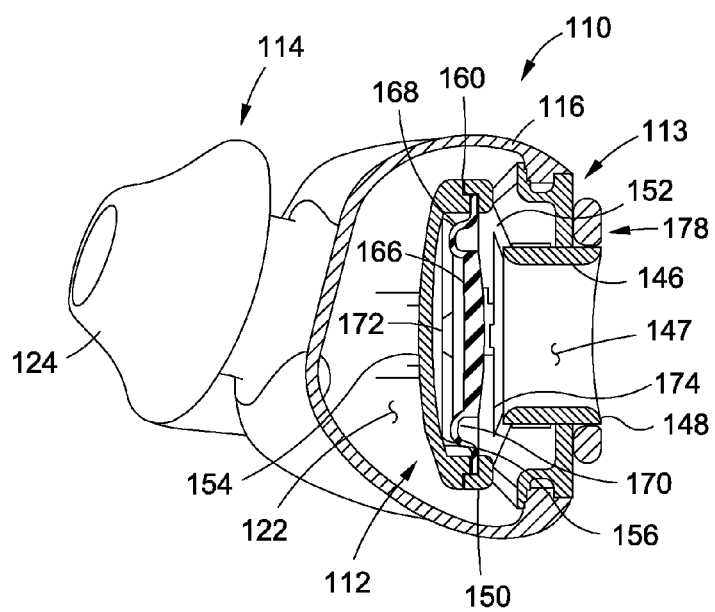
FIG. 19 is a cross-sectional view of the nasal pillows mask shown in FIG. 15 taken along lines 19-19 thereof.
Figure 20:
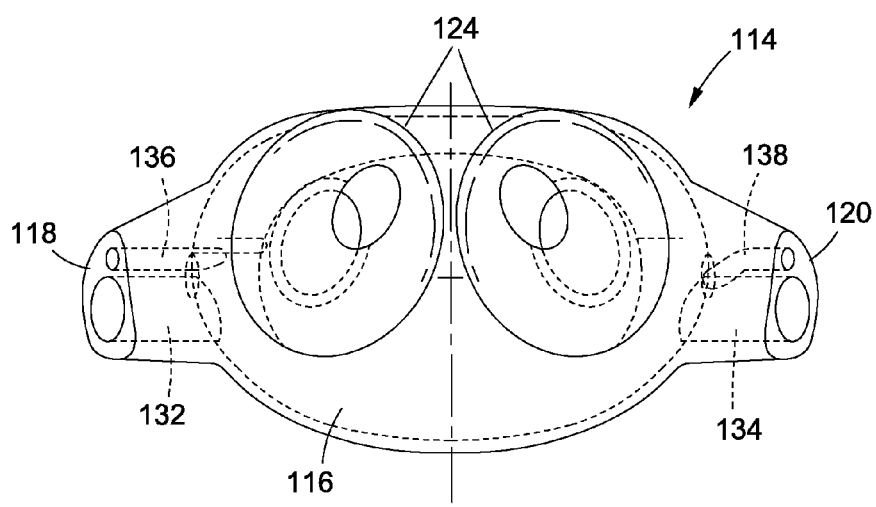
FIG. 20 is a top perspective view of cushion of the nasal pillows mask shown in FIG. 15.
Figure 21:
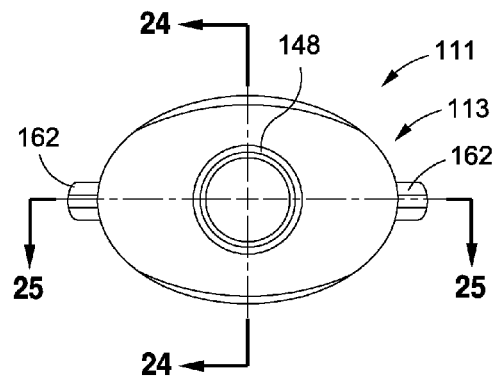
FIG. 21 is a front elevational view of the exhalation valve subassembly for the nasal pillows mask shown in FIG. 15.
Figure 22:
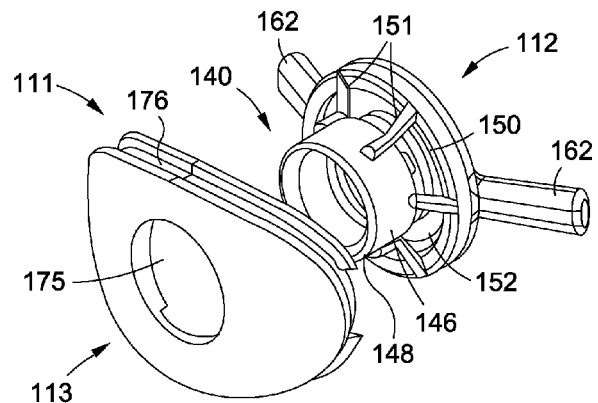
FIG. 22 is a front exploded view of the exhalation valve subassembly shown in FIG. 21, depicting the exhalation valve and the shield plate thereof.
Figure 23:
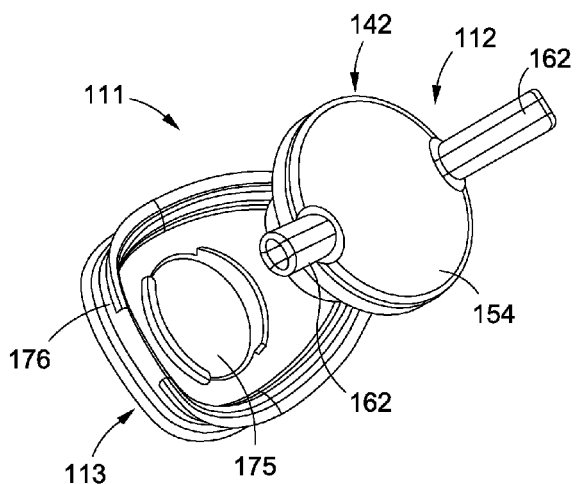
FIG. 23 is a rear exploded view of the exhalation valve subassembly shown in FIG. 21, depicting the exhalation valve and the shield plate thereof.
Figure 24:
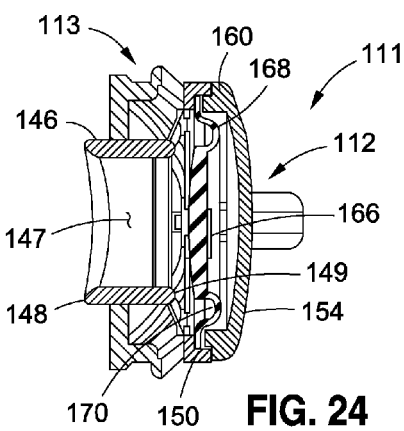
FIG. 24 is a cross-sectional view of the exhalation valve subassembly shown in FIG. 21 taken along lines 24-24 thereof.
Figure 25:
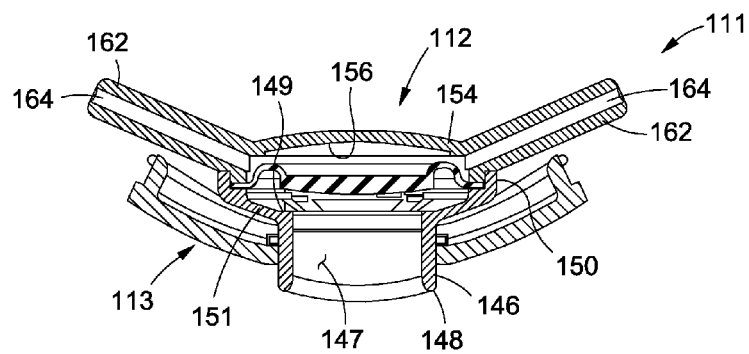
FIG. 25 is a cross-sectional view of the exhalation valve subassembly shown in FIG. 21 taken along lines 25-25 thereof.

The main body portion 116 of the cushion 114 further defines first and second gas delivery lumens 132, 134 which extend from respective ones of the first and second outer end surfaces 118, 120 into fluid communication with the fluid chamber 122. Additionally, a pressure sensing lumen 136 defined by the main body portion 116 extends from the first outer end surface 118 into fluid communication with the fluid chamber 122. The main body portion 116 further defines a valve pilot lumen 138 which extends from the second outer end surface 120 into fluid communication with the fluid chamber. Those of ordinary skill in the art will recognize that the gas delivery lumens 132, 134 may be substituted with a single gas delivery lumen and/or positioned within the cushion 114 in orientations other than those depicted in FIG. 20. For example, the gas delivery lumen(s) of the cushion 114 may be positioned frontally, pointing upwardly, pointing downwardly, etc. rather than extending laterally as shown in FIG. 20. The main body portion 116 of the cushion 114 further includes a mounting aperture 139 formed therein. As seen in FIG. 18, one end of the mounting aperture 139 communicates with the fluid chamber 122, with the opposite end simply terminating blindly within the main body portion 116. The use of the first and second gas delivery lumens 132, 134, the pressure sensing lumen 136, the valve pilot lumen 138 and the mounting aperture 139 will be discussed in more detail below.

Referring now to FIGS. 16-19 and 21-26, the exhalation valve subassembly 111 of the mask 110 comprises the aforementioned exhalation valve 112 in combination with a shield plate 113. The exhalation valve 112 of the mask 110 is itself made of three (3) parts or components, and more particularly a seat member 140, a cap member 142, and a diaphragm 144 which is operatively captured between the seat and cap members 140, 142. The seat and cap members 140, 142 are each preferably fabricated from a plastic material, with the diaphragm 144 preferably being fabricated from an elastomer having a Shore A hardness in the range of from about 20-40.

The seat member 140 includes a tubular, generally cylindrical wall portion 146 which defines a distal, annular outer rim 148 and an opposed annular inner seating surface 149. The wall portion further defines an outlet conduit 147 which extends between the outer rim 148 and seating surface 149. In addition to the wall portion 146, the seat member 140 includes an annular flange portion 150 which is integrally connected to the wall portion 146 by a series of spoke portions 151. The spoke portions 151 extend to locations on the wall portion 146 proximate the seating surface 149, with the flange portion 150 being positioned radially outward relative to the wall portion 146. In the seat member 140, the wall, flange and spoke portions 146, 150, 151 collectively define a plurality of exhaust vents 152 which are located about the periphery of the wall portion 146 in a prescribed arrangement and spacing relative to each other. The seat member 140 is formed such that each of the exhaust vents 152 normally fluidly communicates with the outlet conduit 147 defined by the wall portion 146.

The cap member 142 of the exhalation valve 112 comprises a circularly configured base portion 154 which defines an inner surface 156. In addition to the base portion 154, the cap member 142 includes an annular flange portion 160 which circumvents and protrudes generally perpendicularly relative to the inner surface 156 of the base portion 154. The cap member 142 further includes an identically configured pair of tube portions 162 which are integrally connected to the flange portion 160 in diametrically opposed relation to each other (i.e., approximately 180° apart). Each of the tube portions defines a lumen 164 extending therethrough and is used for reasons which will be discussed in more detail below. The seat and cap members 140, 142, when attached to each other in the fully assembled exhalation valve 112, collectively define an interior valve chamber of the exhalation valve 112, such valve chamber generally being located between the inner surface 156 defined by the base portion 154 of the cap member 142 and the seating surface 149 defined by the wall portion 146 of the seat member 140.

The diaphragm 144 of the exhalation valve 112, which resides within the valve chamber, has a circularly configured, central body portion 166, and a peripheral flange portion 168 which is integrally connected to and circumvents the body portion 166. The flange portion 168 includes an arcuately contoured primary region and a distal region which protrudes radially from the primary region. As such, the primary region of the flange portion 168 extends between the distal region thereof and the body portion 166, and defines a continuous, generally concave channel 170. The body portion 166 of the diaphragm 144 may optionally be perforated, i.e., be provided with an array of small apertures which extend therethrough.

In the exhalation valve 112, the flange portion 168 of the diaphragm 144 is operatively captured between complementary engagement surfaces defined by the flange portions 150, 160 of the seat and cap members 140, 142. More particularly, the annular distal region of the flange portion 168 is compressed (and thus captured) between an annular shoulder defined by the flange portion 160 of the cap member 142, and a complimentary annular shoulder which is defined by the flange portion 150 of the seat member 140 proximate the exhaust vents 152. The orientation of the diaphragm 144 within the valve chamber when captured between the seat and cap members 140, 142 is such that the channel 170 defined by the arcuately contoured primary region of the flange portion 168 is directed toward or faces the seating surface 149 defined by the wall portion 146 of the seat member 140.

The capture of the diaphragm 144 between the seat and cap members 140, 142 in the aforementioned manner results in the diaphragm 144 effectively segregating the valve chamber collectively defined by the seat and cap members 140, 142 into a pilot section 172 and an exhaust section 174. The pilot section 172 of the valve chamber is located between the diaphragm 144 and the inner surface 156 of the base portion 154 of the cap member 142. The exhaust section 174 of the valve chamber is located between the diaphragm 144 and both the exhaust vents 152 and the seating surface 149 of the wall portion 146 of the seat member 140. In this regard, the outlet conduit 147 defined by the wall portion 146 fluidly communicates with the exhaust section 174 of the valve chamber. In addition, the lumens 164 of the tube portions 162 of the cap member 142 each fluidly communicate with the pilot section 172 of the valve chamber.

The diaphragm 144 (and hence the exhalation valve 112) is selectively moveable between an open position (shown in FIGS. 17-19 and 24-25) and a closed position. When in its normal, open position, the diaphragm 144 is in a relaxed, unbiased state. Importantly, in either of its open or closed positions, the diaphragm 144 is not normally seated directly against the inner surface 156 defined by the base portion 154 of the cap member 142. Rather, a gap is normally maintained between the body portion 166 of the diaphragm 144 and the inner surface 156 of the base portion 154. The width of such gap when the diaphragm 144 is in its open position is generally equal to the fixed distance separating the inner surface 156 of the base portion 154 from the shoulder of the flange portion 160 which engages the distal region of the flange portion 168 of the diaphragm 144. Further, when the diaphragm 144 is in its open position, the body portion 166 is itself disposed in spaced relation to the seating surface 149 defined by the wall portion 146 of the seat member 140. As such, when the diaphragm 144 is in its open position, fluid is able to freely pass through the through the exhaust vents 152, between the seating surface 149 and diaphragm 144, and through the outlet conduit 147 defined by the wall portion 146 to ambient air.

In the exhalation valve 112, the diaphragm 144 is resiliently deformable from its open position (to which it may be normally biased) to its closed position. An important feature of the present invention is that the diaphragm 144 is normally biased to its open position which provides a failsafe to allow a patient to inhale ambient air through the exhalation valve 112 and exhale ambient air therethrough (via the exhaust vents 52) during any ventilator malfunction or when the mask 110 is worn without the therapy being delivered by the ventilator. When the diaphragm 144 is moved or actuated to its closed position, the periphery of the body portion 166 is firmly seated against the seating surface 149 defined by the wall portion 146 of the seat member 140. The seating of the body portion 166 of the diaphragm 144 against the seating surface 149 effectively blocks fluid communication between the outlet conduit 147 defined by the wall portion 146 and the exhaust section 174 of the valve chamber (and hence the exhaust vents 152 which fluidly communicate with the exhaust section 174).

Figure 26:
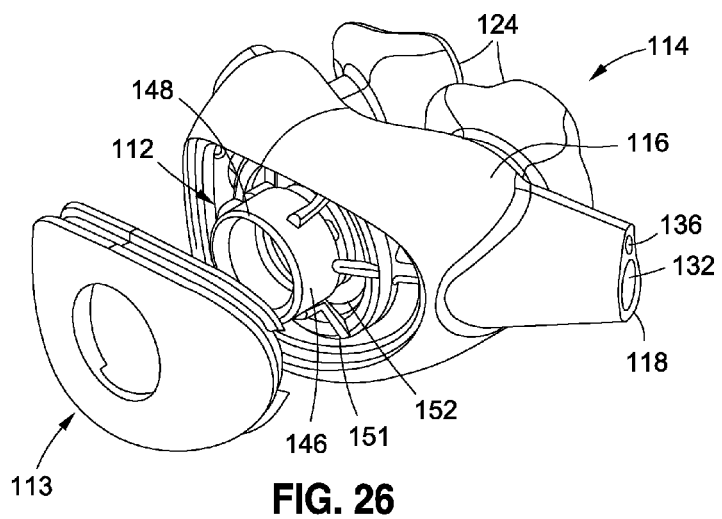
FIG. 26 is a an exploded view of the nasal pillows mask shown in FIG. 15 in a partially assembled state prior to the attachment of the frame member to the cushion, and depicting the separation of the strike plate of the exhalation valve subassembly from the exhalation valve thereof which is positioned within the cushion.

In the mask 110, the cooperative engagement between the exhalation valve 112 and the cushion 114 is facilitated by the advancement of the cap member 142 into the valve opening 126 defined by the cushion 114. Subsequent to such advancement, one of the two tube portions 162 of the cap member 142 is partially advanced into and frictionally retained within the pilot lumen 138 of the cushion 114 in the manner shown in FIG. 17. As is apparent from FIG. 17, the advancement of one tube portion 162 of the cap member 142 into the pilot lumen 138 facilitates the placement of the pilot lumen 138 into fluid communication with the pilot section 172 of the valve chamber via the lumen 164 of the corresponding tube portion 162. The remaining tube portion 162 of the cap member 142 (i.e., that tube portion 162 not advanced into the pilot lumen 138) is advanced into and frictionally retained within the above-described mounting aperture 139 in the manner shown in FIG. 18. Importantly, the resilient construction of the cushion 114, and in particular the main body 116 thereof, allows for the cushion 114 to be bent, twisted or otherwise manipulated as is needed to facilitate the advancement of the tube portions 162 of the cap member 142 into respective ones of the pilot lumen 138 and mounting aperture 139 in the aforementioned manner. The advancement of the tube portions 162 into respective ones of the pilot lumen 138 and mounting aperture 139 causes the exhalation valve 112 to assume a position within the fluid chamber 122 of the cushion 114 as is best shown in FIG. 26. In this regard, the majority of the exhalation valve 112 resides within the fluid chamber 122, with the exception of a small distal section of the wall portion 148 of the seat member 140 which protrudes from the valve opening 126 of the cushion 114.

Due to the positioning of the majority of the exhalation valve 114 within the fluid chamber 122, the exhaust section 174 of the valve chamber is placed into direct fluid communication with the fluid chamber 122 via the exhaust vents 152. Thus, irrespective of whether the diaphragm 144 of the exhalation valve 112 is in its open or closed positions, the pilot lumen 138 of the cushion 114 is maintained in a constant state of fluid communication with the pilot section 172 of the valve chamber. Additionally, irrespective of whether the diaphragm 144 is in its open or closed positions, the fluid chamber 122 is maintained in a constant state of fluid communication with the exhaust section 174 of the valve chamber via the exhaust vents 152. When the diaphragm 144 is in its open position, the fluid chamber 122 is further placed into fluid communication with both the outlet conduit 147 (and hence ambient air) via the open flow path defined between the body portion 166 of the diaphragm 144 and the seating surface 149 of the wall portion 146 of the seat member 140. However, when the diaphragm 144 is moved to its closed position, the fluid communication between the fluid chamber 122 and outlet conduit 147 is effectively blocked by the sealed engagement of the body portion 166 of the diaphragm 144 against the seating surface 149 of the wall portion 146.

As indicated above, in addition to the exhalation valve 112, the exhalation valve subassembly 111 includes the shield plate 113. The shield plate 113 has a generally oval, slightly arcuate profile, and includes a circularly configured opening 175 within the approximate center thereof. Additionally, formed within the peripheral side surface of the shield plate 113 is an elongate groove or channel 176. In the mask 110, the shield plate 113 is adapted to be advanced into the valve opening 126 subsequent to the cooperative engagement of the exhalation valve 112 to the cushion 114 in the aforementioned manner. More particularly, the advancement of the shield plate 113 into the valve opening 126 is facilitated in a manner wherein the wall portion 146 of the seat member 140 is advanced into and through the opening 175 of the shield plate 113. In this regard, the wall portion 146 and the opening 175 have complimentary configurations, with the diameter of the opening 175 only slightly exceeding that of the outer diameter of the wall portion 148.

Subsequent to the advancement of the wall portion 148 into the opening 175, that peripheral edge or lip of the main body 116 of the cushion 114 defining the valve opening 126 is advanced into and firmly seated within the complimentary channel 176 formed in the peripheral side surface of the shield plate 113. The receipt of such edge or lip of the cushion 114 into the channel 176 maintains the shield plate 113 in firm, frictional engagement to the cushion 114. As is seen in FIGS. 17 and 18, the spatial relationship between the exhalation valve 112 and shield plate 113 when each is cooperatively engaged to the cushion 114 in the aforementioned manner is such that the distal section of the wall portion 146 which defines the outer rim 148 thereof protrudes slightly from the exterior surface of the shield plate 113.

As will be recognized, the shield plate 113, when cooperatively engaged to the cushion 114, effectively encloses that portion of the fluid chamber 122 which would otherwise be directly accessible via the valve opening 126. Importantly, by virtue of the attachment of the shield plate 113 to the main body 116 of the cushion 114, virtually the entirety of the exhalation valve 112 is completely enclosed or contained within the fluid chamber 122 of the cushion 114. As indicated above, only a small distal section of the wall portion 146 of the seat member 140 protrudes from the shield plate 113, and in particular the opening 175 defined thereby. As a result, the exhaust vents 152 which facilitate the fluid communication between the fluid chamber 122 and the exhaust section 174 of the valve chamber, and between the fluid chamber 122 and the outlet conduit 147 (and hence ambient air) when the diaphragm 144 is in the open position, are effectively enclosed within the fluid chamber 122 as provides noise attenuation advantages which will be discussed in more detail below.

Figure 15:
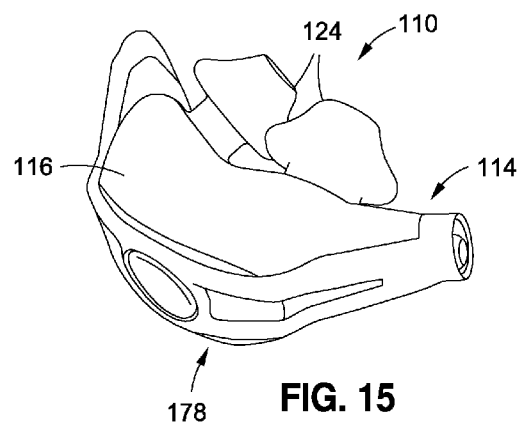
FIG. 15 is top perspective view of a nasal pillows mask constructed in accordance with another embodiment of the present invention and including an integrated diaphragm-based piloted exhalation valve.

To assist in maintaining the cooperative engagement between the exhalation valve subassembly 111 and the cushion 114, the mask 110 is further preferably provided with an elongate reinforcement frame member 178 which is attached to the cushion 114. The frame member 178 has a generally U-shaped configuration, with a central portion thereof including a circularly configured opening 179 formed therein which is adapted to accommodate that aforementioned distal section of the wall portion 146 of the seat member 140 which protrudes from the shield plate 113. In this regard, the diameter of the opening 179 is sized so as to only slightly exceed the outer diameter of the wall portion 146. As seen in FIG. 15, the thickness of the central portion of the frame member 178 is such that when attached to cushion 114 subsequent to the advancement of the wall portion 146 into the complementary opening 179, the outer rim 148 defined by the wall portion 146 is substantially flush or continuous with the exterior surface of the frame member 178.

Figure 17:
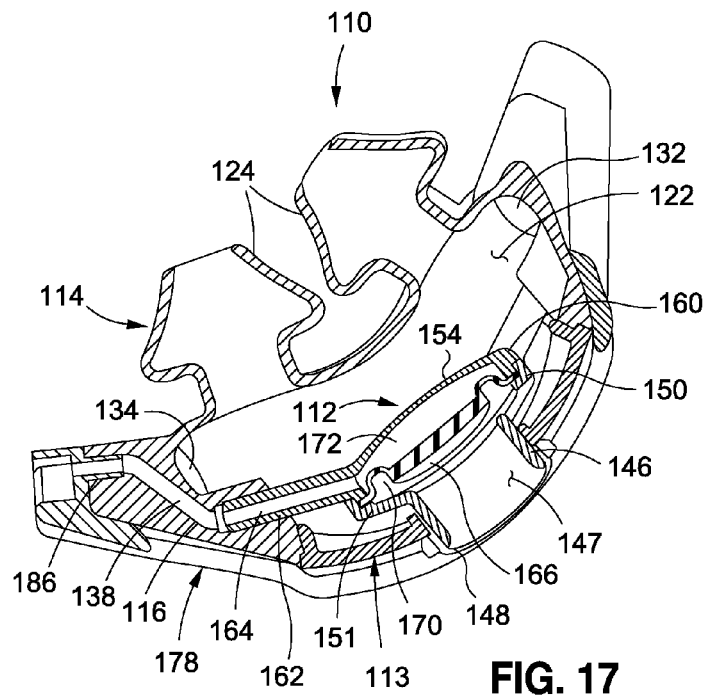
FIG. 17 is a partial cross-sectional view of the nasal pillows mask shown in FIG. 15 taken along lines 17-17 thereof, and depicting the valve pilot lumen extending through the cushion of the mask.

As shown in FIGS. 17 and 18, the opposed end portions of the frame member 178 are cooperatively engaged to respective ones of the first and second outer end surfaces 118, 120 of the cushion 114. More particularly, the frame member 178 includes an identically configured pair of first and second connectors 180, 182 which are formed on respective ones of the opposed end portions thereof. An inner portion of the first connector 180 is advanced into and frictionally retained within the first gas delivery lumen 132 of the cushion 114. Similarly, an inner portion of the second connector 182 is advanced into and frictionally retained within the second gas delivery lumen 134 of the cushion 114. In addition to the inner portions advanced into respective ones of the first and second gas delivery lumens 132, 134, the first and second connectors 180, 182 of the frame member 178 each further include an outer portion which is adapted to be advanced into and frictionally retained within a corresponding lumen of a respective one of a pair of bi-lumen tubes fluidly coupled to the mask 110, in the same manner as described in detail above in relation to the mask 10.

The frame member 178 further includes a tubular, cylindrically configured pressure port 184 which is disposed adjacent the first connector 180. The pressure port 184 is aligned and fluidly communicates with the pressure sensing lumen 136 of the cushion 114. Similarly, the frame member 178 is also provided with a tubular, cylindrically configured pilot port 186 which is disposed adjacent the second connector 182. The pilot port 186 is aligned and fluidly communicates with the valve pilot lumen 138 of the cushion 114. The pressure and pilot ports 184, 186 of the frame member 78 are adapted to be placed into fluid communication with corresponding lumens of respective ones of the aforementioned pair of bi-lumen tubes which are fluidly connected to the mask 110 within a ventilation system incorporating the same, also in the same manner as described in detail above in relation to the mask 10. The receipt of the wall portion 146 of the seat member 140 into the opening 179 of the frame member 178 ensures that the cushion 114, the exhalation valve subassembly 111 and the frame member 178 are properly aligned, and prevents relative movement therebetween.

In the mask 110, the exhalation valve 112 is piloted, with the movement of the diaphragm 144 to the closed position described above being facilitated by the introduction of positive fluid pressure into the pilot section 172 of the valve chamber. More particularly, it is contemplated that during the inspiratory phase of the breathing cycle of a patient wearing the mask 110, the valve pilot lumen 138 will be pressurized by a pilot line fluidly coupled to the pilot port 186, with pilot pressure being introduced into that portion of the pilot section 172 of the valve chamber via the pilot lumen 138 and the lumen 164 of that tube portion 162 of the cap member 142 advanced into the pilot lumen 138. The fluid pressure level introduced into the pilot section 172 of the valve chamber will be sufficient to facilitate the movement of the diaphragm 144 to its closed position described above. When the diaphragm 144 is in its closed position, fluid pressure introduced into the fluid chamber 122 via the gas delivery lumens 136, 138 is prevented from being exhausted to ambient air. In this regard, though such fluid may flow from the fluid chamber 122 into the exhaust section 174 of the valve chamber via the exhaust vents 152, the engagement of the diaphragm 144 to the seating surface 149 defined by the wall portion 146 of the seat member 140 effectively blocks the flow of such fluid into the outlet conduit defined by the wall portion 146 and hence to ambient air.

Conversely, during the expiratory phase of the breathing cycle of the patient wearing the mask 110, it is contemplated that the discontinuation or modulation of the fluid pressure through the valve pilot lumen 138 and hence into the pilot section 172 of the valve chamber, coupled with the resiliency of the diaphragm 144 and/or positive pressure applied to the body portion 166 thereof, will facilitate the movement of the diaphragm 144 back to the open position or to a partially open position. In this regard, positive pressure as may be used to facilitate the movement of the diaphragm 144 to its open position may be provided by air which is exhaled from the patient during the expiratory phase of the breathing circuit and is applied to the body portion 166 of the diaphragm 144 via the pillows portions 124 of the cushion 114, the fluid chamber 122, the exhaust vents 152, and the exhaust section 174 of the valve chamber. As will be recognized, the movement of the diaphragm 144 to the open position allows the air exhaled from the patient into the fluid chamber 122 via the pillow portions 124 to be vented to ambient air after flowing from the fluid chamber 122 into the exhaust section 174 of the valve chamber via the exhaust vents 152, and thereafter flowing from the exhaust section 174 between the diaphragm 144 and seating surface 149 of the wall portion 146 into the outlet conduit 147 also defined by the wall portion 146.

As will be recognized, based on the application of pilot pressure thereto, the diaphragm 144 travels from a fully open position through a partially open position to a fully closed position. In this regard, the diaphragm 144 will be partially open or partially closed during exhalation to maintain desired ventilation therapy. Further, when pilot pressure is discontinued to the diaphragm 144, it moves to an open position wherein the patient can inhale and exhale through the mask 110 with minimal restriction and with minimal carbon dioxide retention therein. This is an important feature of the present invention which allows a patient to wear the mask 110 without ventilation therapy being applied to the mask 110, the aforementioned structural and functional features of the mask 110 making it more comfortable to wear, and further allowing it to be worn without carbon dioxide buildup. This feature is highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 110, during patient inhalation, the valve pilot lumen 138 is pressurized, which causes the diaphragm 144 to close against the seating surface 149, thus effectively isolating the fluid chamber 122 of the mask 110 from the outside ambient air. The entire flow delivered from a flow generator fluidly coupled to the mask 110 is inhaled by the patient, assuming that unintentional leaks at the interface between the cushion 114 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 138 is controlled so that the exhaled flow from the patient can be exhausted to ambient air through the exhalation valve 112 in the aforementioned manner. In this regard, the pilot pressure is "servoed" so that the position of the diaphragm 144 relative to the seating surface 149 is modulated, hence modulating the resistance of the exhalation valve 112 to the exhaled flow and effectively ensuring that the pressure in the fluid chamber 122 of the mask 110 is maintained at a prescribed therapeutic level throughout the entire length of the exhalation phase. When the valve pilot lumen 138 is not pressurized, the exhalation valve 112 is in a normally open state, with the diaphragm 144 being spaced from the seating surface 149 in the aforementioned manner, thus allowing the patient to spontaneously breathe in and out with minimal pressure drop (also referred to as back-pressure) in the order of less than about 2 cm H2O at 60 l/min. As a result, the patient can comfortably breathe while wearing the mask 110 and while therapy is not being administered to the patient. Importantly, the effective containment of the exhaust vents 152 within the fluid chamber 122 substantially mitigates or suppresses the noise generated by the mask 110 attributable to the flow of fluid into the exhaust section 174 of the valve chamber via the exhaust vents 152.

Those of ordinary skill in the art will recognize that the functionality of the exhalation valve 112 during use of the mask 110 by a patient can be characterized with the same three parameters described above in relation to the mask 10 and shown in FIGS. 11A, 11B and 11C. However, based on the structural features of the exhalation valve 112 in comparison to the exhalation valve 12, the parameters Pt which is the treatment pressure (i.e., the pressure in the mask 110 used to treat the patient; Pp which is the pilot pressure (i.e., the pressure used to pilot the diaphragm 144 in the exhalation valve 112); and Qv which is vented flow (i.e., flow that is exhausted from inside the exhalation valve 112 to ambient are labeled in FIG. 18 as Pt, Pp and Qv in the context of the exhalation valve 112. As such, when the patient is ventilated, Pt is greater than zero, with the functionality of the exhalation valve 112 being described by the family of curves in the first and second quadrants of FIG. 11A. In this regard, as apparent from FIG. 11A, for any given Pt, it is evident that by increasing the pilot pressure Pp, the exhalation valve 112 will close and the vented flow will decrease. A decrease in the pilot pressure Pp will facilitate the opening of the exhalation valve 112, thereby increasing vented flow. The vented flow will increase until the diaphragm 144 touches or contacts the inner surface 156 of the base portion 154 of the cap member 142, and is thus not able to open further. Conversely, when the patient is not ventilated, the inspiratory phase can be described by the third and fourth quadrants. More particularly, Qv is negative and air enters the mask 110 through the exhalation valve 112, with the pressure Pt in the mask 110 being less than or equal to zero. Pilot pressure Pp less than zero is not a configuration normally used during ventilation of the patient, but is depicted for a complete description of the functionality of the exhalation valve 112. The family of curves shown in FIG. 11A can be described by a parametric equation. Further, the slope and asymptotes of the curves shown in FIG. 11A can be modified by, for example and not by way of limitation, changing the material used to fabricate the diaphragm 144, changing the thickness of the diaphragm 144, changing the area ratio between the side of the diaphragm 144 facing the pilot section 172 and the side facing the exhaust section 174, changing the clearance between the diaphragm 144 and the seating surface 149, and/or changing the geometry of the exhaust vents 152.

As also discussed above in relation to the mask 10, an alternative representation of the functional characteristics of the valve 112 can be described by graphs in which $\Delta P = Pt - Pp$ is shown. For example, the graph of FIG. 11B shows that for any given Pt, the vented flow can be modulated by changing $\Delta P$. In this regard, $\Delta P$ can be interpreted as the physical position of the diaphragm 144. Since the diaphragm 144 acts like a spring, the equation describing the relative position d of the diaphragm 144 from the seating surface 149 of the seat member 140 is $k \cdot d + Pt \cdot At = Pp \cdot Ap$, where At is the area of the diaphragm 144 exposed to treatment pressure Pt and Ap is the area of the diaphragm 144 exposed to the pilot pressure Pp. A similar, alternative representation is provided in the graph of FIG. 11C which shows Pt on the x-axis and $\Delta P$ as the parameter. In this regard, for any given $\Delta P$, the position d of the diaphragm 144 is determined, with the exhalation valve 112 thus being considered as a fixed opening valve. In this scenario Pt can be considered the driving pressure pushing air out of the exhalation valve 112, with FIG. 11C further illustrating the highly non-linear behavior of the valve 112.

The mask 110 may also be integrated into each of the above-described ventilation systems 88, 100 in substitution for the mask 10. In this regard, as will be recognized by those of ordinary skill in the art, the first and second bi-lumen tubes 96, 98 of such ventilation systems 88, 100 would simply be cooperatively engaged to corresponding ones of the first and second connectors 180, 182, pressure port 184 and pilot port 186 of the frame member 178 in the same manner described above regarding the engagement to the first and second connectors 80, 82, pressure port 84 and pilot port 86 of the frame member 78.

In the mask 110, it is contemplated that exhalation vale subassembly 111, and in particular the exhalation valve 112, may be detached from the cushion 114 and removed from within the fluid chamber 122 as needed for periodic cleaning or replacement thereof. As will be recognized, such removal is facilitated by first detaching the shield plate 113 from the cushion 114 by removing the lip of the cushion 114 defining the valve opening 126 from within the channel 176 of the shield plate 113. Thereafter, the exhalation valve 112 is simply grasped and pulled from within the fluid chamber 122, the flexibility/resiliency of the cushion 114 allowing for the easy removal of the tube portions 162 of the cap member 142 from within respective ones of the pilot lumen 138 and mounting aperture 139. The re-attachment of the exhalation valve subassembly 111 to the cushion 114 occurs in the reverse sequence, the exhalation valve 112 being advanced into the fluid chamber 122 and attached to the cushion 114 in the aforementioned manner prior to the attachment of the shield plate 113 to the cushion 114 in the aforementioned manner.

Figure 27:
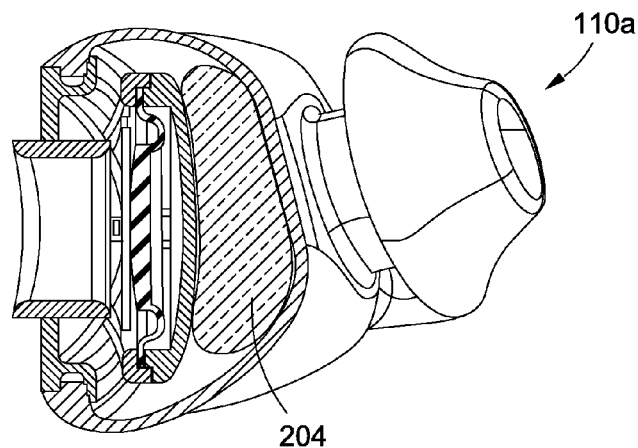
FIG. 27 is a cross-sectional view similar to FIG. 19, but depicting a variant of the nasal pillows mask shown in FIG. 15 wherein an HME is integrated into the cushion thereof.
Figure 28:
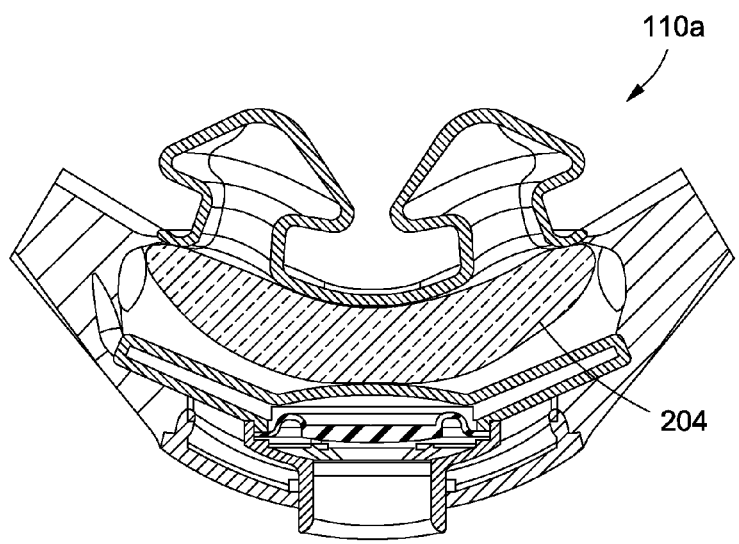
FIG. 28 is a cross-sectional view similar to FIGS. 17 and 18, but depicting a variant of the nasal pillows mask shown in FIG. 15 wherein an HME is integrated into the cushion thereof.

Referring now to FIGS. 27 and 28, there is shown a mask 110a which comprises a variant of the mask 110. The sole distinction between the masks 110, 110a lies in the mask 110a including a heat and moisture exchanger or HME 204 which is positioned within the fluid chamber 122 of the cushion 114. The HME 204 is operative to partially or completely replace a humidifier (cold or heated pass-over; active or passive) which would otherwise be fluidly coupled to the mask 110a. This is possible because the average flow through the system envisioned to be used in conjunction with the mask 110a is about half of a prior art CPAP mask, due to the absence of any intentional leak in such system.

The HME 204, as a result of its positioning within the fluid chamber 122, is able to interact with the flow delivered from the flow generator to the patient in order to humidify it, and is further able to capture humidity and heat from exhaled flow for the next breath. The pressure drop created by the HME 204 during exhalation (back-pressure) must be limited, in the order of less than 5 cmH2O at 60l/min, and preferably lower than 2 cmH2O at 60l/min. These parameters allow for a low back-pressure when the patient is wearing the mask 110a and no therapy is delivered to the patient.

It is contemplated that the HME 204 can be permanently assembled to the cushion 114, or may alternatively be removable therefrom and thus washable and/or disposable. In this regard, the HME 204, if removable from within the cushion 114, could be replaced on a prescribed replacement cycle. As will be recognized, the removal of the HME 204 from within the fluid chamber 122 would follow the detachment of the exhalation valve subassembly 111 from the cushion 114 in the manner described above. Similarly, the placement of the HME 204 back into the fluid chamber 122 would precede the reattachment of the exhalation valve subassembly 111 to the cushion 114 in the manner also described above. Additionally, it is contemplated that the HME 204 can be used as an elastic member that adds elasticity to the cushion 114. In this regard, part of the elasticity of the cushion 114 may be attributable to its silicone construction, and further be partly attributable to the compression and deflection of the HME 204 inside the cushion 114.

The integration of the exhalation valve 12, 112 into the cushion 14, 114 and in accordance with the present invention allows lower average flow compared to prior art CPAP masks. As indicated above, normal masks have a set of apertures called "vents" that create a continuous intentional leak during therapy. This intentional leak or vented flow is used to flush out the exhaled carbon dioxide that in conventional CPAP machines, with a standard ISO taper tube connecting the mask to the flow generator or blower, fills the tubing up almost completely with carbon dioxide during exhalation. The carbon dioxide accumulated in the tubing, if not flushed out through the vent flow, would be inhaled by the patient in the next breath, progressively increasing the carbon dioxide content in the inhaled gas at every breath. The structural/functional features of the exhalation valve 12, 112, in conjunction with the use of small inner diameter, high pneumatic resistance tubes in the system in which the mask 10, 10a, 110, 110a is used, ensures that all the exhaled gas goes to ambient. As a result, a vent flow is not needed for flushing any trapped carbon dioxide out of the system. Further, during inspiration the exhalation valve 12, 112 can close, and the flow generator of the system needs to deliver only the patient flow, without the additional overhead of the intentional leak flow. In turn, the need for lower flow rates allows for the use of smaller tubes that have higher pneumatic resistance, without the need for the use of extremely powerful flow generators. The pneumatic power through the system can be kept comparable to those of traditional CPAP machines, though the pressure delivered by the flow generator will be higher and the flow lower.

The reduced average flow through the system in which the mask 10, 10a, 110, 110a is used means that less humidity will be removed from the system, as well as the patient. Conventional CPAP systems have to reintegrate the humidity vented by the intentional leak using a humidifier, with heated humidifiers being the industry standard. Active humidification introduces additional problems such as rain-out in the system tubing, which in turn requires heated tubes, and thus introducing more complexity and cost into the system. The envisioned system of the present invention, as not having any intentional leak flow, does not need to introduce additional humidity into the system. As indicated above, the HME 104, 204 can be introduced into the cushion 14, 114 of the mask 10a, 110a so that exhaled humidity can be trapped and used to humidify the air for the following breath.

In addition, a big portion of the noise of conventional CPAP systems is noise conducted from the flow generator through the tubing up to the mask and then radiated in the ambient through the vent openings. As previously explained, the system described above is closed to the ambient during inhalation which is the noisiest part of the therapy. The exhaled flow is also lower than the prior art so it can be diffused more efficiently, thus effectively decreasing the average exit speed and minimizing impingement noise of the exhaled flow on bed sheets, pillows, etc.

As also explained above, a patient can breathe spontaneously when the mask 10, 10a, 110, 100a is worn and not connected to the flow generator tubing, or when therapy is not administered. In this regard, there will be little back pressure and virtually no carbon dioxide re-breathing, due to the presence of the exhalation valve 12, 112 that is normally open and the inner diameters of the tubes integrated into the system. This enables a zero pressure start wherein the patient falls asleep wearing the mask 10, 10a, 110, 110a wherein the flow generator does not deliver any therapy. Prior art systems can only ramp from about 4 mH2O up to therapy pressure. A zero pressure start is more comfortable to patients that do not tolerate pressure.

Figure 14:
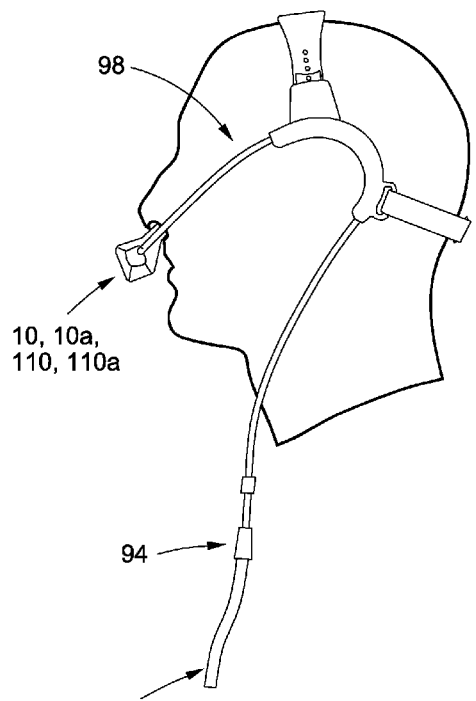
FIG. 14 is a side-elevational view of any nasal pillows mask constructed in accordance with the present invention as cooperatively engagement in an exemplary manner to a patient through the use of a headgear assembly.

As seen in FIG. 14, due to the reduced diameter of the various tubes (i.e., the tri-lumen tube 90 and bi-lumen tubes 96, 98, 102) integrated into the system 88, 100, such tubes can be routed around the patient's ears similar to conventional O2 cannulas. More particularly, the tubing can go around the patient's ears to hold the mask 10, 10a, 110, 110a to the patient's face. This removes the "tube drag" problem described above since the tubes will not pull the mask 10, 10a away from the face of the patient when he or she moves. As previously explained, "tube drag" typically decreases mask stability on the patient and increases unintentional leak that annoys the patient. In the prior art, head gear tension is used to counter balance the tube drag, which leads to comfort issues. The tube routing of the present invention allows for lower head gear tension and a more comfortable therapy, especially for compliant patients that wear the mask 10, 10a, 110, 110a approximately eight hours every night. The reduction in tube drag in accordance with the present invention also allows for minimal headgear design (virtually none), reduced headgear tension for better patient comfort as indicated above, and reduced cushion compliance that results in a smaller, more discrete cushion 14, 114. The tube dangling in front of the patient, also commonly referred to as the "elephant trunk" by patients, is a substantial psychological barrier to getting used to therapy. The tube routing shown in FIG. 14, in addition to making the mask 10, 10a, 110, 110a more stable upon the patient, avoids this barrier as well. Another benefit to the smaller tubing is that the mask 10, 10a, 110, 110a can become smaller because it does not need to interface with large tubing. Indeed, large masks are another significant factor leading to the high non-compliance rate for CPAP therapy since, in addition to being non-discrete, they often cause claustrophobia.

Figures 29, 30:
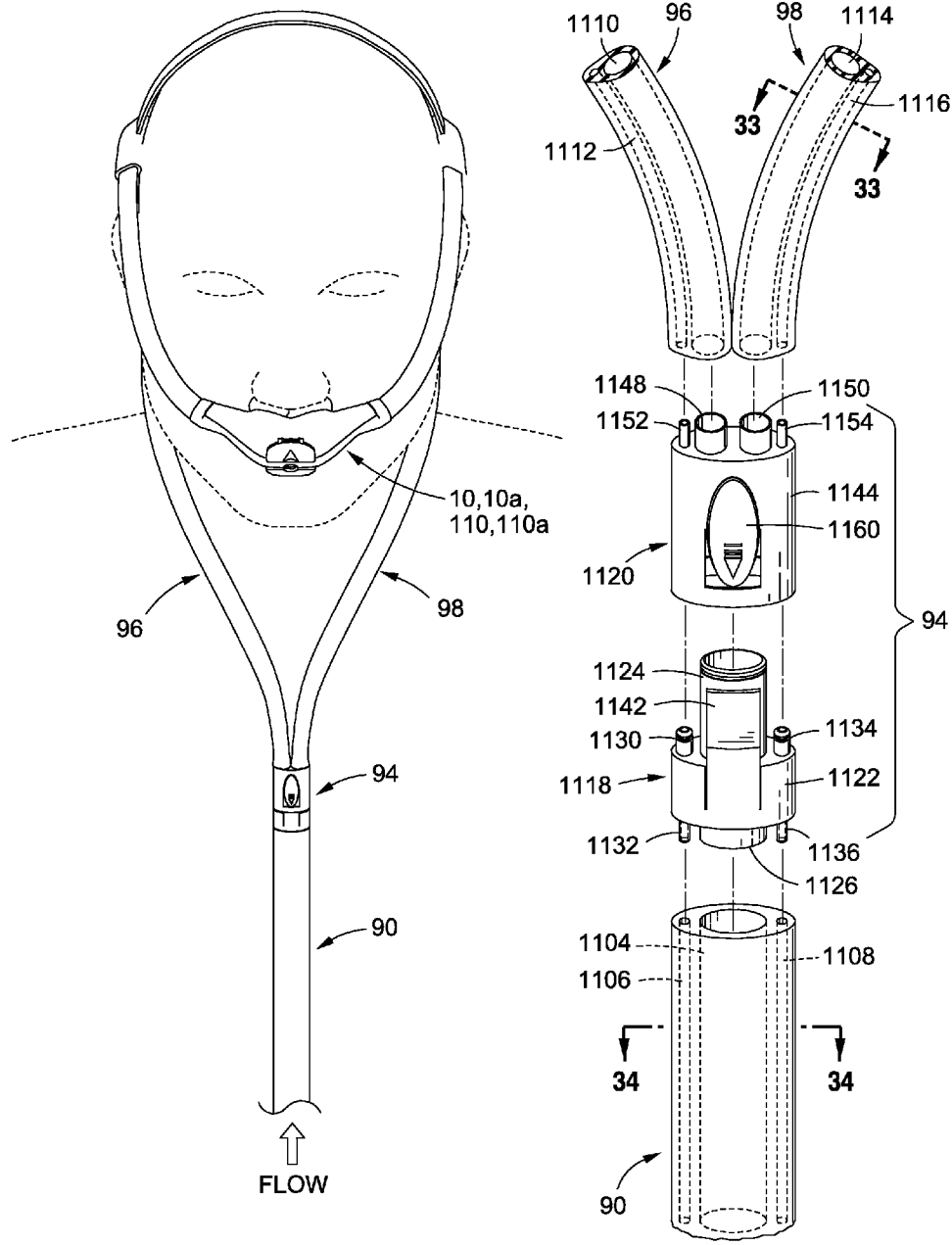
FIG. 29 is a front-elevational view depicting an exemplary tri-lumen tube, Y-connector, and pair of bi-lumen tubes which are used to collectively facilitate the operative interface between any nasal pillows mask constructed in accordance with the present invention and a flow generating device in accordance with the schematic representation shown in FIG. 12.
FIG. 30 is an exploded view of the tri-lumen tube, Y-connector and bi-lumen tubes shown in FIG. 29.

Referring now to FIG. 29, there is shown a front-elevational view of the nasal pillows mask 10, 10a, 110, 110a of the present invention wherein an exemplary tri-lumen tube 90, Y-connector 94, and pair of bi-lumen tubes 96, 98 are used to collectively facilitate the operative interface between the nasal pillows mask 10, 10a, 110, 110a and a flow generating device 92 in accordance with the schematic representation of the ventilation system 88 shown in FIG. 12. As indicated above, in the ventilation system 88, the tri-lumen tube 90 is used to facilitate the fluid communication between the Y-connector 94 and the blower or flow generator 92 of the system 88, with one end of the tri-lumen tube 90 being fluidly connected to the flow generator 92, and the opposite end thereof being fluidly connected to the Y-connector 94.

As is best seen in FIGS. 30, 34 and 35, the tri-lumen tube 90 has a ribbon-like, generally elliptical or oval cross-sectional configuration, and defines three (3) lumens, along with a lengthwise cross-sectional axis A1 and a widthwise cross-sectional axis A2, both of which are shown in FIG. 34. More particularly, the tri-lumen tube 90 includes a gas delivery lumen 1104, a pressure sensing lumen 1106, and a pilot lumen 1108. As best seen in FIG. 34, like the tri-lumen tube 90, the gas delivery lumen 1104 has a generally elliptical profile or cross-sectional configuration. Along these lines, the gas delivery lumen 1104 is preferably formed so as to have a maximum length L in the range of from about 5 ft. to 10 ft., and preferably about 6 ft.; a maximum width W in the range of from about 8 mm to 13 mm; and a cross-sectional area equivalent to a circular lumen with a diameter of about 2 mm to 15 mm, and preferably about 4 mm to 10 mm, and most preferably about 8 mm. The pressure sensing and pilot lumens 1106, 1108 are disposed proximate respective ones of the ends of the gas delivery lumen 1104 along the axis A1. However, both the pressure sensing and pilot lumens 1106, 1108 each have a generally circular cross-sectional configuration, as opposed to an elliptical cross-sectional configuration. As is further apparent from FIGS. 30, 34 and 35, the cross-sectional area of the gas delivery lumen 1104 substantially exceeds that of each of the pressure sensing and pilot lumens 1106, 1108, which are preferably identically sized to each other, and are each provided with an inner diameter or ID in the range of from about 0.5 mm to 2 mm. The tri-lumen tube 90 is preferably fabricated from a silicone, TPE or PVC material which has a Shore Hardness in the range of from about 50A to 80A, and thus possesses a prescribed level of resilience and flexibility.

The structural features of the tri-lumen tube 90, coupled with the material properties thereof, are selected to not only make it resiliently flexible, but to prevent either of the pressure sensing or pilot lumens 1106, 1108 from being collapsed by even an above-normal level of bending, twisting or other deflection of the tri-lumen tube 90. In this regard, the elliptical cross-sectional configurations of the tri-lumen tube 90 and its gas delivery lumen 1104, coupled with the orientation of the pressure sensing and pilot lumens 1106, 1108 adjacent respective ones of the opposed ends thereof (along of the lengthwise cross-sectional axis A1), imparts to the tri-lumen tube 90 a tendency to bend in a direction which is generally perpendicular to, rather than aligned with or parallel to the axis A1 (similar to the bending of a ribbon). This manner of bending, which is generally along the axis A2, substantially reduces the susceptibility of the pressure sensing or pilot lumens 1106, 1108 to inadvertent collapse. Thus, even if the tri-lumen tube 90 is bent beyond that threshold which would typically be encountered during normal use of ventilation system 88 as could result in the collapse or blockage of the gas delivery lumen 1104, flow will typically still be maintained through both the pressure sensing and pilot lumens 1106, 1108. This unobstructed fluid or pneumatic communication through the pressure sensing and pilot lumens 1106, 1108 provides a modality which, in concert with the control algorithms of the ventilation system 88, may be used to facilitate not only the actuation of the exhalation valve 12, 112 in a manner ensuring unhindered patient breathing through the mask 10, 10a, 110, 110a but also the sounding of an alarm within the ventilation system 88 and/or adjustment to other operational parameters thereof as are necessary to address the blockage or obstruction of the gas delivery lumen 1104.

As indicated above, the structural attributes of the Y-connector 94, which will be described in more detail below, effectively bifurcates the tri-lumen tube 90 into the first and second bi-lumen tubes 96, 98, each of which is of a prescribed length. As best seen in FIGS. 33, 36 and 37, the first and second bi-lumen tubes 96, 98 are identically configured to each other, and each have a generally tear-drop shaped cross-sectional configuration defining an apex 1119. The first bi-lumen tube 96 includes a gas delivery lumen 1110 and a pressure sensing lumen 1112. Similarly, the second bi-lumen to 98 includes a gas delivery lumen 1114 and a pilot lumen 1116.

In both the first and second bi-lumen tubes 96, 98, the gas delivery lumens 1110, 1114 each have a generally elliptical cross-sectional configuration or profile, as is most easily seen in FIG. 33. The elliptical cross-sectional area is equivalent to that of a circular lumen having a diameter in the range of from about 1 mm to 10 mm, and preferably about 3 mm to 6 mm, and most preferably about 5 mm. However, the pressure sensing and pilot lumens 1112, 1116 each have a generally circular cross-sectional configuration or profile, with an inner diameter or ID in the range of from about 0.5 mm to 2 mm. Each bi-lumen tube 96, 98 is preferably fabricated from a silicone, TPE or PVC material which has a Shore Hardness in the range of from about 50A to 80A, and thus possesses a prescribed level of resilience and flexibility. The advantages attendant to forming each of the gas delivery lumens 1110, 1114 of the first and second bi-lumen tubes 96, 98 with a generally elliptical profile will be discussed more detail below.

In the exemplary ventilation system 88, the gas delivery lumen 1110 of the first bi-lumen tube 96 is fluidly coupled to the generally cylindrical, tubular outer portion of the first connector 80, 180 of the frame number 78, 178. The pressure sensing lumen 1112 of the first bi-lumen tube 96 is itself fluidly coupled to the generally cylindrical, tubular outer portion of the pressure port 84, 184 of the frame number 78, 178 which, as indicated above, is disposed immediately adjacent the outer portion of the first connector 80, 180. As will be recognized, the pressure sensing lumen 1112 is sized relative to the outer portion of the pressure port 84, 184 such that the pressure port 84, 184 is frictionally maintained within the first bi-lumen tube 96 once advanced into a corresponding end of the pressure sensing lumen 1112 thereof. Similarly, the gas delivery lumen 1110 is sized relative to the outer portion of the first connector 80, 180 such that the first connector 80, 180 is frictionally retained within the first bi-lumen tube 96 once advanced into a corresponding end of the gas delivery lumen 1110.

Similar to the first bi-lumen tube 96, the gas delivery lumen 1114 of the second bi-lumen tube 98 is fluidly coupled to the generally cylindrical, tubular outer portion of the second connector 82, 182 of the frame number 78, 178. The pilot lumen 1116 of the second bi-lumen tube 98 is itself fluidly coupled to the generally cylindrical, tubular outer portion of the pilot port 86, 186 of the frame number 78, 178 which, as indicated above, is disposed immediately adjacent the outer portion of the second connector 82, 182. As will be recognized, the pilot lumen 1116 is sized relative to the outer portion of the pilot port 86, 186 such that the pilot port 86, 186 is frictionally maintained within the second bi-lumen tube 98 once advanced into a corresponding end of the pilot lumen 1116 thereof. Similarly, the gas delivery lumen 1114 is sized relative to the outer portion of the second connector 82, 182 such that the second connector 82, 182 is frictionally retained within the second bi-lumen tube 98 once advanced into a corresponding end of the gas delivery lumen 1114.

As seen in FIG. 36, whereas the outer portion of each of the first and second connectors 80, 180 and 82, 182 has a generally circular cross-sectional configuration, the gas delivery lumens 1110, 1114 of the first and second bi-lumen tubes 96, 98 each have a generally elliptical cross-sectional configuration or profile as indicated above. In the ventilation system 88, the relative orientations of the outer portions of the first connector 80, 180 and pressure port 84, 184 are the same as those of the outer portions of second connector 82, 182 and pilot port 86, 186. Similarly, the relative orientations of the gas delivery and pressure sensing lumens 1110, 1112 of the first bi-lumen tube 96 are the same as the gas delivery and pilot lumens 1114, 1116 of the second bi-lumen tube 98. In the ventilation system 88, these relative orientations are specifically selected so as to achieve a prescribed offset between the axis of the outer portions of the first and second connectors 80, 180 and 82, 182 and corresponding ones of the gas delivery lumens 1110, 1114 when the outer portions of the pressure and pilot ports 80, 180 and 82, 182 are coaxially aligned with respective ones of the pressure sensing and pilot lumens 1112, 1116 of the first and second bi-lumen tubes 96, 98. As a result of these offsets, the advancement of the outer portions of the first and second connectors 80, 180 and 82, 182 into corresponding ends of respective ones of the gas delivery lumens 1110, 1114 facilitates the resilient deformation of each of the first and second bi-lumen tubes 96, 98 in a matter effectively compressing a web portion 1121 thereof. As seen in FIGS. 33, 36 and 37, this web portion 1121 is disposed between the gas delivery lumen 1110, 1114 and a corresponding one the pressure sensing and pilot lumens 1112, 1116. Such compression of the web portion 1121 effectively maintains a tight frictional engagement between the first and second bi-lumen tubes 96, 98 and the outer portions of respective ones of the first and second connectors 80, 180 and 82, 182 which is less prone to leakage.

The structural features of the first and second bi-lumen tubes 96, 98, coupled with the material properties thereof, are selected to not only to provide resilient flexibility, but to prevent either of the pressure sensing or pilot lumens 1112, 1116 from being collapsed by even an above-normal level of bending, twisting or other deflection of the corresponding bi-lumen tube 96, 98. In this regard, the elliptical or tear drop shaped cross-sectional configuration of each bi-lumen tube 96, 98, coupled with the orientation of the corresponding pressure sensing or pilot lumen 1112, 1116 between the gas delivery lumen 1110, 1114 and the apex 1119 thereof, substantially reduces the susceptibility of the pressure sensing or pilot lumens 1112, 1116 to inadvertent collapse. Thus, even if the first or second bi-lumen tube 96, 98 is bent beyond that threshold which would typically be encountered during normal use of ventilation system 88 as could result in the collapse or blockage of the corresponding gas delivery lumen 1110, 1114, flow will typically still be maintained through both the pressure sensing and pilot lumens 1112, 1116. As with the tri-lumen tube 90 described above, this unobstructed flow through the pressure sensing and pilot lumens 1112, 1116 provides a modality which, in concert with the control algorithms of the ventilation system 88, may be used to facilitate not only the actuation of the exhalation valve 12, 112 in a manner ensuring unhindered patient breathing through the mask 10, 10a, 110, 110a but also the sounding of an alarm within the ventilation system 88 and/or adjustment to other operational parameters thereof as are necessary to address the blockage or obstruction of either gas delivery lumen 1110, 1114.

Referring now to FIGS. 29-32 and 35, as indicated above, in the ventilation system 88 the Y-connector 94 facilitates the operative interface between the tri-lumen tube 90 and the first and second bi-lumen tubes 96, 98. More particularly, the Y-connector 94 effectively divides the gas delivery lumen 1104 of the tri-lumen tube 90 into the gas delivery lumens 1110, 1114 of the first and second bi-lumen tubes 96, 98.

Advantageously, the Y-connector 94 is adapted to allow for the selective disconnection or de-coupling of the tri-lumen tube 90 from the first and second bi-lumen tubes 96, 98 without disconnecting or separating either the tri-lumen tube 90 or either of the first and second bi-lumen tubes 96, 98 from the Y-connector 94. In this regard, the Y-connector 94 comprises a male member 1118 and a complimentary female member 1120 which are releasably engageable to each other. The male member 1118 includes a base portion 1122 which has a generally elliptical or oval-shaped cross-sectional configuration. In this regard, the cross-sectional length and width dimensions of the base portion 1122 along the lengthwise and widthwise major axes thereof are preferably equal or substantially equal to those of the tri-lumen tube 90.

In addition to the base portion 1122, the male member 1118 includes first and second tube portions 1124, 1126 which protrude from respective ones of the opposed sides or faces of the base portion 1122. Like the base portion 1122, the first and second tube portions 1124, 1126 each have a generally elliptical or oval-shaped cross-sectional configuration. The height of the first tube portion 1124 exceeds that of the second tube portion 1126. Additionally, the cross-sectional length and width dimensions of the second tube portion 1126 are sized so as to slightly exceed those of the gas delivery lumen 1104 of the tri-lumen tube 90. Such relative sizing is selected such that the second tube portion 1126 may be advanced into yet tightly frictionally maintained within one end of the gas delivery lumen 1104. The advancement of the second tube portion 1126 into the gas delivery lumen 1104 is typically limited by the abutment of the corresponding end of the tri-lumen tube 90 against that end or face of the base portion 1122 having the second tube portion 1126 protruding therefrom. As will be recognized, due to the maximum cross-sectional length and width dimensions of the base portion 1122 preferably being equal or substantially equal to those of the tri-lumen tube 90, the outer surface of the base portion 1122 will be substantially flush or continuous with the outer surface of the tri-lumen tube 90 when the corresponding ends are abutted against each other in the aforementioned manner. In the male member 1118, the base portion 1122 and the first and second tube portions 1124, 1126 collectively define a gas delivery lumen 1128 which is most easily seen in FIG. 35.

The male member 1118 further comprises first and second pressure sensing ports 1130, 1132 which protrude from respective ones of the opposed sides or faces of the base portion 1122, and first and second pilot ports 1134, 1136 which also protrude from respective ones of the opposed sides or faces of the base portion 1122. In this regard, the first and second pressure sensing ports 1130, 1132 are coaxially aligned with each other, as are the first and second pilot ports 1134, 1136.

In the male member 1118, the first pressure sensing and pilot ports 1130, 1134 are identically configured to each other, with the second pressure sensing and pilot ports 1132, 1136 being identically configured to each other as well. Though the first and second pressure sensing ports 1130, 1132 and the first and second pilot ports 1134, 1136 each have tubular, generally cylindrical configurations with generally circular cross-sectional profiles, the outer diameters of the first pressure sensing and pilot ports 1130, 1134 exceed those of the second pressure sensing and pilot ports 1132, 1136. As is best seen in FIG. 35, the first and second pressure sensing ports 1130, 1132 and the base portion 1122 collectively define a pressure sensing lumen 1138 of the male member 1118. Similarly, the first and second pilot lumens 1134, 1136 and the base portion 1122 collectively define a pilot lumen 1140 of the male member 1118.

As is most apparent from FIG. 30, the first pressure sensing and pilot ports 1130, 1134 are oriented so as to be disposed adjacent respective ones of the opposed ends of the first tube portion 1124 along the lengthwise cross-sectional axis thereof. Similarly, the second pressure sensing and pilot ports 1132, 1136 are positioned adjacent respective ones of the opposed ends of the second tube portion 1126 along the lengthwise cross-sectional axis thereof. Importantly, the orientation of the second pressure sensing and pilot ports 1132, 1136 relative to the second tube portion 1126 is such that when the second tube portion 1126 is coaxially aligned with the gas delivery lumen 1104 of the tri-lumen tube 90, the second pressure sensing and pilot ports 1132, 1136 will be coaxially aligned with respective ones of the pressure sensing and pilot lumens 1106, 1108 of the tri-lumen tube 90. As such, when the second tube portion 1126 is advanced into the gas delivery lumen 1104 in the aforementioned manner, the second sensing port 1132 will concurrently be advanced into one end of the pressure sensing lumen 1106, with the second pilot port 1136 being concurrently advanced into one end of the pilot lumen 1108. Along these lines, the outer diameter dimensions of the second pressure sensing and pilot ports 1132, 1136 are preferably sized relative to the inner diameter dimensions of the pressure sensing and pilot lumens 1106, 1108 such that the second pressure sensing and pilot ports 1132, 1136 are tightly frictionally retained within respective ones of the pressure sensing and pilot lumens 1106, 1108 upon being fully advanced therein.

As is best seen in FIGS. 30-32, the male member 1118 further includes an opposed, juxtaposed pair of locking tabs 1142 which protrude from the base portion 1122 and extend along the first tube portion 1124. More particularly, the locking tabs 1142 are positioned on opposite sides of the first tube portion 124 so as to extend in generally perpendicular relation to the widthwise cross-sectional axis thereof. As will be described in more detail below, the locking tabs 1142 are used to facilitate the releasable engagement of the male member 1118 to the female member 1120. As will also be described in more detail below, the locking tabs 1142 may be identically configured to each other, or may alternatively have dissimilar configurations for purposes of insuring that the male and female members 1118, 1120 are in prescribed orientations relative to each other as a precursor to being releasably engaged to each other.

The female member 1120 of the Y-connector 94 comprises a main body portion 1144 which itself has a generally elliptical or oval-shaped cross-sectional configuration. In this regard, the cross-sectional length and width dimensions of the body portion 1144 along the lengthwise and widthwise major axes thereof are preferably equal or substantially equal to those of the base portion 1122 of the male member 1118, as well as the tri-lumen tube 90. As best seen in FIGS. 31 and 35, the body portion 1144 defines an elongate passage 1146 which extends generally axially therein to one of the opposed sides or faces thereof.

In addition to the body portion 1144, the female member 1120 includes an identically configured pair of first and second gas delivery ports 1148, 1150 which protrude from a common side or face of the body portion 1144, and in particular that side opposite the side having the passage 1146 extending thereto. The first and second gas delivery ports 1148, 1150 each have a tubular, generally cylindrical configuration with a generally circular cross-sectional profile. Additionally, the first and second gas delivery ports 1148, 1150 each fluidly communicate with one end of the passage 1146.

The female member 1120 further comprises a pressure sensing port 1152 and a pilot port 1154 which are identically configured to each other, and protrude from that side or face of the body portion 1144 having the first and second gas delivery ports 1148, 1150 protruding therefrom. More particularly, the pressure sensing port 1152 is disposed between the first gas delivery port 1148 and one of the opposed ends of the body portion 1144 along the lengthwise cross-sectional axis thereof. Similarly, the pilot port 1154 is disposed between the second gas delivery port 1150 and one of the opposed ends of the body portion 1144 along the lengthwise cross-sectional axis thereof. The pressure sensing and pilot ports 1152, 1154 also each have a tubular, generally cylindrical configuration with a generally circular cross-sectional profile. As is best seen in FIG. 35, the pressure sensing port 1152 and the body portion 1144 collectively define a pressure sensing lumen 1156 of the female member 1120. Similarly, the pilot port 1154 and the body portion 1144 collectively define a pilot lumen 1158 of the female member 1120.

The first gas delivery port 1148 of the female member 1120 is adapted to be advanced into one end of the gas delivery lumen 1110 of the first bi-lumen tube 96, with the second gas delivery port 1150 being adapted for advancement into one end of the gas delivery lumen 1114 of the second bi-lumen tube 98. However, whereas the first and second gas delivery ports 1148, 1150 each have a generally circular cross-sectional configuration, the gas delivery lumens 1110, 1114 of the first and second bi-lumen tubes 96, 98 each have the generally elliptical cross-sectional configuration or profile as indicated above. In the ventilation system 88, the relative orientations of the first gas delivery port 1148 and the pressure sensing port 1152 are the same as those of the first connector 80, 180 and pressure port 84, 184 of the mask 10, 10a, 110, 110a. Similarly, the relative orientations of the second gas delivery port 1150 and pilot port 1154 are the same as those of the second connector 82, 182 and pilot port 86, 186 of the mask 10, 10a, 110, 110a. As with the connection of the first and second bi-lumen tubes 96, 98 to the mask 10, 10a, 110, 110a as explained above, these relative orientations are specifically selected so as to achieve a prescribed offset between the axes of the first and second gas delivery ports 1148, 1150 and corresponding ones of the gas delivery lumens 1110, 1114 when the pressure sensing port 1152 is coaxially aligned with the pressure sensing lumen 1112 of the first bi-lumen tube 96, and the pilot port 1154 is coaxially aligned with the pilot lumen 1116 of the second bi-lumen tube 98. As a result of these offsets, the advancement of the first and second gas delivery ports 1148, 1150 into corresponding ends of respective ones of the gas delivery lumens 1110, 1114 facilitates the resilient deformation of each of the first and second bi-lumen tubes 96, 98 in a manner effectively compressing the web portion 1121 thereof. Such compression of the web portion 1121 effectively maintains a tight frictional engagement between the first and second bi-lumen tubes 96, 98 and respective ones of the first and second gas delivery ports 1148, 1150 which is less prone to leakage.

The advancement of the first gas delivery port 1148 into the gas delivery lumen 1110, as well as the advancement of the second gas delivery port 1150 into the gas delivery lumen 1114, is limited by the abutment of the corresponding ends of the first and second bi-lumen tubes 96, 98 against that end or face of the body portion 1144 having the first and second gas delivery ports 1148, 1150, as well as the pressure sensing and pilot ports 1152, 1154, protruding therefrom. As will be recognized, when the first gas delivery port 1148 is advanced into the gas delivery lumen 1110 in the aforementioned manner, the pressure sensing port 1152 is concurrently advanced into one end of the pressure sensing lumen 1112. Similarly, when the second gas delivery port 1150 is advanced into the gas delivery lumen 1114, the pilot port 1154 will concurrently be advanced into one end of the pilot lumen 1116. Along these lines, the outer diameter dimensions of the pressure sensing and pilot ports 1152, 1154 are preferably sized relative to the inner diameter dimensions of the pressure sensing and pilot lumens 1112, 1116 such that the pressure sensing and pilot ports 1152, 1154 are tightly frictionally retained within respective ones of the pressure sensing and pilot lumens 1112, 1116 upon being fully advanced therein.

As best seen in FIGS. 30 and 31, the female member 1120 further includes an opposed pair of retention tabs 1160 which are formed in and extend partially along the body portion 1144. More particularly, the retention tabs 1160 are positioned on opposite sides of the body portion 1144 so as to extend in generally perpendicular relation to the widthwise cross-sectional axis thereof. As will also be described in more detail below, the retention tabs 1160 are sized and configured to be releasably engageable to respective ones of the locking tabs 1142 to facilitate the releasable engagement of the male member 1118 to female member 1120. As with the locking tabs 1142, the retention tabs 1160 may be identically configured to each other, or may alternatively have dissimilar configurations for purposes of ensuring that that the male and female members 1118, 1120 are in prescribed orientations relative to each other as a precursor to being releasably engaged to each other.

In FIGS. 30-32, the male and female members 1118, 1120 of the Y-connector 94 are depicted in a disconnected or separated state. When the male member 1118 is disconnected from the female member 1120, the gas delivery lumens 1110, 1114 of the first and second bi-lumen tubes 96, 98 each still fluidly communicate with the passage 1146 of the female member 1120 via respective ones of the first and second gas delivery ports 1148, 1150. In addition, the pressure sensing lumen 1112 of the first bi-lumen tube 96 still fluidly communicates with the pressure sensing lumen 1156, with the pilot lumen 1116 of the second bi-lumen tube 98 still fluidly communicating with the pilot lumen 1158. Further, the gas delivery lumen 1128 of the male member 1118 still fluidly communicates with the gas delivery lumen 1104 of the tri-lumen tube 90 via the second tube portion 1126, with the pressure sensing lumen 1138 still fluidly communicating with the pressure sensing lumen 1106 and the pilot lumen 1140 still fluidly communicating with the pilot lumen 1108.

The connection of the male and female members 1118, 1120 to each other is facilitated by initially advancing both the first tube portion 1124 and the locking tabs 1142 of the male member 1118 into the passage 1146 of the female member 1120 which has a complementary shape adapted to accommodate both the first tube portion 1124 and the locking tabs 1142. The orientation of the first pressure sensing and pilot ports 1130, 1134 of the male member 1118 relative to the first tube portion 1124 is such that the coaxial alignment of the first tube portion 1124 with the passage 1146 facilitates the concurrent coaxial alignment of the first pressure sensing port 1130 with the pressure sensing lumen 1156 and the coaxial alignment of the first pilot port 1134 with the pilot lumen 1158. Along these lines, the full advancement of the first tube portion 1124 and locking tabs 1142 into the passage 1146 results in the concurrent advancement of the first pressure sensing port 1130 into the pressure sensing lumen 1156, and the first pilot port 1134 into the pilot lumen 1158. As is best seen in FIG. 35, those end portions of the pressure sensing and pilot lumens 1156, 1158 extending to the side or face of the body portion 1144 having the open end of the passage 1146 extending thereto are each slightly enlarged relative to the remainder thereof. These enlarged end portions of the pressure sensing and pilot lumens 1156, 1158 are adapted to accommodate respective ones of the first pressure sensing and pilot ports 1130, 1134 which, as indicated above, are slightly larger than corresponding ones of the second pressure sensing and pilot ports 1132, 1136.

As will be recognized, the full advancement of the first tube portion 1124 and locking tabs 1142 into the passage 1146, and advancement of the first pressure sensing and pilot ports 1130, 1134 into respective ones of the pressure sensing and pilot lumens 1156, 1158 is limited by the abutment of that side or face of the body portion 1144 of the female member 1120 opposite that having the first and second gas delivery ports 1148, 1150 protruding therefrom against that side or face of the base portion 1120 of the male member 1118 having the first tube portion 1124 protruding therefrom. At the point of such abutment, the locking tabs 1142 will releasably engage respective ones of the retention tabs 1160 in a manner maintaining the male and female members 1118, 1120 in releasable engagement to each other.

Each of the retention tabs 1160 is sized and configured to be resiliently flexible. Based on the complementary shapes of the locking tabs 1142 and retention tabs 1160, the application of compressive pressure to each of the retention tabs 1160 when the male and female members 1118, 1120 are cooperatively engaged to each other facilitates the disengagement of the retention tabs 1160 from respective ones of the locking tabs 1142 as allows for the separation of the male and female members 1118, 1120 from each other. In the ventilation system 88, it is important that the male and female members 1118, 1120 not be cross-connected as could result in the pressure sensing lumen 1138 of the male member 1118 being placed into fluid communication with the pilot lumen 1150 of the female member 1120, and the pilot lumen 1140 of the male member 1118 being placed into fluid communication with the pressure sensing lumen 1156 of the female member 1120. To prevent such occurrence, as indicated above, it is contemplated that the locking tabs 1142 and/or the retention tabs 1160 of each pair may be provided with dissimilar configurations as ensures that the male and female members 1118, 1120 can only be releasably connected to each other in one prescribed orientation relative to each other. As will be recognized, such orientation ensures that the pressure sensing lumens 1138, 1156 are properly placed into fluid communication with each other, as are the pilot lumens 1140, 1158.

As is best seen in FIG. 35, the full receipt of the first tube portion 1124 of the male member 1118 into the passage 1146 of the female member 1120 facilitates the placement of the gas delivery lumen 1128 into fluid communication with a segment of the passage 1146, as well as each of the first and second gas delivery lumens 1148, 1150 which each fluidly communicate with the passage 1146. Similarly, the complete advancement of the first pressure sensing and pilot ports 1130, 1134 of the male member 1118 into respective ones of the pressure sensing and pilot lumens 1156, 1158 of the female member 1120 effectively places the pressure sensing and pilot lumens 1138, 1140 of the male member 1118 into fluid communication with respective ones of the pressure sensing and pilot lumens 1156, 1158 of the female member 1120. Thus, when the male and female members 1118, 1120 of the Y-connector 94 are releasably connected to each other in the aforementioned manner, the gas delivery lumen 1104 of the tri-lumen tube 90 is effectively bifurcated or divided, and thus placed into fluid communication with the gas delivery lumens 1110, 1114 of the first and second bi-lumen tubes 96, 98 via the gas delivery lumen 1128 of the male member 1118, a segment of the passage 1146 of the female member 1120, and each of the first and second gas delivery ports 1148, 1150 of the female member 1120. In addition, the pressure sensing lumen 1106 of the tri-lumen tube 90 is placed into fluid communication with the pressure sensing lumen 1112 of the first bi-lumen tube 96 by the pressure sensing lumen 1138 of the male member 1118 and the pressure sensing lumen 1156 of the female member 1120. Similarly, the pilot lumen 1108 of the tri-lumen tube 90 is placed into fluid communication with the pilot lumen 1116 of the second bi-lumen tube 98 via the pilot lumen 1140 of the male member 1118 and the pilot lumen 1158 of the female member 1120. Though not shown with particularity in FIGS. 30-32 and 35, it is contemplated that the Y-connector 94, and in particular the male and female members 1118, 1120 thereof, may be outfitted with sealing members such as O-rings as needed to facilitate the formation of fluid-tight seals between the same when releasably connected to each other.

Figures 38, 39:
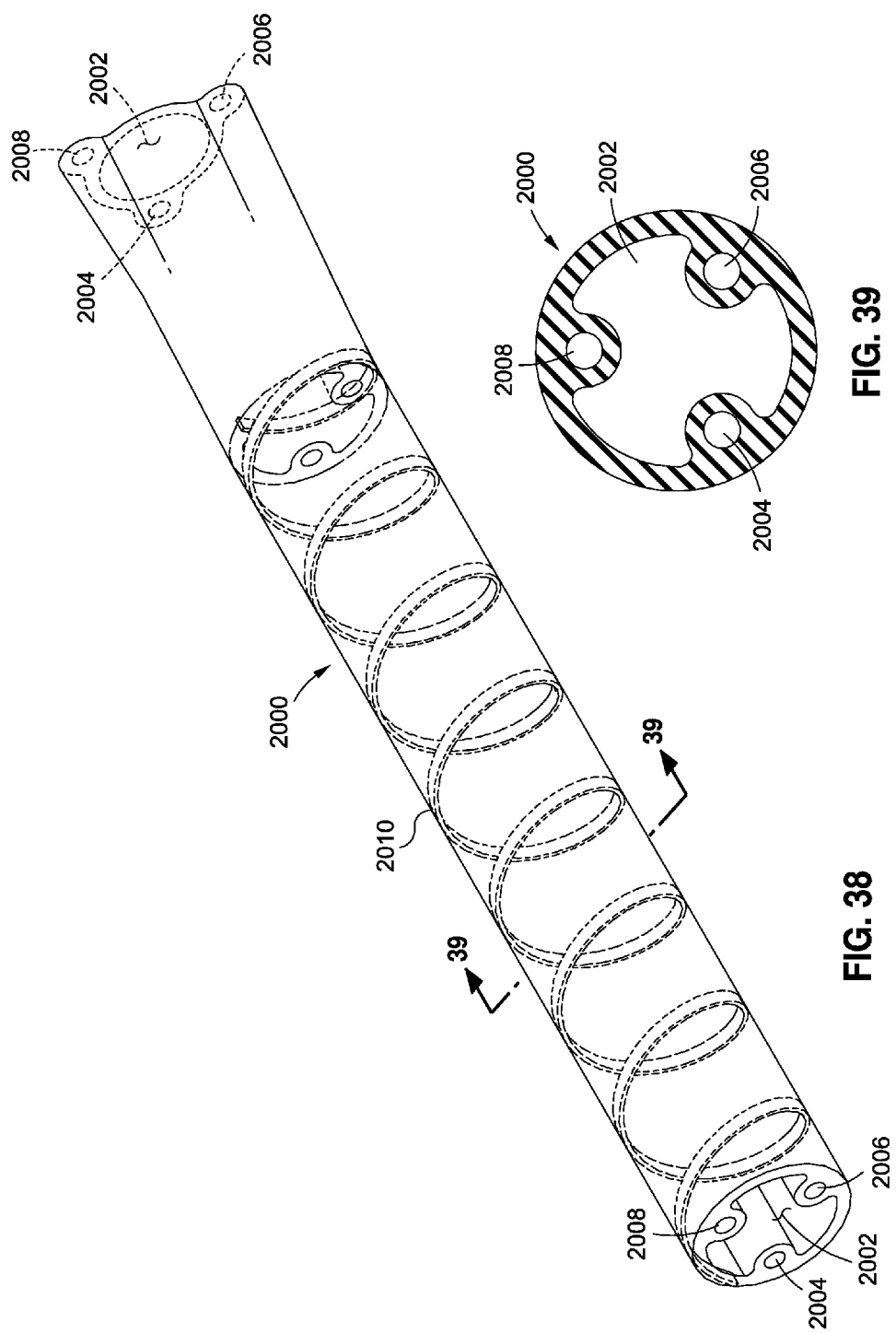
FIG. 38 is a perspective view of a segment of a quad-lumen tube which may be used an alternative to the tri-lumen tube shown in FIGS. 29-30 and 34-35.
FIG. 39 is a cross-sectional view of the quad-lumen tube taken along line 39-39 of FIG. 38.

Referring now to FIGS. 38 and 39, there is depicted a portion of a quad-lumen tube 2000 which may be integrated into the ventilation system 88 as an alternative to the above-described tri-lumen tube 90. The quad-lumen tube 2000 has a generally circular, cross-sectional configuration, and defines four (4) lumens. More particularly, the quad-lumen tube 2000 includes a gas delivery lumen 2002, a pressure sensing lumen 2004, a pilot lumen 2006, and an auxiliary lumen 2008. The pressure sensing, pilot and auxiliary lumens 2004, 2006, 2008 are preferably disposed about the gas delivery lumen 2002 in equidistantly spaced intervals of approximately 120°, and have identically dimensioned, generally circular cross-sectional configurations.

As is apparent from FIGS. 38 and 39, the cross-sectional configuration of the quad-lumen tube 2000 is not uniform along the entire length thereof. Rather, each of the opposed end portions of the quad-lumen tube 190 (one of which is shown in FIG. 38) have cross-sectional configurations differing from that the central section or portion of the quad-lumen tube 2000 extending between such end portions. More particularly, as seen in FIG. 39, the gas delivery lumen 2002 defined by the central portion of the quad-lumen tube 2000 extending between the end portions thereof does not have a generally circular cross-sectional configuration. Rather, portions of the quad-lumen tube 2000 which accommodate respective ones of the pressure sensing, pilot and auxiliary lumens 2004, 2006, 2008 protrude into the gas delivery lumen 2002, thus imparting a generally cloverleaf cross-sectional configuration thereto. In contrast, at each of the opposed end portions of the quad-lumen tube 2000, those portions of the quad-lumen tube 2000 accommodating respective ones of the pressure sensing, pilot and auxiliary lumens 2004, 2006, 2008 transition to the exterior of the gas delivery lumen 2002, thus resulting in such gas delivery lumen 2002 assuming a generally circular cross-sectional configuration. Those of ordinary skill in the art will recognize that the quad-lumen tube 2000 may be formed so as not to include the aforementioned alternatively configured end portions, the non-circular cross-sectional configuration of the central portion of the gas delivery lumen 2002 thus being consistent throughout the entire length of the quad-lumen tube 2000. However, if the alternatively configured end portions are provided, it is contemplated that they may be formed through the implementation of a specialized extrusion process, or as separate parts which are glued or molded onto the aforementioned central portion of the quad-lumen tube 2000. In the quad-lumen tube 2000, it is also contemplated that the inner diameters of each of the pressure sensing, pilot and auxiliary lumens 2004, 2006, 2008 will be similar to those of the pressure sensing and pilot lumens 1106, 1108 of the tri-lumen tube 90 as described above, with the cross-sectional area of the gas delivery lumen 2002 being similar to that of the gas delivery lumen 1104 of the tri-lumen tube 90 as also described above.

As will be recognized by those of ordinary skill in the art, providing the gas delivery lumen 2002 with a generally circular cross-sectional configuration or profile at each of the opposed end portions of the quad-lumen tube 2000 makes it easier to couple or operatively interface the quad-lumen tube 2000 to a Y-connector at one end thereof, and to a flow generator at the opposite end thereof. Along these lines, the circularly configured end portions of the gas delivery lumen 2002 are more easily advanced over and frictionally retained upon a cylindrically configured port, as opposed to a port that would otherwise need to be provided in a non-standard configuration so as to be capable of advancement into the gas delivery lumen 2002 having the shape shown in FIG. 39. In the quad-lumen tube 2000, the auxiliary lumen 2008 may be used, for example, to route optical fibers or wires as could potentially be used to illuminate the Y-connector. Assuming such Y-connector has a two-piece, detachable construction as described above in relation to the Y-connector 94, the illumination thereof would provide greater ease to a patient to effectuate the disconnection of the male and female members from each other at night, in darkness.

The quad-lumen tube 2000 is preferably fabricated from a silicone, TPE or PVC material which has a Shore Hardness in the range of from about 50A to about 80A, and thus possesses a prescribed level of resilience and flexibility. Further, as seen in FIG. 38, it is contemplated that the wall of the quad-lumen tube 2000 defining or partially defining the gas delivery lumen 2002 will have a spiral-shaped reinforcement ribbon 2010 embedded therein. It is contemplated that such ribbon 2010 will extend along the central portion of the quad-lumen tube 2000, but not into either of the alternatively configured end portions thereof. The ribbon 2010 enhances the structural integrity of the quad-lumen tube 2000, thus making the gas delivery, pressure sensing and pilot lumens 2002, 2004, 2006 less susceptible to collapse upon any excessive bending or compression of the quad-lumen tube 2000. It is also contemplated that the ribbon 2010 could be substituted with a reinforcement braiding which is adapted to enhance the structural integrity of the quad-lumen tube 2000 in the aforementioned manner. However, those or ordinary skill in the art will recognize that the quad-lumen tube 2000 need necessarily have the ribbon 2010 or other type of reinforcement braiding integrated therein. Along these lines, it is also contemplated that the quad-lumen tube 2000 could further be alternatively configured such that the pressure sensing, pilot and auxiliary lumens 2004, 2006, 2008 assume a generally helical profile along the length thereof, thus mimicking the effect of the effect of the ribbon 2010, and assisting in the prevention of the kinking or collapse of the quad-lumen tube 2000. Also, though not shown, it is contemplated that a reinforcement ribbon similar to the ribbon 2010 or reinforcement braiding may be integrated into the above-described tri-lumen tube 90.

Figures 40, 41:
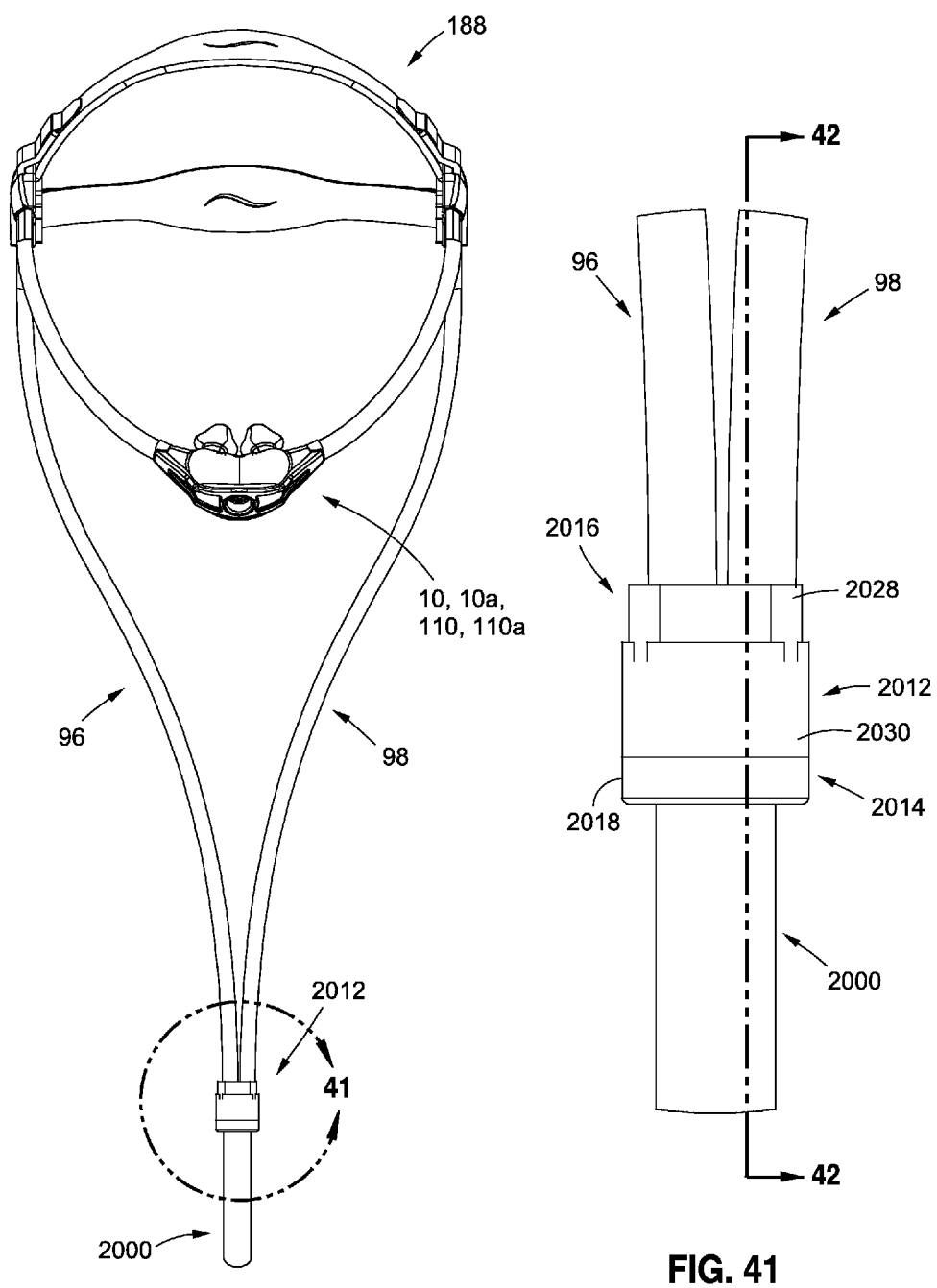
FIG. 40 is a front-elevational view depicting the operative interface between any nasal pillows mask constructed in accordance with the present invention and a flow generating device in accordance with the schematic representation shown in FIG. 12 using the quad-lumen tube of FIGS. 38-39 in combination with a corresponding, complimentary Y-connector and the bi-lumen tubes shown in FIGS. 29-30, 33 and 35-37.
FIG. 41 is an enlargement of the encircled region 41 shown in FIG. 40.

Referring now to FIGS. 40-46, there is shown in FIG. 40 a ventilation system 188 similar to the ventilation system 88 shown in FIGS. 12 and 29, but wherein the quad-lumen tube 2000 is substituted for the above-described tri-lumen tube 90. In this regard, the use of the above-described quad-lumen tube 2000 in the ventilation system 188 in conjunction with the mask 10, 10a, 110, 110a necessitates that a Y-connector 2012 be used as an alternative to the above-described Y-connector 94 to facilitate the operative interface between the quad-lumen tube 2000 and the first and second bi-lumen tubes 96, 98. As will be described in more detail below, the Y-connector 2012, among other things, effectively divides the gas delivery lumen 2002 of the quad-lumen tube 2000 into the gas delivery lumens 1110, 1114 of the first and second bi-lumen tubes 96, 98.

Advantageously, the Y-connector 2012 is adapted to allow for the selective disconnection or de-coupling of the quad-lumen tube 2000 from the first second bi-lumen tubes 96, 98 without disconnecting or separating either the quad-lumen tube 2000 or either of the first and second bi-lumen tubes 96, 98 from the Y-connector 2012. In this regard, the Y-connector 2012 comprises a male member 2014 and a complimentary female member 2016 which are releasably engageable to each other. The Y-connector 2012 is preferably used in conjunction with that version of the quad-lumen tube 2000 described above which does not include the outwardly flared opposed end portions. Rather, in the quad-lumen tube 2000 used in conjunction with the Y-connector 2012, the cross-sectional profile of the quad-lumen tube 2000 is that which is shown in FIG. 39 along the entire length thereof.

As seen in FIGS. 42-46, the male member 2014 has a generally annular, sleeve-like configuration defining a first portion 2018 which is of a first outer diameter and transitions into a second portion 2020 which is of a second outer diameter less than the first outer diameter. In this regard, the first and second portions 2018, 2020 are separated from each other by a continuous, annular shoulder 2022. As most easily seen in FIG. 42, formed within the outer surface of the second portion 2020 is a continuous groove or channel which is disposed in relative close proximity to the shoulder 2022 and accommodates a complimentary O-ring 2024. The O-ring 2024 protrudes slightly outwardly beyond the outer surface of the second portion 2020, and is used for reasons which will be described in more detail below. Also formed in the second portion 2020 of the male member 2014 is an alignment slot 2026. More particularly, the alignment slot 2026 extends to the distal end or rim defined by the second portion 2020, and terminates at approximately the O-ring 2024. The use of the slot 2026 will also be described in more detail below.

Figure 42:
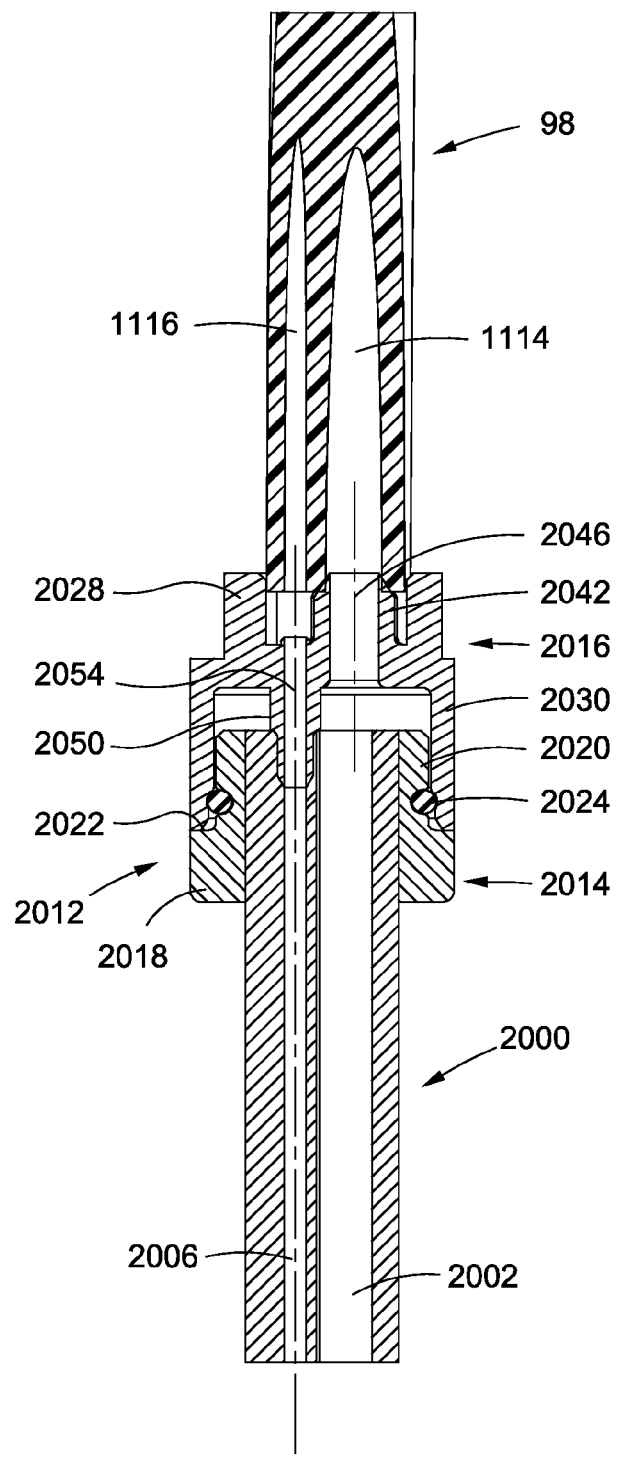
FIG. 42 is a cross-sectional view taken along line 42-42 of FIG. 41.

As is further shown in FIG. 42, the male member 2014 of the Y-connector 2012 is advanced over and frictionally engaged to that end portion of the quad-lumen tube 2000 opposite that which is fluidly connected to the flow generator 92 included in the exemplary ventilation system 188. More particularly, the male member 2014 is oriented such that the distal end of the quad-lumen tube 2000 is substantially flush or continuous with the distal end or rim defined by the reduced diameter second portion 2020 of the male member 2014.

The female member 2016 of the Y-connector 2012 comprises a base portion 2028 which has a generally tear-drop shaped configuration. Integrally connected to the base portion 2028 is an annular sleeve portion 2030 which has a generally circular cross-sectional configuration. The base and sleeve portions 2028, 2030 collectively define a hollow cavity 2032 of the female member 2016. Disposed within the inner wall or surface of the sleeve portion 2030 is a continuous groove or channel 2034. The channel 2034 is sized and configured to accommodate that portion of the O-ring 2024 which protrudes from the outer surface of the second portion 2020 of the male member 2014 when the male and female members 2014, 2016 are releasably engaged to each other in a manner which will be described in more detail below. Also formed on the inner wall or surface of the sleeve portion 2030 proximate the channel 2034 is an alignment tab 2035, the size and shape of which is complimentary to that of the slot 2026 which is formed within the second portion 2020 of the male member 2014. is a continuous groove or channel 2034. In this regard, the slot 2026 is sized and configured to accommodate the tab 2035 when the male and female members 2014, 2016 are releasably engaged to each other.

As is most easily seen in FIG. 46, formed in the base portion 2028 of the female member 2016 in side-by-side relation to each other is an identically configured pair of first and second openings 2036, 2038, each of which has a generally tear-drop shaped profile which is complimentary to the cross-sectional configuration of each of the first and second bi-lumen tubes 96, 98. The female member 2016 further includes an identically configured pair of first and second gas delivery ports 2040, 2042 which are each formed on the base portion 2028 within respective ones of the first and second openings 2036, 2038 therein. The first and second gas delivery ports 2040, 2042 each have a tubular, generally cylindrical configuration with a generally circular cross-sectional profile. Further, the first gas delivery port 2040 defines a first gas delivery lumen 2044, with the second gas delivery port 2042 defining a second gas delivery lumen 2046. The first and second gas delivery lumens 2044, 2046 each fluidly communicate with the cavity 2032 of the female member 2016.

The female member 2016 further comprises a pressure sensing port 2048 and a pilot port 2050 which are identically configured to each other, and are formed on the base portion 2028 so as to protrude into the cavity 2032 in spaced, generally parallel relation to each other. The pressure sensing and pilot ports 2048, 2050 also each have a tubular, generally cylindrical configuration with a generally circular cross-sectional profile. The pressure sensing port 2048 defines a pressure sensing lumen 2052, with the pilot port 2050 defining a pilot lumen 2054. As is best seen in FIG. 46, the pressure sensing lumen 2052 fluidly communicates with the first opening 2036 proximate the first gas delivery port 2040. Similarly, the pilot lumen 2054 fluidly communicates with the second opening 2038 proximate the second gas delivery port 2042.

In interfacing the first and second bi-lumen tubes 96, 98 to the female member 2016 of the Y-connector 2012, one end portion of the first bi-lumen tube 96 is advanced into the complimentary first opening 2036 in a manner wherein the first gas delivery port 2040 is concurrently advanced into and frictionally retained within a corresponding end of the gas delivery lumen 1110 of the first bi-lumen tube 96. The advancement of the first gas delivery port 2040 into the gas delivery lumen 1110 is limited by the abutment of the end of the first bi-lumen tube 96 against the bottom of the first opening 2036 defined by the base portion 2028 of the female member 2016. Due to the complimentary shapes of the first opening 2036 and the first bi-lumen tube 96, the abutment of the end of the first bi-lumen tube 96 against the bottom of the first opening 2036 facilitates the general coaxial alignment (and fluid communication) between the pressure sensing lumen 2052 (and hence the pressure sensing port 2048) of the female member 2016 and the pressure sensing lumen 1112 of the first bi-lumen tube 96.

In a similar fashion, one end portion of the second bi-lumen tube 98 is advanced into the complimentary second opening 2038 in a manner wherein the second gas delivery port 2042 is advanced into and frictionally retained within a corresponding end of the gas delivery lumen 1114 of the second bi-lumen tube 98. The advancement of the second gas delivery port 2042 into the gas delivery lumen 1114 is limited by the abutment of the end of the second bi-lumen tube 98 against the bottom of the second opening 2038 defined by the base portion 2028 of the female member 2016. Due to the complimentary shapes of the second opening 2038 and the second bi-lumen tube 98, the abutment of the end of the second bi-lumen tube 98 against the bottom of the second opening 2038 facilitates the general coaxial alignment (and fluid communication) between the pilot lumen 2054 (and hence the pilot port 2050) of the female member 2016 and the pilot lumen 1116 of the second bi-lumen tube 98.

As indicated above, whereas the first and second gas delivery ports 2040, 2042 each have a generally circular cross-sectional configuration, the gas delivery lumens 1110, 1114 of the first and second bi-lumen tubes 96, 98 each have the generally elliptical cross-sectional configuration or profile. In the female member 2016, the relative orientations between the first gas delivery port 2040 and the pressure sensing lumen 2052 within the first opening 2036 are the same as those of the first connector 80, 180 and pressure port 84, 184 of the mask 10, 10a, 110, 110a. Similarly, the relative orientations between the second gas delivery port 2042 and the pilot lumen 2054 within the second opening 2038 are the same as those of the second connector 82, 182 and pilot port 86, 186 of the mask 10, 10a, 110, 110a. Similar to the connection of the first and second bi-lumen tubes 96, 98 to the mask 10, 10a, 110, 110a as explained above, these relative orientations may be specifically selected so as to achieve a prescribed offset between the axes of the first and second gas delivery ports 2040, 2042 and corresponding ones of the gas delivery lumens 1110, 1114 when the first and second bi-lumen tubes 96, 98 are advanced into the first and second openings 2036, 2038, respectively. More particularly, as a result of these offsets, the advancement of the first and second gas delivery ports 2040, 2042 into corresponding ends of respective ones of the gas delivery lumens 1110, 1114 may be used to facilitate the resilient deformation of each of the first and second bi-lumen tubes 96, 98 in a manner effectively compressing the web portion 1121 thereof. Such compression of the web portion 1121 could be used to effectively maintain a tight frictional engagement between the first and second bi-lumen tubes 96, 98 and respective ones of the first and second gas delivery ports 2040, 2042 which is less prone to leakage.

Figure 43:
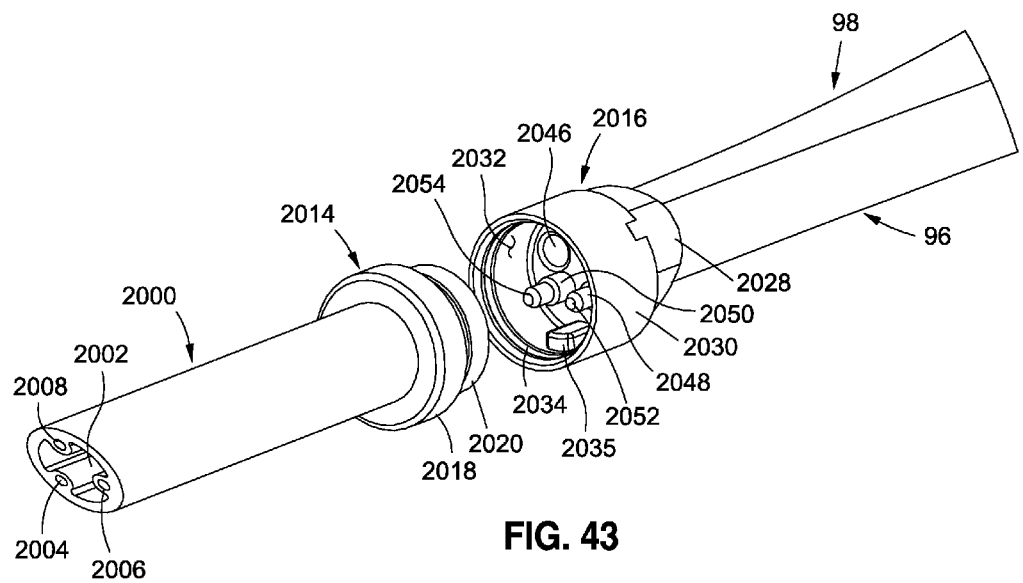
FIG. 43 is a perspective view of the Y-connector shown in FIGS. 41 and 42 in a detached state.
Figure 44:
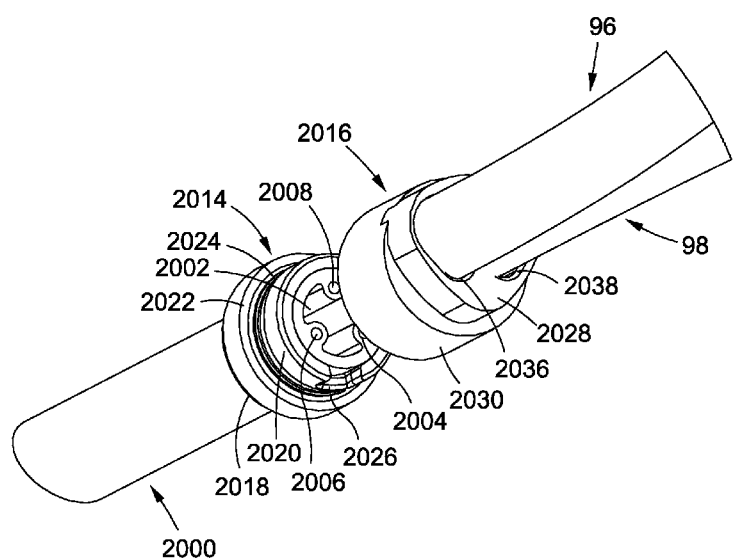
FIG. 44 is an alternative perspective view of the Y-connector shown in FIGS. 41 and 42 in a detached state.

In FIGS. 43 and 44, the male and female members 2014, 2016 of the Y-connector 2012 are shown in a separated or disconnected state. Conversely, in FIGS. 40-42, the male and female members 2014, 2016 are depicted as being operatively connected to each other. The connection of the male and female members 2014, 2016 to each other is facilitated by initially advancing the reduced diameter second portion 2020 of the male member 2014 into the complimentary cavity 2032 defined by the female member 2016. In this regard, the inner diameter of the sleeve portion 2030 of the female member 2016 slightly exceeds the outer diameter of the second portion 2020 of the male member 2014, thus allowing for the slidable advancement of the second portion 2020 into the cavity 2032. As will be recognized, in order for the second portion 2020 to be advanced into the cavity 2032, the slot 2026 of the male member 2014 must be aligned with the tab 2035 of the female member 2016. In this regard, the advancement of the second portion 2020 of the male member 2014 into the cavity 2032 of the female member 2016 results in the concurrent advancement of the alignment tab 2035 into the complimentary alignment slot 2026. The advancement of the second portion 2020 into the cavity 2032 is limited by the abutment of the distal end or rim defined by the sleeve portion 2030 of the female member 2016 against the annular shoulder 2022 defined by the male member 2014. When such an abutment occurs, the O-ring 2024 of the male member 2014 is concurrently received into and effectively seated within the complimentary channel 2034 formed within the inner surface of the sleeve portion 2030 of the female member 2016. The seating of the O-ring 2024 into the complimentary channel 2034 facilitates the formation of a fluid-tight seal between the male and female members 2014, 2016 of the Y-connector 2012 when releasably connected to each other.

Importantly, the registry or alignment between the male and female members 2014, 2016 achieved by the advancement of the alignment tab 2035 into the alignment slot 2026 in turn facilitates the coaxial alignment of the pressure sensing port 2048 of the female member 2016 with the pressure sensing lumen 2004 of the quad-lumen tube 2000, as well as the coaxial alignment of the pilot port 2050 of the female member 2016 with the pilot lumen 2006 of the quad-lumen tube 2000. In this regard, the advancement of the second portion 2020 into the cavity 2032, in addition to resulting in the advancement of the tab 2035 into the slot 2026, also results in the concurrent advancement of the pressure sensing port 2048 into the pressure sensing lumen 2004, and the pilot port 2050 into the pilot lumen 2006. As is best seen in FIG. 43, both the pressure sensing and pilot ports 2048, 2050 are provided with reduced diameter distal end portions which facilitate the advancement thereof into and frictional retention within the pressure sensing and pilot lumens 2004, 2006, respectively. In this regard, as best seen in FIG. 42, when the second portion 2020 of the male member 2014 is fully received into the cavity 2032 of the female member 2016 in the aforementioned manner, the corresponding end of the quad-lumen tube 2000 rests against the shoulders defined by the pressure sensing and pilot ports 2048, 2050 as a result of the formation of the distal end portions thereof with the reduced diameters as indicated above.

With the male and female members 2014, 2016 of the Y-connector 2012 being releasably attached to each other in the aforementioned manner, the pressure sensing lumen 2052 defined by the pressure sensing port 2048 is placed into fluid communication with the pressure sensing lumen 2004 of the quad-lumen tube 2000. As a result, the pressure sensing lumen 2004 of the quad-lumen tube 2000 is fluidly connected to the pressure sensing lumen 1112 of the first bi-lumen tube 96 by the pressure sensing lumen 2052. At the same time, the pilot lumen 2054 defined pilot port 2050 is placed into fluid communication with the pilot lumen 2006 of the quad-lumen tube 2000, thus resulting in the pilot lumen 2006 being fluidly connected to the pilot lumen 1116 of the second bi-lumen tube 98 by the pilot lumen 2054. As is also apparent from FIG. 42, the gas delivery lumen 2002 of the quad-lumen tube 2000 fluidly communicates with a portion of the cavity 2032, as do the first and second gas delivery lumens 2044, 2046 defined by the first and second gas delivery ports 2040, 2042, respectively. As a result, with the male and female members 2014, 2016 of the Y-connector 2012 being releasably connected to each other in the aforementioned manner, the gas delivery lumen 2002 of the quad-lumen tube 2000 is effectively bifurcated or divided, and thus placed into fluid communication with the gas delivery lumens 1110, 1114 of the first and second bi-lumen tubes 96, 98 via a portion of the cavity 2032 and the first and second gas delivery lumens 2044, 2046.

In the ventilation system 188, the fluid connection between the first and second bi-lumen tunes 96, 98 and the female member 2016 of the Y-connector 2012 as described above is unaffected by the detachment of the male and female members 2014, 2016 from each other. Also unaffected is the attachment between the male member 2014 and the quad-lumen tube 2000. As indicated above, the auxiliary lumen 2008 of the quad-lumen tube 2000 may be used, for example, to route optical fibers or wires as could potentially be used to illuminate the Y-connector 2012 since the auxiliary lumen 2008 communicated with a portion of the cavity 2032 when the male and female members 2014, 2016 are releasably attached to each other.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:
1. A respiratory assistance system, comprising:
a flow generator;
a ventilation mask; and
a fluid conduit fluidly coupling the flow generator to the ventilation mask, and comprising:

a multi-lumen tube which is fluidly coupled to the flow generator;

a first bi-lumen tube which has a generally teardrop-shaped cross-sectional configuration, and is fluidly coupled to and extends between the multi-lumen tube and the ventilation mask; and a second bi-lumen tube which has a generally teardrop-shaped cross-sectional configuration, and is fluidly coupled to and extends between the multi-lumen tube and the ventilation mask.

2. The respiratory assistance system of claim 1 wherein:

the multi-lumen tube defines at least a gas delivery lumen, a valve pilot lumen and a pressure sensing lumen which are each fluidly coupled to the flow generator;

the first bi-lumen tube defines a gas delivery lumen which is fluidly coupled to and extends between the gas delivery lumen of the multi-lumen tube and the ventilation mask, and a pressure sensing lumen which is fluidly coupled to and extends between the pressure sensing lumen of the multi-lumen tube and the ventilation mask; and the second bi-lumen tube defines a gas delivery lumen which is fluidly coupled to and extends between the gas delivery lumen of the multi-lumen tube and the ventilation mask, and a valve pilot lumen which is fluidly coupled to and extends between the valve pilot lumen of the multi-lumen tube and the ventilation mask.

3. The respiratory assistance system of claim 2 wherein the multi-lumen tube is a quad-lumen tube which has a generally circular cross-sectional configuration and further defines an auxiliary lumen.

4. The respiratory assistance system of claim 3 wherein the valve pilot, pressure sensing and auxiliary lumens of the quad-lumen tube are arranged about the gas delivery lumen thereof in equidistantly spaced intervals of about 120°.

5. The respiratory assistance system of claim 4 wherein the gas delivery lumen of the quad-lumen tube has a generally cloverleaf shaped cross-sectional configuration, and each of the pressure sensing, valve pilot and auxiliary lumens thereof has a generally circular cross-sectional configuration.

6. The respiratory assistance system of claim 2 further comprising:

a Y-connector which is fluidly coupled to the multi-lumen tube and each of the first and second bi-lumen tubes, the Y-connector being sized and configured to facilitate the fluid coupling of the gas delivery lumen of the multi-lumen tube to the gas delivery lumens of the first and second bi-lumen tubes, facilitate the fluid coupling of the pressure sensing lumens of the multi-lumen tube and the first bi-lumen tube to each other, and facilitate the fluid coupling of the valve pilot lumens of the multi-lumen tube and the second bi-lumen tube to each other;

the Y-connector including at least first and second members which are releasably connectable to each other as allows for the selective detachment and separation of the multi-lumen tube from each of the first and second bi-lumen tubes.

7. The respiratory assistance system of claim 6 wherein:

the Y-connector comprises male and female members;

the male member of the Y-connector is coupled to the multi-lumen tube;

the female member of the Y-connector is fluidly coupled to each of the first and second bi-lumen tubes; and the male and female members are configured so as to be releasably attachable to each other only in a manner wherein the gas delivery lumens of the multi-lumen tube and the first and second bi-lumen tubes are placed into fluid communication with each other, the pressure sensing lumens of the multi-lumen tube and the first bi-lumen tube are placed into fluid communication with each other, and the valve pilot lumens of the multi-lumen tube and the second bi-lumen tube are placed into fluid communication with each other.

8. The respiratory assistance system of claim 2 wherein:

the gas delivery lumen of each of the first and second bi-lumen tubes has a generally elliptical, oval shaped cross-sectional configuration;

the pressure sensing and valve pilot lumens of respective ones of the first and second bi-lumen tubes each have a generally circular cross-sectional configuration; and the pressure sensing and valve pilot lumens of the first and second bi-lumen tubes are separated from respective ones of the gas delivery lumens thereof by a corresponding web portion.

9. The respiratory assistance system of claim 8 wherein the ventilation mask comprises:

a first connector and a pressure port disposed in side-by-side relation to each other, the first connector having a generally circular cross-sectional configuration;

a second connector and a pilot port disposed in side-by-side relation to each other, the second connector having a generally circular cross-sectional configuration;

the relative orientations between the first connector and the pressure port, the second connector and the pilot port, the gas delivery and pressure sensing lumens of the first bi-lumen tube, and the gas delivery and pilot lumens of the second bi-lumen tube being specifically selected so as to achieve a prescribed offset between the axes of the first and second connectors and corresponding ones of the gas delivery lumens of the first and second bi-lumen tubes when the pressure and pilot ports of the mask are coaxially aligned with respective ones of the pressure sensing and pilot lumens of the first and second bi-lumen tubes, as facilitates the resilient compression of the web portion of each of the first and second bi-lumen tubes when the first and second connectors are advanced into respective ones of the gas delivery lumens of the first and second bi-lumen tubes.

10. The respiratory assistance system of claim 9 wherein:

the relative orientations of the gas delivery and pressure sensing lumens of the first bi-lumen tube are the same as those of the gas delivery and pilot lumens of the second bi-lumen tube; and the relative orientations of the first connector and the pressure port are the same as those of the second connector and the pilot port.

11. A respiratory assistance system, comprising:

a flow generator;

a ventilation mask; and a fluid conduit fluidly coupling the flow generator to the ventilation mask, and comprising:

a multi-lumen tube which defines at least a gas delivery lumen, a valve pilot lumen and a pressure sensing lumen which are each fluidly coupled to the flow generator;

a first bi-lumen tube which defines a gas delivery lumen and a pressure sensing lumen which are each fluidly coupled to the ventilation mask; and a second bi-lumen tube which defines a gas delivery lumen and a pilot lumen which are each fluidly coupled to the ventilation mask; and a Y-connector which is fluidly coupled to the multi-lumen tube and each of the first and second bi-lumen tubes, the Y-connector being sized and configured to facilitate the fluid coupling of the gas delivery lumen of the multi-lumen tube to the gas delivery lumens of the first and second bi-lumen tubes, the fluid coupling of the pressure sensing lumens of the multi-lumen tube and the first bi-lumen tube to each other, and the fluid coupling of the valve pilot lumens of the multi-lumen tube and the second bi-lumen tube to each other;

the Y-connector including at least first and second members which are releasably connectable to each other as allows for the selective detachment and separation of the multi-lumen tube from each of the first and second bi-lumen tubes.

12. The respiratory assistance system of claim 11 wherein:
the Y-connector comprises male and female members;
the male member of the Y-connector is coupled to the multi-lumen tube;
the female member of the Y-connector is fluidly coupled to each of the first and second bi-lumen tubes; and
the male and female members are configured so as to be releasably attachable to each other only in a manner wherein the gas delivery lumens of the multi-lumen tube and the first and second bi-lumen tubes are placed into fluid communication with each other, the pressure sensing lumens of the multi-lumen tube and the first bi-lumen tube are placed into fluid communication with each other, and the valve pilot lumens of the multi-lumen tube and the second bi-lumen tube are placed into fluid communication with each other.

13. The respiratory assistance system of claim 11 wherein:
the gas delivery lumen of each of the first and second bi-lumen tubes has a generally elliptical, oval shaped cross-sectional configuration; and
the pressure sensing and valve pilot lumens of the first and second bi-lumen tubes are separated from respective ones of the gas delivery lumens thereof by a corresponding web portion.

14. The respiratory assistance system of claim 13 wherein the ventilation mask comprises:
a first connector and a pressure port disposed in side-by-side relation to each other, the first connector having a generally circular cross-sectional configuration;
a second connector and a pilot port disposed in side-by-side relation to each other, the second connector having a generally circular cross-sectional configuration;
the relative orientations between the first connector and the pressure port, the second connector and the pilot port, the gas delivery and pressure sensing lumens of the first bi-lumen tube, and the gas delivery and pilot lumens of the second bi-lumen tube being specifically selected so as to achieve a prescribed offset between the axes of the first and second connectors and corresponding ones of the gas delivery lumens of the first and second bi-lumen tubes when the pressure and pilot ports of the mask are coaxially aligned with respective ones of the pressure sensing and pilot lumens of the first and second bi-lumen tubes, as facilitates the resilient compression of the web portion of each of the first and second bi-lumen tubes when the first and second connectors are advanced into respective ones of the gas delivery lumens of the first and second bi-lumen tubes.

15. The respiratory assistance system of claim 14 wherein:
the relative orientations of the gas delivery and pressure sensing lumens of the first bi-lumen tube are the same as those of the gas delivery and pilot lumens of the second bi-lumen tube; and
the relative orientations of the first connector and the pressure port are the same as those of the second connector and the pilot port.

16. A respiratory assistance system, comprising:
a flow generator;
a ventilation mask; and
a fluid conduit fluidly coupling the flow generator to the ventilation mask, and comprising:
a quad-lumen tube which is fluidly coupled to the flow generator and defines a gas delivery lumen, a valve pilot lumen, a pressure sensing lumen and an auxiliary lumen;
a first multi-lumen tube which defines at least a gas delivery lumen which is fluidly coupled to and extends between the gas delivery lumen of the quad-lumen tube and the ventilation mask, and a pressure sensing lumen which is fluidly coupled to and extends between the pressure sensing lumen of the quad-lumen tube and the ventilation mask; and
a second multi-lumen tube which defines at least a gas delivery lumen which is fluidly coupled to and extends between the gas delivery lumen of the quad-lumen tube and the ventilation mask, and a valve pilot lumen which is fluidly coupled to and extends between the valve pilot lumen of the quad-lumen tube and the ventilation mask.

17. The respiratory assistance system of claim 16 further comprising:
a Y-connector which is fluidly coupled to the quad-lumen tube and each of the first and second multi-lumen tubes, the Y-connector being sized and configured to facilitate the fluid coupling of the gas delivery lumen of the quad-lumen tube to the gas delivery lumens of the first and second multi-lumen tubes, the fluid coupling of the pressure sensing lumens of the quad-lumen tube and the first multi-lumen tube to each other, and the fluid coupling of the valve pilot lumens of the quad-lumen tube and the second multi-lumen tube to each other.

18. The respiratory assistance system of claim 16 wherein the valve pilot, pressure sensing and auxiliary lumens of the quad-lumen tube are separated from each other by intervals of approximately 120°, and each have a generally circular cross-sectional configuration.

19. The respiratory assistance system of claim 16 wherein the quad-lumen tube includes a reinforcement ribbon which is embedded therein and extends along at least a portion thereof.

20. The respiratory assistance system of claim 16 wherein:
the gas delivery lumen of each of the first and second multi-lumen tubes has a generally elliptical, oval shaped cross-sectional configuration; and
the pressure sensing and valve pilot lumens of the first and second multi-lumen tubes are separated from respective ones of the gas delivery lumens thereof by a corresponding web portion.

* * * * *